(12) United States Patent
Ghosh et al.

(10) Patent No.: US 9,309,213 B2
(45) Date of Patent: Apr. 12, 2016

(54) C-3 SUBSTITUTED BICYCLOOCTANE BASED HIV PROTEASE INHIBITORS

(75) Inventors: Arun K. Ghosh, West Lafayette, IN (US); Hiroaki Mitsuya, Kumamoto (JP); Bruno D. Chapsal, Astoria, NY (US)

(73) Assignee: Purdue Research Foundation, West Lafayette, IN (US)

(*) Notice: Subject to any disclaimer, the term of this patent is extended or adjusted under 35 U.S.C. 154(b) by 5 days.

(21) Appl. No.: 14/131,849

(22) PCT Filed: Jul. 11, 2012

(86) PCT No.: PCT/US2012/046216
§ 371 (c)(1),
(2), (4) Date: Jan. 9, 2014

(87) PCT Pub. No.: WO2013/009844
PCT Pub. Date: Jan. 17, 2013

(65) Prior Publication Data
US 2014/0148508 A1    May 29, 2014

Related U.S. Application Data

(60) Provisional application No. 61/506,238, filed on Jul. 11, 2011.

(51) Int. Cl.
*C07D 307/935* (2006.01)

(52) U.S. Cl.
CPC .................. *C07D 307/935* (2013.01)

(58) Field of Classification Search
None
See application file for complete search history.

(56) References Cited

U.S. PATENT DOCUMENTS

| 2004/0039016 A1 | 2/2004 | Ghosh et al. |
| 2010/0124543 A1 | 5/2010 | Tung et al. |
| 2011/0118330 A1* | 5/2011 | Ghosh ........................ 514/431 |

FOREIGN PATENT DOCUMENTS

| WO | WO 2008133734 A2 * | 11/2008 |
| WO | WO-2013009844 A2 | 1/2013 |

OTHER PUBLICATIONS

"International Application Serial No. PCT/US2012/046216, International Preliminary Report on Patentability mailed Jan. 23, 2014", 7 pgs.
"International Application Serial No. PCT/US2012/046216, International Search Report mailed Feb. 1, 2013", 4 pgs.
"International Application Serial No. PCT/US2012/046216, Written Opinion mailed Feb. 1, 2013", 5 pgs.

* cited by examiner

*Primary Examiner* — San-Ming Hui
*Assistant Examiner* — Andrew Lee
(74) *Attorney, Agent, or Firm* — Schwegman Lundberg & Woessner, P.A.

(57) ABSTRACT

C3-functionalized-cyclopentanyltetrahydrofuranyl carbamates that inhibit HIV proteolytic enzymes and processes for preparing the compounds are described. Compositions comprising the disclosed compound and methods of using the compounds and/or compositions for treating patients infected with HIV are also described.

17 Claims, No Drawings

C-3 SUBSTITUTED BICYCLOOCTANE BASED HIV PROTEASE INHIBITORS

CROSS-REFERENCE TO RELATED APPLICATIONS

This application is a national stage entry under 35 USC §371(b) of International Application No. PCT /US2012/ 046216, filed Jul. 11, 2012, and claims priority under 35 U.S.C. §119 to U.S. Provisional Application Ser. No. 61/506, 238 which was filed on Jul. 11, 2011, the entirety of both of which are incorporated herein by reference.

GOVERNMENT RIGHTS

This invention was made with government support under GM053386 awarded by the National Institutes of Health. The government has certain rights in the invention.

BACKGROUND AND SUMMARY

Disclosed herein are the design, synthesis, and biological evaluation of a novel inhibitor of HIV-1 protease, as well as aspects of the X-ray crystal structure of the novel inhibitor bound with HIV-1 protease. Various C3-functionalized cyclopentanyltetrahydrofurans (Cp-THF) were designed to interact with the flap Gly48 carbonyl or amide NH in the S2-subsite of the HIV-1 protease. The anti-HIV activity of these functionalized ligands combined with several hydroxyethyl sulfonamide isosteres is described. Inhibitor 25, containing a 3(R)-hydroxyl group on the Cp-THF core, displayed potent enzyme inhibitory and antiviral activity. A preference of the 3(R)-configuration over the corresponding 3(S)-derivative is described. Inhibitor 25 exhibited potent activity against a panel of multidrug-resistant HIV-1 variants.

Human immunodeficiency virus 1 (HIV-1) protease inhibitors are critical components of antiretroviral therapies. However, the emergence of drug resistance has raised serious questions about long-term treatment options. Structure-based design of inhibitors targeting the protein-backbone has led to the discovery of a variety of novel HIV-1 protease inhibitors (PIs) with broad-spectrum activity against multidrug-resistant HIV-1 variants. One of these inhibitors, darunavir (1) was approved by the FDA for the treatment of HIV/AIDS patients. Inhibitor design strategies have focused on maximizing active site interactions with the protease, particularly by promoting extensive hydrogen bonding interactions with backbone atoms throughout the active site.

Several potent inhibitors incorporating a stereochemically defined (3aS,5R,6aR)-hexahydro-2H-cyclopenta[b]furan-5yl (Cp-THF) as the P2-ligand with a modified hydroxyethylsulfonamide isostere have been described recently. The X-ray crystal structure of 3-bound HIV-1 protease revealed the formation of an extensive hydrogen-bonding network between the inhibitor and the active site. Incorporation of a stereochemically defined lactam at the P1'-position to further enhance backbone interactions has also been described. Interestingly, the resulting inhibitor 4 retained full potency against a range of multidrug-resistant HIV-1 variants. The X-ray structural studies of 4-bound HIV-1 protease evidenced enhanced backbone interactions with the Gly27' carbonyl at the S1'-subsite. Without being bound by theory, it is believed that the Cp-THF ligand fits within the S2-subsite and the cyclic ether oxygen is involved in a close hydrogen bonding interaction with the backbone NH of Asp29 (2.8 Å). Several structural modifications of the Cp-THF ligand to further improve ligand binding, particularly hydrogen bonding ability, in the S2-subsite are described herein. The X-ray structure of 3-bound HIV-1 protease indicated that the C3 methylene of the Cp-THF is in close proximity to the protease flap region. The X-ray data suggested a weak C3-H . . . O interaction with the Gly48 backbone carbonyl group. Introduction of polar substituents at the C3 position which may lead to additional interactions of the Cp-THF ligand with the protease flap residues are described herein. Without being bound by theory, it is believed that an inhibitor which makes tight interactions with the protease flap region could conceivably delay its dissociation via opening of the flaps. The design, synthesis, and biological evaluation of a series of protease inhibitors that incorporate stereochemically defined functionality at the C3 position of the Cp-THF-ligand are described. Inhibitor 25, incorporating a 3(R)-hydroxyl group was one of the most potent protease inhibitor (PI) ($K_i$=5 pM; antiviral $IC_{50}$=2.9 nM). This inhibitor also maintained excellent potency against a range of multidrug-resistant HIV-1 variants.

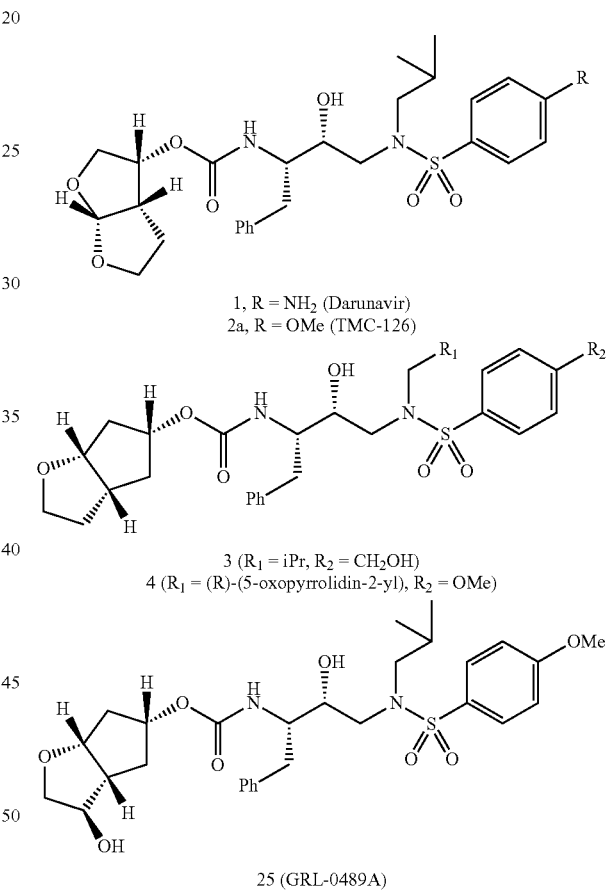

1, R = $NH_2$ (Darunavir)
2a, R = OMe (TMC-126)

3 ($R_1$ = iPr, $R_2$ = $CH_2OH$)
4 ($R_1$ = (R)-(5-oxopyrrolidin-2-yl), $R_2$ = OMe)

25 (GRL-0489A)

Structures of Potent HIV-1 Protease Inhibitors 1-4, and 25

The HIV aspartic protease plays a central role in the life cycle of the virus. It cleaves the virally encoded polyprotein and promotes the release of all essential viral enzymes and structural proteins necessary for the formation of new infective virions. Inhibition of this enzyme logically appeared as a viable strategy for the treatment of HIV-1 infection and AIDS. The development of HIV-1 protease inhibitors and their combination with reverse transcriptase inhibitors in Highly Active Antiretroviral Therapies (HAART) have drastically changed the outcome of the AIDS epidemic. These therapies effectively suppressed virus replication and increased CD4 cells counts in patients, and ultimately reduced HIV-AIDS-associated morbidity and mortality. Despite these advances, several limitations are still severely hampering current HAART regimens. Poor drug bioavailability, heavy pill burden, debilitating side effects, and high treatment cost remain serious drawbacks. However, the fast emergence of drug-resistance certainly remains the most distressing issue in the management of HIV-1 infection. Through spontaneous viral mutations, or recombination between mutated viral strains, occurrence of drug-resistance and cross-resistance quickly compromise long-term treatment options. As a result, the development of new protease inhibitors with broad-spectrum activity, less toxicity, and improved bioavailability remains a critical objective.

The design of several novel HIV-1 proteases inhibitors (PIs) with broad-spectrum activity against multidrug-resistant HIV-1 variants has been described. These include darunavir (DRV, TMC-114, 1), GRL-0476A (2), or inhibitors 3 and 4. DRV has exhibited exceptional activity against both wild-type and multi-drug resistant HIV-1 viruses. This inhibitor also showed excellent resilience towards the development of drug-induced resistance. Darunavir (1, DRV) was approved by the FDA in 2006 for the treatment of antiretroviral-experienced patients, and in 2008, extended approval was granted for treatment-naïve adults and for use in pediatrics.

Without being bound by theory, it is believed that inhibitor design relying on maximizing interactions with the protease active site, and particularly with the protease backbone atoms provides a strategy for minimizing the development of drug resistance. Several studies have noted a minimal distortion of the protease backbone is associated with mutations, it is believed that an inhibitor that strongly binds to the protease backbone atoms would retain its affinity and potency with mutant proteases. The close hydrogen bonding interactions observed between DRV, especially through its bis-THF P2 ligand, and the protease's backbone residues might explain DRV's marked potency and resistance profile.

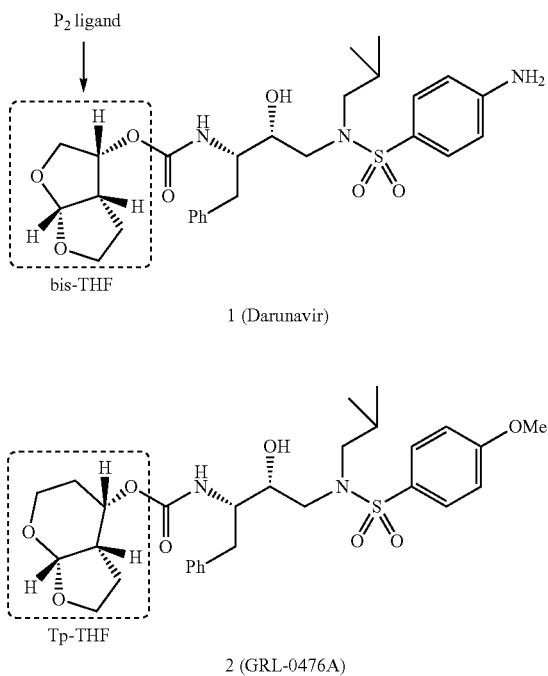

1 (Darunavir)

2 (GRL-0476A)

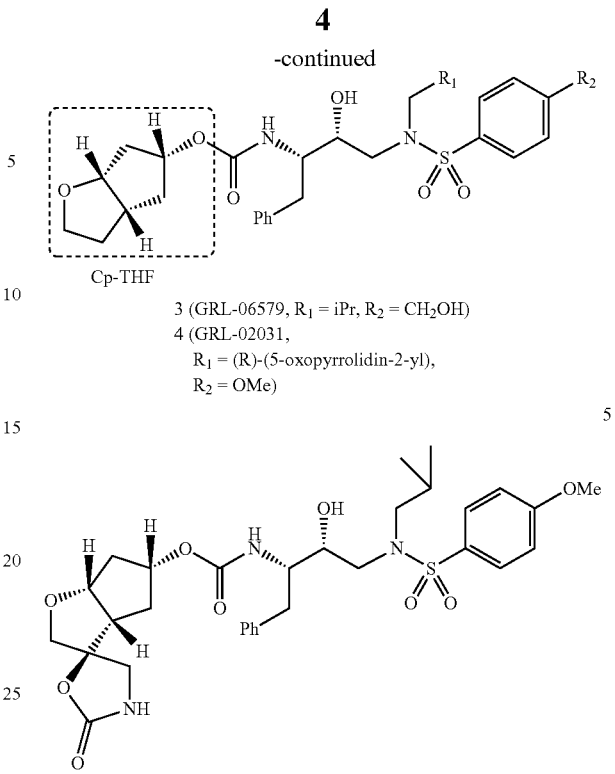

3 (GRL-06579, $R_1$ = iPr, $R_2$ = CH$_2$OH)
4 (GRL-02031,
  $R_1$ = (R)-(5-oxopyrrolidin-2-yl),
  $R_2$ = OMe)

5

Structures of Potent HIV-1 Protease Inhibitors 1-5

Inhibitors 3 and 4 have also displayed excellent activities against multidrug-resistant HIV-1 variants. These inhibitors possess a stereochemically-defined (3aS,5R,6aR)-hexahydro-2H-cyclopenta[b]furan-5-yl (Cp-THF) as the P2 ligand used in combination with a hydroxyethyl sulfonamide isostere. Similar to DRV, crystal structure analysis of the 4-bound HIV protease complex revealed an extensive hydrogen-bonding network between the inhibitor and the enzyme binding site. The Cp-THF ligand was observed to tightly fit within the S2 subsite of the protease, with the cyclic ether oxygen at close hydrogen bonding distance (2.8 Å) to the Asp29 NH backbone bond. Structure activity studies on this ligand moiety showed an important influence of the cyclic ether oxygen on the PI activity. The Cp-THF ligand was discovered to provide an important structural framework for the design of potent HIV PIs.

The effect of structural modifications of the Cp-THF ligand on inhibitor activity, by introducing additional functionalities on that ligand are described herein. It has been discovered that functional group insertion at the 3-position of the ligand yields active inhibitors. X-Ray crystal structure analysis of the 3-bound protease showed that the C3 methylene of the Cp-THF is near the flap region of the protease. Particularly, a weak C3-H . . . O interaction with the Gly-48 backbone carbonyl bond was noted previously. It was found that introducing polar substituents on the C3 position of the Cp-THF favors additional interactions with protease flap residues and enhances the binding affinity of the inhibitor. Without being bound by theory, it is believed that an inhibitor having close binding interactions with the flap region of the protease can delay its kinetics of dissociation by inhibiting the opening of the flap. Several inhibitors containing novel stereochemically-defined spirocyclic P2-ligands based on the Cp-THF framework have recently been reported. Stepwise modification of the spirocylic moiety led to inhibitors exhibiting high inhibitory potency and good antiviral activity. Spirocyclic oxazolidinone-containing inhibitor 5 showed the highest potency and activity in that group of compounds. It has been discovered that addition of polar functional groups, hydrogen bond donor or acceptor, at the 3-position of the Cp-THF, results improved inhibitor activity.

Herein, is reported the design, synthesis, and biological evaluation of a new series of inhibitors that contain Cp-THF ligand analogs with various functionalities on the C3 position. Inhibitor 25, with a (3S)-hydroxyl group, has potent PI (5 pM) and antiviral activity ($IC_{50}$=2.9 nM). Structure-activity studies revealed the benefit of introducing a hydrogen bonding donor like hydroxy at the C3 position. When evaluated against a panel of multidrug-resistant HIV-1 viruses, 25 retained high potency against all mutant strains. An X-Ray crystal structure of 25-bound HIV protease provided showed several of the interactions of the inhibitor with the protease active site as well as with the flap region of the protease.

Part B

Several illustrative embodiments of the invention are described by the following enumerated clauses:

1. A compound having the formula

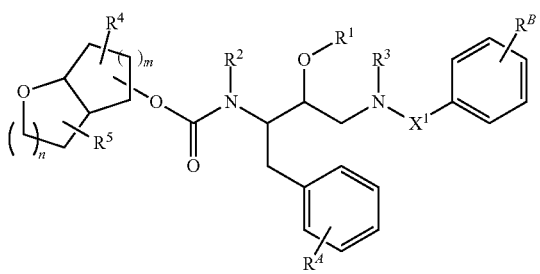

or a pharmaceutically acceptable salt, isomer, mixture of isomers, crystalline form, non crystalline form, hydrate, or solvate thereof; wherein m is 1 or 2; n is 1 or 2;

$X^1$ is C(O), S(O), S(O)$_2$, HNS(O)$_2$, HNC(O), or C(O)NH;

$R^1$ and $R^2$ are in each instance independently selected from the group consisting of hydrogen, and a prodrug forming group;

$R^A$ represents from 0 to 4 substituents independently selected in each instance from the group consisting of hydroxy, alkyl, heteroalkyl, alkyloxy, heteroalkyloxy, cycloalkyl, cycloheteroalkyl, aryl, arylalkyl, heteroaryl, or heteroarylalkyl, each of which is optionally substituted; or $R^A$ represents from 2 to 4 substituents where two of the substituents are vicinal substituents and taken with the attached carbons form a carbocycle or heterocycle; and the remaining substituents, if present, are independently selected in each instance from the group consisting of alkyl, heteroalkyl, alkyloxy, heteroalkyloxy, cycloalkyl, cycloheteroalkyl, aryl, arylalkyl, heteroaryl, or heteroarylalkyl, each of which is optionally substituted;

$R^B$ represents from 0 to 4 substituents independently selected in each instance from the group consisting of amino, alkyl, heteroalkyl, alkyloxy, heteroalkyloxy, cycloalkyl, cycloheteroalkyl, aryl, arylalkyl, heteroaryl, or heteroarylalkyl, each of which is optionally substituted; or $R^B$ represents from 2 to 4 substituents where two of the substituents are vicinal substituents and taken with the attached carbons form a carbocycle or heterocycle; and the remaining substituents, if present, are independently selected in each instance from the group consisting of alkyl, heteroalkyl, alkyloxy, heteroalkyloxy, cycloalkyl, cycloheteroalkyl, aryl, arylalkyl, heteroaryl, or heteroarylalkyl, each of which is optionally substituted;

$R^3$ is alkyl, cycloalkyl, arylalkyl, or heteroarylalkyl, each of which is optionally substituted;

$R^4$ and $R^5$ are independently selected in each instance from hydrogen, halogen, oxo, hydroxy, or the group consisting of alkyl, heteroalkyl, alkyloxy, hydroxyalkyl, acyloxy, —OC(O)-amino, acyl, amino, sulfonylamino, acylamino, alkyloxy-C(O)-amino, and alkoxyamino, each of which is optionally substituted, where at least one of $R^4$ or $R^5$ is not hydrogen.

2. The compound of clause 1 wherein m and n are not both 2.

3. The compound of clause 1 or 2 wherein m and n are 1.

4. The compound of any one of the preceding clauses wherein the compound has the formula

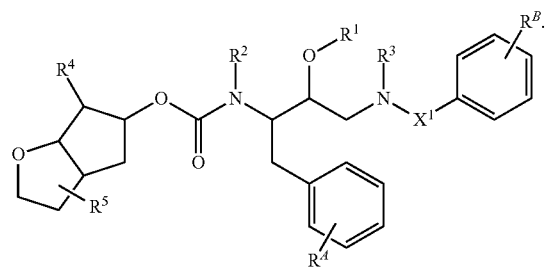

5. The compound of any one of the preceding clauses wherein the compound has the formula

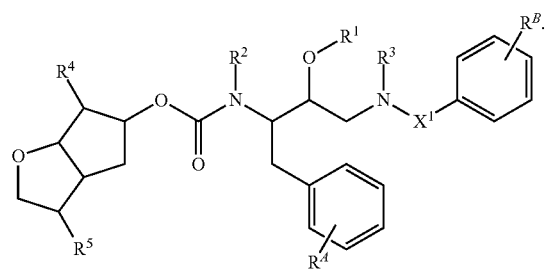

6. The compound of any one of clauses 1 to 5 wherein the compound has the formula

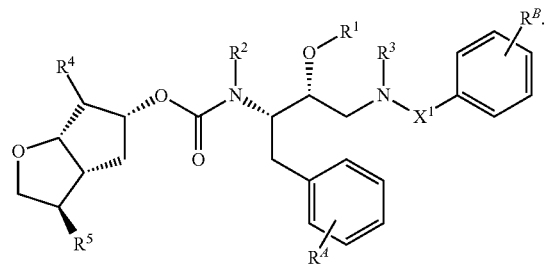

7. The compound of any one of clauses 1 to 5 wherein the compound has the formula

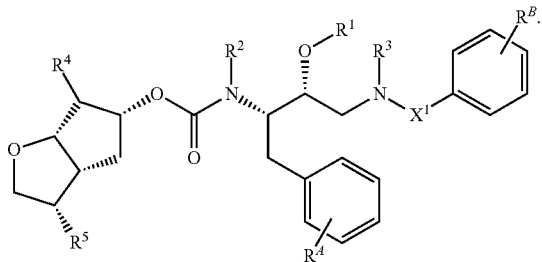

7.1 The compound of any one of clauses 1 to 7 wherein $X^1$ is $SO_2$; $R^3$ is iso-butyl; and $R^1$, $R^2$, and $R^4$ are hydrogen.

8. The compound of any one of clauses 1 to 7 wherein $R^4$ is alkyl or an oxygen containing substituent.

9. The compound of any one of the preceding clauses wherein $R^5$ is alkyl or an oxygen containing substituent.

10. The compound of any one of the preceding clauses wherein $R^B$ is a substituent at the 4-position selected from the group consisting of amino, alkyloxy, and hydroxyalkyl.

11. The compound of any one of the preceding clauses wherein $R^B$ is $NH_2$, $CH_3O$, or $CH_2OH$.

12. The compound of any one of the preceding clauses wherein $X^1$ is $S(O)_2$.

13. The compound of any one of the preceding clauses wherein $R^3$ is branched alkyl.

14. The compound of any one of the preceding clauses wherein $R^3$ is iso-butyl.

15. The compound of any one of the preceding clauses wherein $R^A$ is absent.

16. The compound of any one the preceding clauses wherein $R^1$ is hydrogen.

17. The compound of any one the preceding clauses wherein $R^2$ is hydrogen.

18. The compound of any one of the preceding clauses wherein $R^4$ is hydrogen.

18.1 The compound of any one of the preceding clauses wherein $R^5$ is selected from the group consisting of hydroxy, alkyloxy, —OC(O)-amino, acylamino, alkyloxy-C(O)-amino, and sulfonylamino.

19. The compound of any one of the preceding clauses wherein $R^5$ is selected from the group consisting of hydroxy, alkyloxy, —OC(O)-amino, acylamino, and sulfonylamino.

19.1 The compound of any one of the preceding clauses wherein $R^5$ is hydroxy, methoxy, $CH_3OC(O)NH$, or acetamido.

19.2 The compound of any one of the preceding clauses wherein $R^5$ is $CH_3OC(O)NH$.

20. The compound of any one of the preceding clauses wherein $R^5$ is hydroxy, methoxy, or acetamido.

21. The compound of any one of the preceding clauses wherein the compound binds to HIV-1 protease, where the binding includes a direct or indirect interaction between the compound and one or more amino acid residues in the protease selected from the group consisting of Asp29, Asp30, and Gly48.

22. The compound of clause 21 wherein the compound binds directly to the one or more amino acid residues.

23. The compound of clause 21 wherein the compound binds indirectly to the one or more amino acid residues, wherein the indirect binding includes an intervening group that binds to the amino acid residue and the compound, where the intervening group is independently selected in each instance from the group consisting of a water molecule, a divalent metal ion, a phosphate ion, a sulfate ion, an ammonium ion, and a monovalent metal ion.

24. The compound of clause 23 wherein the intervening group is a water molecule.

25. A pharmaceutical composition comprising one or more compounds of any one of the preceding clauses.

26. The pharmaceutical composition of clause 25 further comprising one or more carriers, diluents, or excipients, or a combination thereof.

27. A method for treating HIV in a patient, the method comprising the step of administering to the patient a therapeutically effective amount of one or more compounds of any one of clauses 1 to 24, or the composition of clauses 25 to 26.

In another embodiment, a compound having the following formula is described.

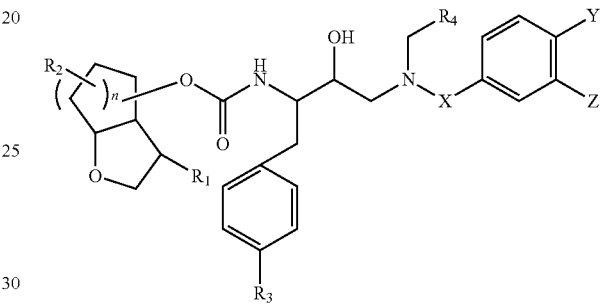

R1=alkyl, hydroxy, alkoxy, OCH2CH2O-alkyl, amine, substituted amine, urethane, amide, aminosulfonamide R1=alkyl, hydroxy, alkoxy, amine, substituted amine, urethane, amide, aminosulfonamide n=1, 2, 3

R3=alkyl, OMe, OET, O-heteroalkyl, OCH2-CH2-morpholine, OCH2-oxazole,

R4=alkyl, heteroalkyl, hydroxyalkyl, alkoxy, amine, substituted amine, urethane, amide, aminosulfonamide

X=SO2, NHSO2-, NHCO, C=ONH

Y=OMe, NH2, CH2OMe, CH2NH2, substituted amine, urethane, amide, aminosulfonamide Z=H, OMe, NH2, CH2OMe, CH2NH2, substituted amine, urethane, amide, aminosulfonamide Y—Z=4,5,6-membered ring/substituted containing heteroatoms As used herein, the term "alkyl" includes a chain of carbon atoms, which is optionally branched. As used herein, the term "alkenyl" and "alkynyl" includes a chain of carbon atoms, which is optionally branched, and includes at least one double bond or triple bond, respectively. It is to be understood that alkynyl may also include one or more double bonds. It is to be further understood that in certain embodiments, alkyl is advantageously of limited length, including $C_1$-$C_{24}$, $C_1$-$C_{12}$, $C_1$-$C_8$, $C_1$-$C_6$, and $C_1$-$C_4$. It is to be further understood that in certain embodiments alkenyl and/or alkynyl may each be advantageously of limited length, including $C_2$-$C_{24}$, $C_2$-$C_{12}$, $C_2$-$C_8$, $C_2$-$C_6$, and $C_2$-$C_4$. It is appreciated herein that shorter alkyl, alkenyl, and/or alkynyl groups may add less lipophilicity to the compound and accordingly will have different pharmacokinetic behavior. Illustrative alkyl groups are, but not limited to, methyl, ethyl, n-propyl, isopropyl, n-butyl, isobutyl, sec-butyl, tert-butyl, pentyl, 2-pentyl, 3-pentyl, neopentyl, hexyl, heptyl, octyl and the like.

As used herein, the term "cycloalkyl" includes a chain of carbon atoms, which is optionally branched, where at least a portion of the chain in cyclic. It is to be understood that cycloalkylalkyl is a subset of cycloalkyl. It is to be understood that cycloalkyl may be polycyclic. Illustrative cycloalkyl include, but are not limited to, cyclopropyl, cyclopentyl, cyclohexyl, 2-methylcyclopropyl, cyclopentyleth-2-yl, adamantyl, and the like. As used herein, the term "cycloalkenyl" includes a chain of carbon atoms, which is optionally branched, and includes at least one double bond, where at least a portion of the chain in cyclic. It is to be understood that the one or more double bonds may be in the cyclic portion of cycloalkenyl and/or the non-cyclic portion of cycloalkenyl. It is to be understood that cycloalkenylalkyl and cycloalkylalkenyl are each subsets of cycloalkenyl. It is to be understood that cycloalkyl may be polycyclic. Illustrative cycloalkenyl include, but are not limited to, cyclopentenyl, cyclohexylethen-2-yl, cycloheptenylpropenyl, and the like. It is to be further understood that chain forming cycloalkyl and/or cycloalkenyl is advantageously of limited length, including $C_3$-$C_{24}$, $C_3$-$C_{12}$, $C_3$-$C_8$, $C_3$-$C_6$, and $C_5$-$C_6$. It is appreciated herein that shorter alkyl and/or alkenyl chains forming cycloalkyl and/or cycloalkenyl, respectively, may add less lipophilicity to the compound and accordingly will have different pharmacokinetic behavior.

As used herein, the term "heteroalkyl" includes a chain of atoms that includes both carbon and at least one heteroatom, and is optionally branched. Illustrative heteroatoms include nitrogen, oxygen, and sulfur. In certain variations, illustrative heteroatoms also include phosphorus, and selenium. As used herein, the term "cycloheteroalkyl" including heterocyclyl and heterocycle, includes a chain of atoms that includes both carbon and at least one heteroatom, such as heteroalkyl, and is optionally branched, where at least a portion of the chain is cyclic. Illustrative heteroatoms include nitrogen, oxygen, and sulfur. In certain variations, illustrative heteroatoms also include phosphorus, and selenium. Illustrative cycloheteroalkyl include, but are not limited to, tetrahydrofuryl, pyrrolidinyl, tetrahydropyranyl, piperidinyl, morpholinyl, piperazinyl, homopiperazinyl, quinuclidinyl, and the like.

As used herein, the term "aryl" includes monocyclic and polycyclic aromatic carbocyclic groups, each of which may be optionally substituted. Illustrative aromatic carbocyclic groups described herein include, but are not limited to, phenyl, naphthyl, and the like. As used herein, the term "heteroaryl" includes aromatic heterocyclic groups, each of which may be optionally substituted. Illustrative aromatic heterocyclic groups include, but are not limited to, pyridinyl, pyrimidinyl, pyrazinyl, triazinyl, tetrazinyl, quinolinyl, quinazolinyl, quinoxalinyl, thienyl, pyrazolyl, imidazolyl, oxazolyl, thiazolyl, isoxazolyl, isothiazolyl, oxadiazolyl, thiadiazolyl, triazolyl, benzimidazolyl, benzoxazolyl, benzthiazolyl, benzisoxazolyl, benzisothiazolyl, and the like.

As used herein, the term "amino" includes the group $NH_2$, alkylamino, and dialkylamino, where the two alkyl groups in dialkylamino may be the same or different, i.e. alkylalkylamino. Illustratively, amino includes methylamino, ethylamino, dimethylamino, methylethylamino, and the like. In addition, it is to be understood that when amino modifies or is modified by another term, such as aminoalkyl, or acylamino, the above variations of the term amino are included therein. Illustratively, aminoalkyl includes $H_2N$-alkyl, methylaminoalkyl, ethylaminoalkyl, dimethylaminoalkyl, methylethylaminoalkyl, and the like. Illustratively, acylamino includes acylmethylamino, acylethylamino, and the like.

As used herein, the term "amino and derivatives thereof" includes amino as described herein, and alkylamino, alkenylamino, alkynylamino, heteroalkylamino, heteroalkenylamino, heteroalkynylamino, cycloalkylamino, cycloalkenylamino, cycloheteroalkylamino, cycloheteroalkenylamino, arylamino, arylalkylamino, arylalkenylamino, arylalkynylamino, heteroarylamino, heteroarylalkylamino, heteroarylalkenylamino, heteroarylalkynylamino, acylamino, and the like, each of which is optionally substituted. The term "amino derivative" also includes urea, carbamate, and the like.

As used herein, the term "hydroxy and derivatives thereof" includes OH, and alkyloxy, alkenyloxy, alkynyloxy, heteroalkyloxy, heteroalkenyloxy, heteroalkynyloxy, cycloalkyloxy, cycloalkenyloxy, cycloheteroalkyloxy, cycloheteroalkenyloxy, aryloxy, arylalkyloxy, arylalkenyloxy, arylalkynyloxy, heteroaryloxy, heteroarylalkyloxy, heteroarylalkenyloxy, heteroarylalkynyloxy, acyloxy, and the like, each of which is optionally substituted. The term "hydroxy derivative" also includes carbamate, and the like.

As used herein, the term "acyl" includes formyl, and alkylcarbonyl, alkenylcarbonyl, alkynylcarbonyl, heteroalkylcarbonyl, heteroalkenylcarbonyl, heteroalkynylcarbonyl, cycloalkylcarbonyl, cycloalkenylcarbonyl, cycloheteroalkylcarbonyl, cycloheteroalkenylcarbonyl, arylcarbonyl, arylalkylcarbonyl, arylalkenylcarbonyl, arylalkynylcarbonyl, heteroarylcarbonyl, heteroarylalkylcarbonyl, heteroarylalkenylcarbonyl, heteroarylalkynylcarbonyl, acylcarbonyl, and the like, each of which is optionally substituted.

The term "optionally substituted" as used herein includes the replacement of hydrogen atoms with other functional groups on the radical that is optionally substituted. Such other functional groups illustratively include, but are not limited to, amino, hydroxyl, halo, thiol, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof, and the like. Illustratively, any of amino, hydroxyl, thiol, alkyl, haloalkyl, heteroalkyl, aryl, arylalkyl, arylheteroalkyl, heteroaryl, heteroarylalkyl, heteroarylheteroalkyl, and/or sulfonic acid is optionally substituted.

As used herein, the terms "optionally substituted aryl" and "optionally substituted heteroaryl" include the replacement of hydrogen atoms with other functional groups on the aryl or heteroaryl that is optionally substituted. Such other functional groups illustratively include, but are not limited to, amino, hydroxy, halo, thio, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof, and the like. Illustratively, any of amino, hydroxy, thio, alkyl, haloalkyl, heteroalkyl, aryl, arylalkyl, arylheteroalkyl, heteroaryl, heteroarylalkyl, heteroarylheteroalkyl, and/or sulfonic acid is optionally substituted.

Results and Discussions

Inhibitors were designed to make additional interactions in the S2-subsite of the protease, especially with the Gly48 backbone atoms in the flap region of the enzyme. All inhibitors in Table 1 were first evaluated in the enzyme inhibitory assay developed by Toth and Marshall (Toth and Marshall, *Int. J. Pept. Protein Res.* 1990, 36, 544-550). Inhibitors that exhibited potent $K_i$ values were subsequently evaluated for in vitro antiviral assays. As can be seen in the Table 1, all inhibitors displayed sub-nanomolar to low picomolar inhibitory potencies. Inhibitor 22, with a 3-(S)-hydroxy group on the Cp-THF, was significantly more potent than the keto derivative 19a (entries 1 and 2). The 3-(S)-hydroxy Cp-THF ligand was also investigated in combination with other sulfonamide substituents. Inhibitor 123 with a p-amino sulfonamide as the P2'-ligand displayed impressive inhibitory potency, however, its antiviral activity was 3-fold lower than 22. Inhibitor 23 with a p-hydroxymethyl sulfonamide as the P2'-ligand has shown a reduction in potency. Inhibitor 19b which contains a 3-(S)-methoxy substituent, exhibited a significant loss of potency and a near 5-fold loss of antiviral activity compared to 22. Inhibitor 25 with 3-(R) configuration displayed an impressive enzyme inhibitory and antiviral activity. Inhibitor 26 with the 4-amino sulfonamide isostere also showed comparable enzyme inhibitory activity. Inhibitor 19d, with a 3-(R)-methoxy group, also exhibited comparable inhibitory potency.

In order to probe the importance of the C3-hydroxyloxygen on the Cp-THF ring, inhibitors 19e and 19f, with a methyl group in place of a C3-oxygen were synthesized. Inhibitor 19e, which contains a 3(S)-methyl group showed a significant reduction in potency compared to 22. Similarly, inhibitor 19f with a 3(R)-methyl group has shown a reduction in enzyme $K_i$ value compared to the corresponding hydroxy derivative 25. An amine substitution on the Cp-THF ligand is also described. Inhibitor 24c with C3-dimethylamine exhibited lower enzyme inhibitory potency compared to the corresponding hydroxyl or methoxyl derivatives.

Inhibitors 22 with a 3(S)-hydroxyl group and 25 with a 3(R)-hydroxyl group on the Cp-THF ligand were tested against a panel of multidrug-resistant HIV-1 variants. Their antiviral activity was compared against other clinically available PIs including APV and DRV. The results are shown in Table 2. All inhibitors in Table 2 exhibited high antiviral activity against the wild-type HIV-1 laboratory strain, HIV-$1_{ERS104pre}$, isolated from a drug-naïve patient. Compound 25 provided the most potent activity with an $IC_{50}$ of 2.9 nM, comparable to that of DRV. When tested against various multidrug-resistant HIV-1 strains, the $IC_{50}$ values of inhibitor 25 remained in the low nanomolar values (2.9-29 nM), and the relative change in $IC_{50}$ did not exceed 10-fold. Isomeric inhibitor 22 displayed lower activity against the wild-type viral strain ($IC_{50}$=20 nM). It also exhibited a much larger relative $IC_{50}$ change, and in some cases, only low activity against multidrug-resistant HIV-1 variants. The contrast in antiviral activity of 22 compared to 25 underlines the importance of the stereochemistry at the 3-position of the Cp-THF ligand. Inhibitor 25 displayed a superior profile compared to another approved PI, APV. Overall, inhibitor 25 maintained high potency against all tested multidrug-resistant HIV-1 strains. It showed comparable activity to DRV, which is the leading PI for the treatment of multidrug resistant HIV infection.

An X-ray crystal structure of the inhibitor-bound wild-type HIV-1 protease, refined to a 1.45 Å resolution has been determined. The protease dimer binds with the inhibitor in two orientations related by a 180° rotation with a 0.55/0.45 ratio. The protease backbone structure showed a very low RMS deviation of 0.15 Å for all Ca atoms compared to protease complexes of 2-bound inhibitor and darunavir. The inhibitor binds with extensive interactions across the S2 to ST ligands with the protease atoms, and most notably displays favorable polar interactions including hydrogen bonds, weaker C—H . . . O and C—H . . . pi interactions. The central hydroxyl group forms hydrogen bonds with the side chain carboxylate oxygen atoms of the catalytic Asp25 and Asp25' residues. The inhibitor hydrogen bonds with the protease backbone atoms of the amide of Asp30', the carbonyl oxygen of Gly27, and forms water-mediated interactions with the amides of Ile50 and Ile50', which are conserved in the majority of protease complexes with inhibitors or substrate analogs. The inhibitor interactions with atoms in the binding cavity resemble those of darunavir and TMC-126 with the exception of the interactions of the new P2-ligand that replaces the bis-THF group. The 3-(R)-hydroxyl of the Cp-THF ligand extends towards the flap region and forms a new water-mediated hydrogen bond interaction with the backbone amide NH of Gly48, with interatomic distances of 2.5 Å, 3.1 Å for the major inhibitor orientation or 2.7 Å, 3.1 Å for the minor orientation, respectively. Also, the Cp-THF ether oxygen forms a strong hydrogen bond with the backbone amide NH of Asp29. Without being bound by theory, it is believed that these new interactions with the backbone atoms of Gly48 are responsible for the high antiviral activity against wild-type and drug resistant HIV. The C3-functionality on the Cp-THF appears to enhance the affinity of the inhibitor. Without being bound by theory, it is believed that the new water-mediated interaction with the backbone NH of Gly48 on the protease flap may promote thermodynamic stabilization of the closed conformation of the protease-ligand complex. This interaction may slow the kinetics of dissociation of the inhibitor through flexible opening of the protease flap.

Preparation of C3-substituted hexahydrocyclopentafuranyl urethanes as P2-ligands with enhanced interactions with the protein backbone in the S2-subsite is described herein. The ligands were stereoselectively synthesized in optically active form. Incorporation of these ligands in (R)-hydroxyethylsulfonamide isosteres resulted in a series of new and highly potent HIV-1 protease inhibitors. In particular, inhibitor 25 displayed remarkable enzyme inhibitory and antiviral potency. Also, inhibitor 25 has shown excellent activity against multi-PI-resistant variants compared to other FDA approved inhibitors. A protein-ligand X-ray structure of 25-bound HIV-1 protease was determined at 1.45 Å resolution. The inhibitor appears to make extensive interactions throughout the active site. Of particular interest, the 3-(R)-hydroxyl of the Cp-THF ligand formed a new water-mediated hydrogen bond interaction with the backbone amide NH of Gly48 and the Cp-THF ether oxygen formed a strong hydrogen bond with backbone amide NH of Asp29. Without being bound by theory, it is believed that extensive interactions with the protein backbone may be responsible for inhibitor 25's high antiviral activity and drug resistance profiles. The design of inhibitors with additional binding to the protein backbone has led to the development of inhibitors characterized by high potency against both wild-type and multi-drug-resistant HIV-1 strains.

Inhibitors were designed to induce additional interactions in the protease active site, especially by targeting the Gly48 backbone bonds in the flap region of the enzyme. All inhibitors were first tested for their enzyme inhibitory potency using the assay protocol developed by Toth and Marshall. Compounds that exhibited high inhibitory activities were further evaluated by in vitro antiviral assays.

Inhibitors having an oxygen functionality on the C3-position of the Cp-THF ligand were evaluated and their respective activities were compared (Table 1).

TABLE 1
Enzymatic inhibitory and antiviral activity of inhibitors.
| Inhibitor | Ki (nM) | IC$_{50}$ (μM)$^a$ |
|---|---|---|
| 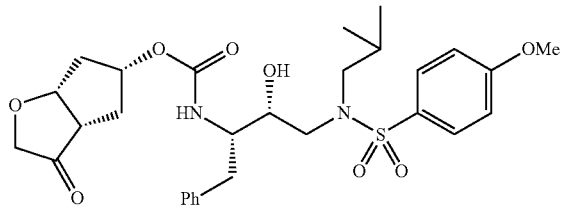 19a | 0.95 | 0.014 |
| 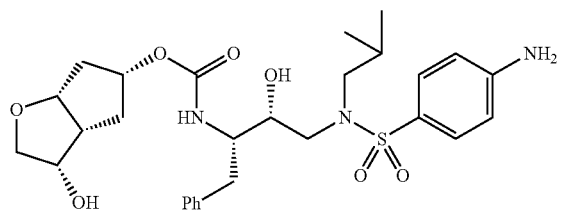 123 | 0.079 | 0.025 |
| 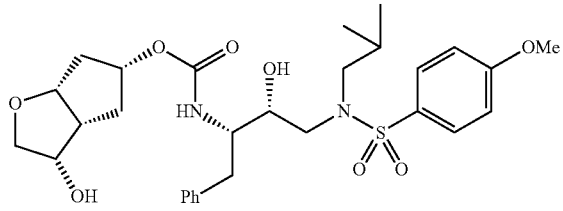 22 | 0.050, 0.077 | 0.005, 0.007 |
| 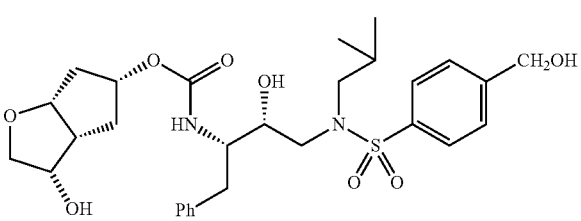 23 | 0.060 | 0.019 |
| 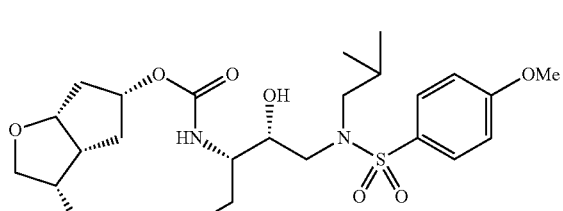 19b | 0.95, 0.39 | 0.037 |

TABLE 1-continued

Enzymatic inhibitory and antiviral activity of inhibitors.

| Inhibitor | Ki (nM) | IC$_{50}$ ($\mu$M)$^a$ |
|---|---|---|
| 25 | 0.005 | 0.0029 |
| 26 | 0.006 | 0.036 |
| 19d | 0.006 | 0.0034 |
| 19e | 0.020, 0.16 | 0.025 |
| 19f | .017 | — |

$^a$Values are means of at least two experiments. Human T-lymphoid (MT-2) cells (2 × 10$^3$) were exposed to 100 TCID$_{50}$s of HIV-1$_{LAI}$ and cultured in the presence of each PI, and IC$_{50}$ values were determined using the MTT assay. The IC$_{50}$ values of amprenavir (APV), saquinavir (SQV), and indinavir (IDV) were 0.03 $\mu$M, 0.015 $\mu$M, and 0.03 $\mu$M, respectively.

As can be seen from the results shown in Table 1, all inhibitors displayed sub-nanomolar to low picomolar inhibitory potencies. Inhibitor 22, with a 3-(S)-hydroxy group on the Cp-THF, displayed high inhibitory potency of 50 pM and a high antiviral activity with an IC$_{50}$ of 5 nM (Table 1). Inhibitor 23 also displayed high enzyme inhibitory potency and cellular activity. However, the IC$_{50}$ was 4-fold higher than that of 22. Inhibitor 19b that contains 3-(S)-methoxy substituent, exhibited loss of potency (K$_i$=0.95 nM) and a near 7-fold loss of antiviral activity (IC$_{50}$=37 nM) compared to 22.

Compared with inhibitor 25, inhibitor 26 with the 4-amino sulfonamide isostere showed slight loss of activity. Inhibitor 19d, with a 3-(R)-methoxy group, provided a comparable inhibitory potency (6 pM) and antiviral activity. These results contrast with those obtained with inhibitor 22 and 19b.

Inhibitors 19e and 19f, with a methyl group in place of a C3-oxygen substitution, were synthesized to understand the importance of the C3-hydroxyl oxygen on the Cp-THF ring in 22 and 25. Inhibitor 19e, which contains a (R)-methyl group in place of the (R)-hydroxyl on the C3-position showed a 5-fold lessening of antiviral activity compared to 22. A similar lessing of activity was also observed with inhibitor 19f, confirming the critical role of the cyclic THF oxygen for the inhibitor potency.

Inhibitors containing CP-THF ligand with amine substitutions were also prepared. Inhibitors with C3-N-amide, -sulfonamide or a free amine on the Cp-THF core were synthesized and the inhibitors were evaluated for their enzymatic potencies and antiviral activities (Table 2).

TABLE 2

Enzymatic Inhibitory and Antiviral Activity of Inihibitors.

| Inhibitor | $K_i$ (nM) | $ID_{50}$ (μM) |
|---|---|---|
| 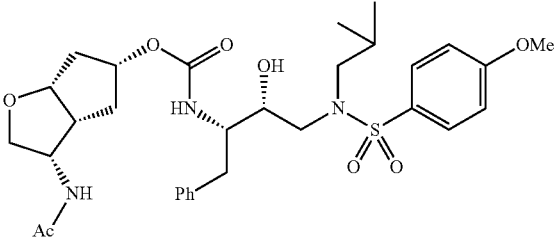 [SMILES: COc1ccc(S(=O)(=O)N(CC(C)C)C[C@@H](O)[C@H](Cc2ccccc2)NC(=O)O[C@@H]2C[C@@H]3[C@H](O)CO[C@@H]3C2)cc1] 19g | 0.0074 | 0.0215, 0.025 |
| 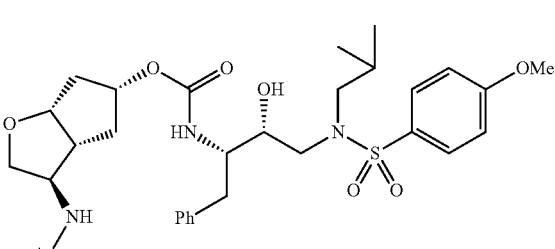 19h | 0.0075 | 0.031 |
| 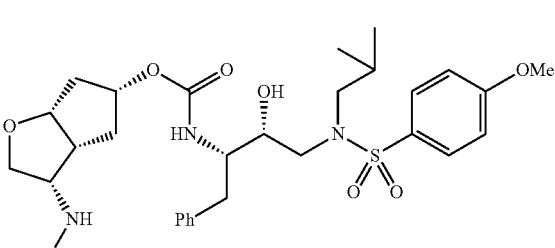 19i | 0.017, 0.032 | 0.028 |
| 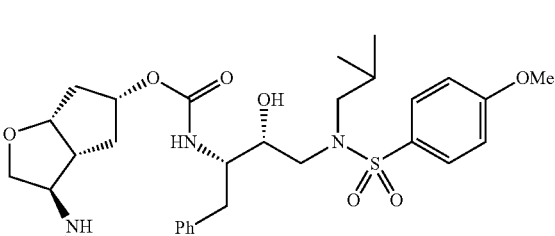 19j | 0.18 | 0.05 |

TABLE 2-continued
Enzymatic Inhibitory and Antiviral Activity of Inihibitors.
| Inhibitor | $K_i$ (nM) | $ID_{50}$ (μM) |
|---|---|---|
| 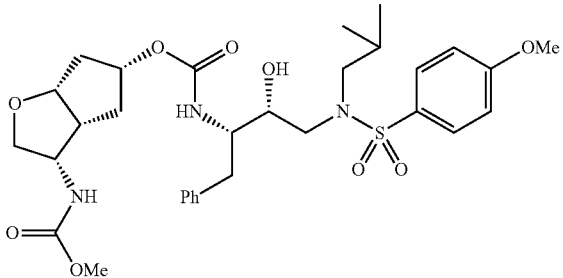 19l | 0.0018 | 0.0016 |
| 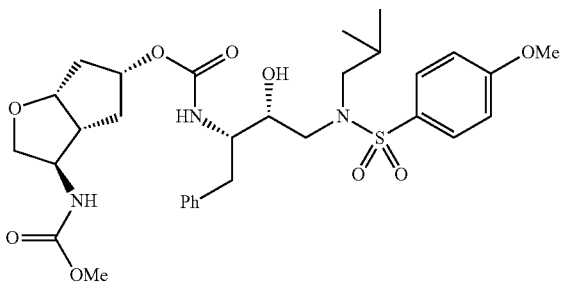 19m | 0.004 | 0.0046 |
| 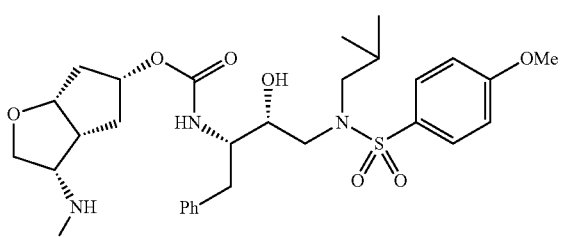 24a | 0.088 | 0.0815 |
| 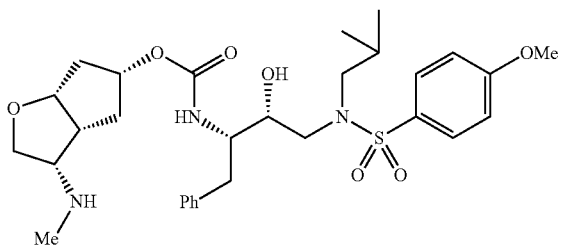 24b | — | — |
| 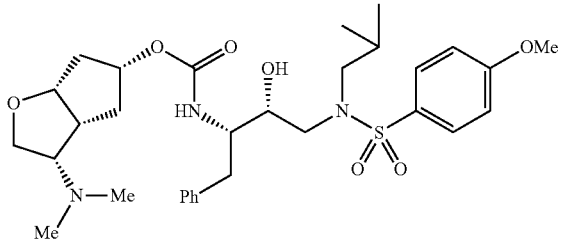 24c | 12.7 nM | — |

TABLE 2-continued

Enzymatic Inhibitory and Antiviral Activity of Inihibitors.

| Inhibitor | $K_i$ (nM) | $ID_{50}$ (μM) |
|---|---|---|
| 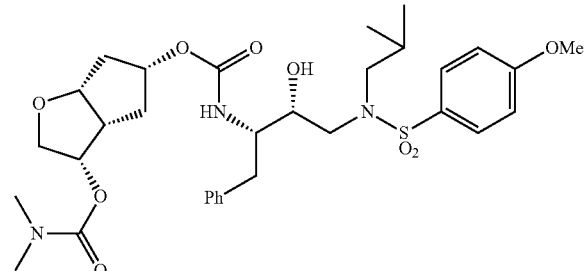 19k | 0.020 | 0.0047 |

As shown in Table 2, inhibitors 19g and 19h with an acetamido group on the P2 ligand displayed high enzymatic potency (both 7 pM) and antiviral activities ($IC_{50}$=25 nM and 31 nM, respectively). The opposite stereochemistry at C-3 for inhibitors 19i and 19j had little influence on the respective activities, which were comparable.

Inhibitors 22 and 25 were tested against a panel of multidrug-resistant HIV-1 variant and its antiviral activity with that of other clinically available PIs including DRV. Results are shown in Table 3. All tested inhibitors exhibited high antiviral activity against the wild-type HIV-1 laboratory strain, HIV-$1_{ERS104pre}$, isolated from a drug-naïve patient. Compound 25 provided the most potent activity with an $IC_{50}$ of 2.9 nM, comparable to that of DRV ($IC_{50}$=3.7 nM). When tested against various multidrug-resistant HIV-1 strains, 25's $IC_{50}$ remained in the low nanomolar values (i.e. 2.9-29 nM), and fold-change in $IC_{50}$ did not even exceed 10. Interestingly, when compared to 25, isomeric inhibitor 22 displayed lower activity against the wild-type viral strain ($IC_{50}$=20 nM). It also exhibited much larger $IC_{50}$ fold-change, or even negligible activity, against multidrug-resistant HIV-1. Such a stark contrast in antiviral activities underlines the importance of the stereochemistry at the 3-position of the P2 ligand. Clinically available PI, APV, exhibited lower $IC_{50}$ values and smaller resilience to drug-resistant viruses. Overall, inhibitor 25 maintained impressively high activity against all multidrug-resistant HIV-1 strains. It compared favorably with DRV, which is the leading PI for the treatment of multi-drug resistant HIV infection.

Inhibitors 19l and 19m, were further evaluated against a panel of multidrug-resistant (MDR) HIV-1 variants and their antiviral activities were compared to clinically available PI, darunavir (DRV). Results are shown in Table 4. All inhibitors exhibited low nanomolar $EC_{50}$ values against the wild-type HIV-$1_{ERS104pre}$ laboratory strain, isolated from a drug-naïve patient. Inhibitor 3d had the most potent activity ($EC_{50}$=3 nM) similar to that of DRV. When tested against a panel of multidrug-resistant HIV-1 strains, the $EC_{50}$ of 19m remained in the low nanomolar value range (15-24 nM) and its fold-changes in activity were similar to those observed with DRV. Interestingly, inhibitor 19l, with the opposite (S)-stereochemistry at C3, displayed slightly lower antiviral activities against all viral strains compared to 19m. However, the fold changes in $EC_{50}$ for 19l remained low (<3) against all MDR HIV-1 viruses. The fold-changes contrasted with those of 19m and even DRV, for which the respective $EC_{50}$'s increased by a factor of at least three against the MDR viruses examined.

TABLE 3

Comparison of the antiviral activity of 22, 25, and of other PIs against multidrug resistant HIV-1 variants.

| | $IC_{50}$ (μM) ± SDs, (fold change)[b] | | | |
|---|---|---|---|---|
| Virus[a] | 25 | 22 | APV | DRV |
| HIV-$1_{ERS104pre}$ (wild type) | 0.0029 ± 0.0008 | 0.020 ± 0.004 | 0.030 ± 0.006 | 0.0037 ± 0.0001 |
| HIV-$1_{MDR/B}$ | 0.029 ± 0.007 (10) | >1 (>50) | 0.93 ± 0.28 (31) | 0.036 ± 0.013 (10) |
| HIV-$1_{MDR/C}$ | 0.022 ± 0.003 (7) | >1 (>50) | 0.26 ± 0.03 (9) | 0.013 ± 0.0004 (4) |
| HIV-$1_{MDR/G}$ | 0.0045 ± 0.0007 (2) | 0.27 ± 0.02 (13) | 0.38 ± 0.03 (12) | 0.0023 ± 0.0006 (1) |
| HIV-$1_{MDR/TM}$ | 0.0031 ± 0.002 (1) | 0.041 ± 0.004 (2) | 0.19 ± 0.06 (6) | 0.0019 ± 0.0003 (1) |

[a]Amino acid substitutions identified in the protease-encoding region compared to the consensus type B sequence cited from the Los Alamos database; L10I, L33I, M36I, M46I, F53L, K55R, I62V, L63P, A71V, G73S, V82A, L90M, and I93L in HIV-1MDR/B; L10I, I15V, K20R, L24I, M36I, M46L, I54V, I62V, L63P, K70Q, V82A, and L89M in HIV-1MDR/C; L10I, V11I, T12E, I15V, L19I, R41K, M46L, L63P, A71T, V82A, and L90M in HIV-1MDR/G; L10I, K14R, R41K, M46L, I54V, L63P, A71V, V82A, L90M, I93L in HIV-1MDR/TM. HIV-1ERS104pre served as a source of wild-type HIV-1. IC50s were determined by using PHA-PBMs as target cells, and inhibition of p24 Gag protein production by each drug was used as an end point. Numbers in parentheses represent n-fold changes of IC50s for each isolate compared to IC50s for wild-type HIV-1ERS104pre. All assays were conducted in duplicate or triplicate, and data shown represent mean values (±1 standard deviation) derived from results of three independent experiments. PHA-PBMs were derived from a single donor in each independent experiment. DRV (Darunavir), APV (Amprenavir).

TABLE 4

Comparison of the antiviral activity of 19l, 19m, and DRV against multidrug-resistant HIV-1 variants

| Virus[a] | EC$_{50}$ (μM) ± SDs, (fold-change) | | |
|---|---|---|---|
| | 19l | 19m | DRV |
| HIV-1$_{ERS104pre}$ (wt) | 0.029 ± 0.002 | 0.003 ± 0.001 | 0.004 ± 0.001 |
| HIV-1$_{MDR/B}$ (X4) | 0.075 ± 0.011 (3) | 0.018 ± 0.003 (6) | 0.019 ± 0.006 (5) |
| HIV-1$_{MDR/C}$ (X4) | 0.030 ± 0.006 (1) | 0.015 ± 0.005 (5) | 0.011 ± 0.003 (3) |
| HIV-1$_{MDR/G}$ (X4) | 0.039 ± 0.001 (1) | 0.020 ± 0.005 (7) | 0.011 ± 0.002 (3) |
| HIV-1$_{MDR/TM}$ (X4) | 0.074 ± 0.006 (3) | 0.024 ± 0.004 (8) | 0.028 ± 0.001 (7) |

[a]Amino acid substitutions identified in the protease-encoding region of HIV-1$_{ERS104pre}$, HIV-1$_{MDR/B}$, HIV-1$_{MDR/C}$, HIV-1$_{MDR/G}$, HIV-1$_{MDR/TM}$ compared to the consensus type B sequence cited from the Los Alamos database include L63P in HIV-1$_{ERS104pre}$; L10I, K14R, L33I, M36I, M46L, F53I, K55R, I62V, L63P, A71V, G73S, V82A, L90M, I93L in HIV-1$_{MDR/B}$; L10I, I15V, K20R, L24I, M36I, M46L, I54V, I62V, L63P, K70Q, V82A, and L89M in HIV-1$_{MDR/C}$; L10I, V11I, T12E, I15V, L19I, R41K, M46L, L63P, A71T, V82A, and L90M in HIV-1$_{MDR/G}$; L10I, K14R, R41K, M46L, I54V, L63P, A71V, V82A, L90M, I93L in HIV-1$_{MDR/TM}$. HIV-1$_{ERS104pre}$ served as a source of wild-type HIV-1.
[b]EC$_{50}$ values were determined by using PHA-PBMs as target cells and the inhibition of p24 Gag protein production for each drug was used as an endpoint. The numbers in parentheses represent the fold-change in EC$_{50}$ values for each isolate compared to the EC$_{50}$ values for the wild-type HIV-1$_{ERS104pre}$. All assays were conducted in duplicate, and the data shown represent mean values (±1 standard deviations) derived from the results of two or three independent experiments. PHAPBMs were derived from a single donor in each independent experiment. DRV (darunavir).

Chemistry

The synthesis of 3-keto and 3-(S)-methoxy Cp-THF ligands is shown in Scheme 1. Optically active alcohol 6 was prepared in multigram quantities as described previously. (Deardorff, et al., *Org. Synth., Coll. Vol. IX*, 1998, 9, 487) This was efficiently converted to ketone 7 as reported previously (Ghosh, et al., *Org. Lett.* 2008, 10, 5135-5138). The removal of TBS-ether by exposure to HF-pyridine afforded keto alcohol 9a in 94% yield. Ketone 7 was converted to 3-(S)-methoxy derivative 9b in a three-step sequence involving (1) reduction of the ketone with NaBH$_4$ in ethanol at −23° C. to provide the corresponding alcohol as a single diastereomer; (2) methylation of the resulting alcohol with MeI in the presence of Ag$_2$O in acetonitrile; and (3) removal of the silyl group with TBAF in THF to provide 9b in 66% yield, in 3 steps.

The syntheses of 3(R)-acetoxy and 3(R)-methoxy ligands 9c and 9d are outlined in Scheme 2. Treatment of alcohol 6 with NaH and 2-bromoacetic acid in THF provided the corresponding alkylated acid. The resulting acid was reacted with methyl iodide in the presence of NaHCO$_3$ to provide methyl ester 10 in 53% yield (2 steps). Dibal-H reduction of ester 10 followed by radical cyclization of the resulting alkene using a catalytic amount of (nBu$_3$Sn)$_2$O, Ph$_2$SiH$_2$ and ethanol (2 equiv) in the presence of a catalytic amount of AIBN in benzene provided 3-(R)-hydroxy derivative 11 in 64% yield, in two steps. The $^1$H-NMR analysis showed a diastereomeric ratio of 10:1. The major isomer was separated by silica gel chromatography and used for the subsequent reactions. Reaction of alcohol 11 with acetic anhydride and triethylamine in the presence of a catalytic amount of DMAP afforded the corresponding acetate. The removal of silyl group with TBAF in THF provided ligand 9c in 73% yield, in 2 steps. Alcohol 11 was converted to methoxy derivative 9d by alkylation with NaH and MeI in THF followed by removal of the silyl group in 71% yield (2 steps).

In another aspect, synthesis of stereochemically defined 3-methyl derivatives to compare the effects of alkoxy and hydroxy groups is described. Stereoselective syntheses of 3(S) and 3(R)-methyl derivatives is described in the synthetic route shown in Scheme 3. Optically active olefin 113 was synthesized as described previously. Catalytic hydrogenation of 113 in the presence of Wilkinson's catalyst under a hydrogen filled balloon at 23° C. for 3 h, followed by removal of the silyl group using TBAF afforded 3(S)-methyl derivative 9e. For the synthesis of the 3-(S)-methyl derivative, commercially available optically active lactone (+)-115 was methylated using LDA and MeI at −78° C. to provide methyl derivative 116 with high diastereoselectivity (dr=20:1) and in 95% yield. Olefin 116 was then subjected to oxymercuration condition with Hg(OAc)$_2$. The resulting organomercurial derivative was treated with aqueous sodium hydroxide solution followed by NaBH$_4$ reduction to afford endo-alcohol 117 in 64% yield. The lactone was then reduced to the corresponding lactol with Dibal-H. Further reduction of the resulting lactol using Et$_3$SiH and TiCl$_4$ furnished ligand 3-(R)-methyl derivative 9f in 68% yield. The $^1$H-NMR NOESY experiments fully corroborated the assignment of 3(S)- and 3(R)-stereochemistry of methyl derivatives 9e and 9f, respectively.

Scheme 3. Syntheses of C3-methyl-substituted ligands 9e and 9f.

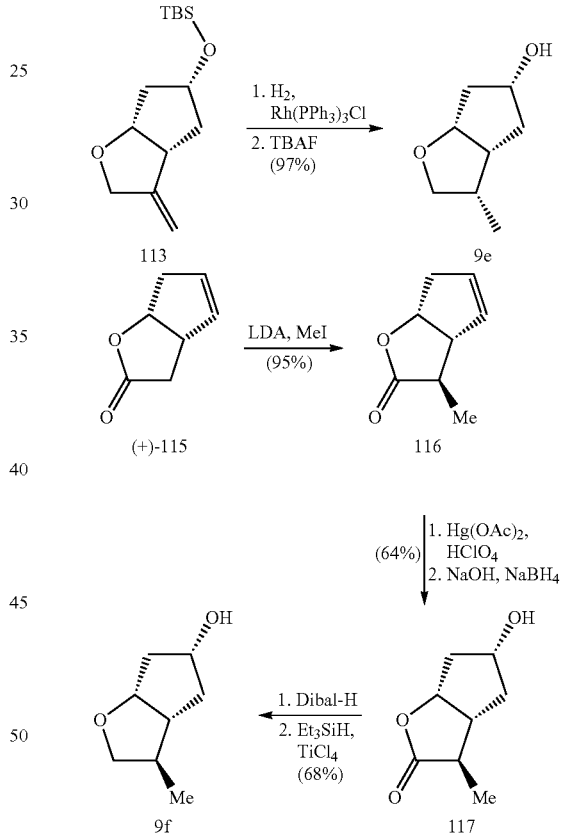

Various optically active ligand alcohols 9a, 9b, 9c, 9d, 9e, and 9f were converted to the respective mixed activated carbonates. As shown in Scheme 4, reactions of ligand alcohols with 4-nitrophenyl chloroformate in the presence of pyridine in CH$_2$Cl$_2$ provided activated carbonates 15a-f in 50-96% yield. The synthesis of designed inhibitors was carried out by coupling these activated carbonates with various hydroxyethylsulfonamide isosteres containing functionalized P2'-phenylsulfonamide ligands. As shown in Scheme 5, amines 16-18 were readily prepared as described previously. Reaction of amine 16 with carbonate 15a provided inhibitor 19a. Inhibitors 22, 123 and 23 were prepared by reaction of carbonate 15a with respective amines 16-18 followed by NaBH₄ reduction of the resulting ketone derivatives. The inhibitor structures are shown in Table 1. Inhibitors 19b and 19d-f were prepared by reactions of amine 16 with mixed carbonates 15b and 15d-f, respectively. The synthesis of inhibitors 25 and 26 was carried out by reactions of mixed carbonate 15c with amines 16 and 17 followed by removal of the acetyl group with $K_2CO_3$ in methanol. All inhibitors were prepared in good to excellent overall (41-96%) yields. The synthesis of inhibitor 24c containing a dimethylamine functionality was carried out by reductive amination of ketone 19a with $Me_2NH_2^+OAc^-$ in the presence of $NaHB(OAc)_3$. We have also attempted to prepare the corresponding methylamine derivative by reductive amination with $MeNH_3^+OAc^-$. However, the resulting 3(S)-methylamine derivative 24b turned out to be unstable.

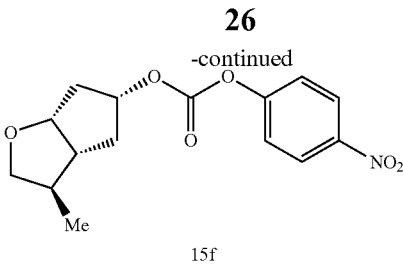

15f

Scheme 5. Syntheses of inhibitors.

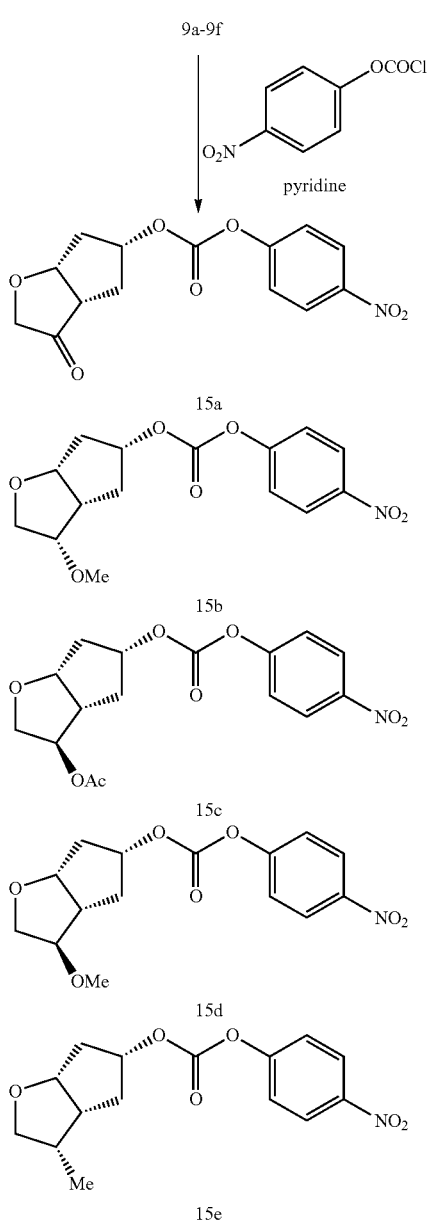

For the synthesis of the Cp-THF derived ligands, previously reported ketone 7[25] was used as a common intermediate (Scheme 1). This ketone was easily synthesized in five steps starting from enantiopure alcohol 6, as previously reported (Scheme 1) (Ghosh, et al., *Org. Lett.* 2008, 10, 5135-5138). Initially inhibitors including oxygen-containing functionalities on the C3-position were prepared. For the syntheses of a 3-(R)-hydroxy Cp-THF ligand, and its corresponding inhibitor, ketoalcohol 9a was used as a precursor (Scheme 1). It was directly obtained from 7 by simple removal of the TBS group with HF-pyridine in up to 94% yield. Ligand 9b containing a 3-(R)-methoxy group was synthesized in three steps, starting with 1) stereoselective reduction of ketone 7 using NaBH$_4$ in EtOH at −25° C., 2) methylation of the free hydroxyl group using MeI/Ag$_2$O, then 3) removal of the silyl group with TBAF to give 9b in 76% yield (3 steps).

Scheme 1. Syntheses of optically pure P$_2$ ligands 9a and 9b.

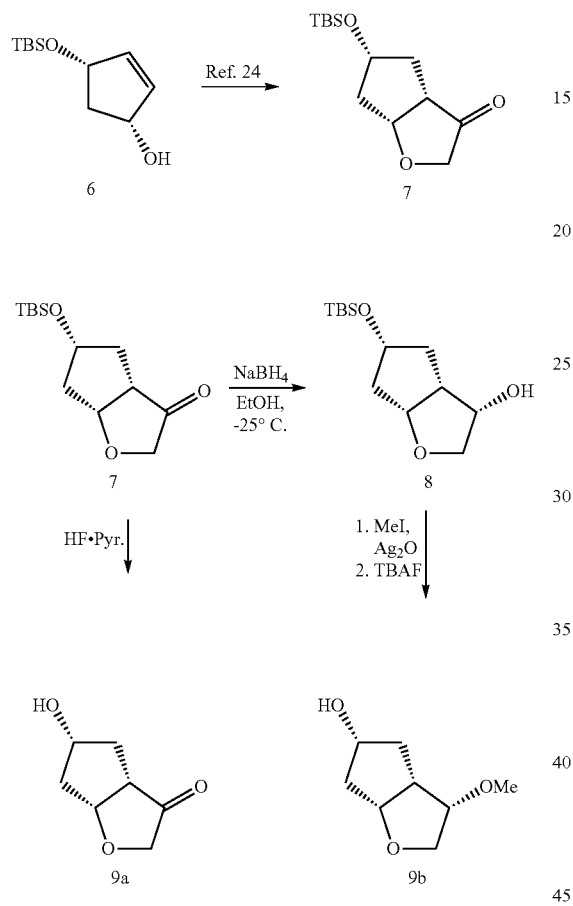

Scheme 2. Syntheses of ligands 9c and 9d.

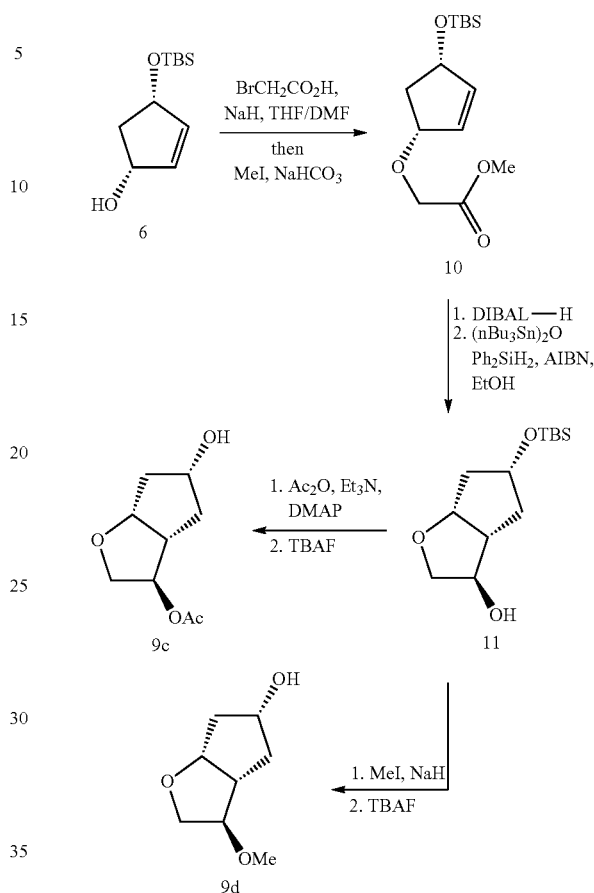

The syntheses of the corresponding P2 ligands with opposite (S)-stereochemistry at the C3-position are shown in Scheme 2. Reaction of alcohol 6 with 2-bromoacetic acid, followed by methylation of the resulting acid, furnished methyl ester intermediate 10. DIBAL-H reduction of the methyl ester to the corresponding aldehyde and radical cyclization of the 1,5-alkenal using (nBu$_3$Sn)$_2$O, Ph$_2$SiH$_2$, AIBN and EtOH in benzene, gave desired intermediate 3-(R)-11 in 67% yield (2 steps, d.r.=10:1). For the synthesis of an inhibitor containing a 3-(R)-hydroxy group on the Cp-THF, ligand precursor 9c was made by 1) protection of the free hydroxyl group of 11 with Ac$_2$O and 2) TBAF-mediated deprotection of the silyl group. The 3-(S)-methoxy Cp-THF analog was synthesized by methylation of alcohol 12 followed by TBAF-deprotection to furnish corresponding P2 ligand 9d (Scheme 2).

Ligands 9e and 9f in which the C3-hydroxyl was respectively replaced by a methyl group were also prepared to aid in understanding the gain in binding affinity of provided by the C3 hydroxyl. (Scheme 3a). The synthesis of P2 ligand 9e is outlined in Scheme 3a. Intermediate 6 was reacted with (Z)-1-ethoxy-propene in the presence of N-iodosuccinimide in CH$_2$Cl$_2$ to furnish the corresponding iodoacetal 12, as a ca. 1:1 mixture of diastereoisomers. Radical cyclization of the 1,5-iodoalkene was performed utilizing n-Bu$_3$SnH and Et$_3$B as a radical initiator to furnish the corresponding cyclized ligand 13 (>99%, four diastereoisomers, d.r.=1:1.7:2:2.7). Reduction of the acetals under Kishi's condition (Et$_3$SiH, BF$_3$-Et$_2$O) followed by TBAF-promoted removal of the TBS group provided the respective 3-(S) and 3-(R) diastereoisomeric alcohols. Ratio and assignment of stereochemistry of 9e and 9f were subsequently confirmed by NOESY analysis on their respective mixed activated carbonate.

Scheme 3a. Alternative synthesis of C3-methyl-substituted CpTHF ligand.

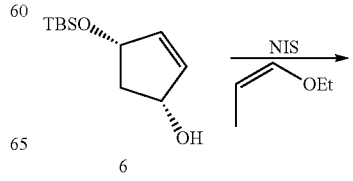

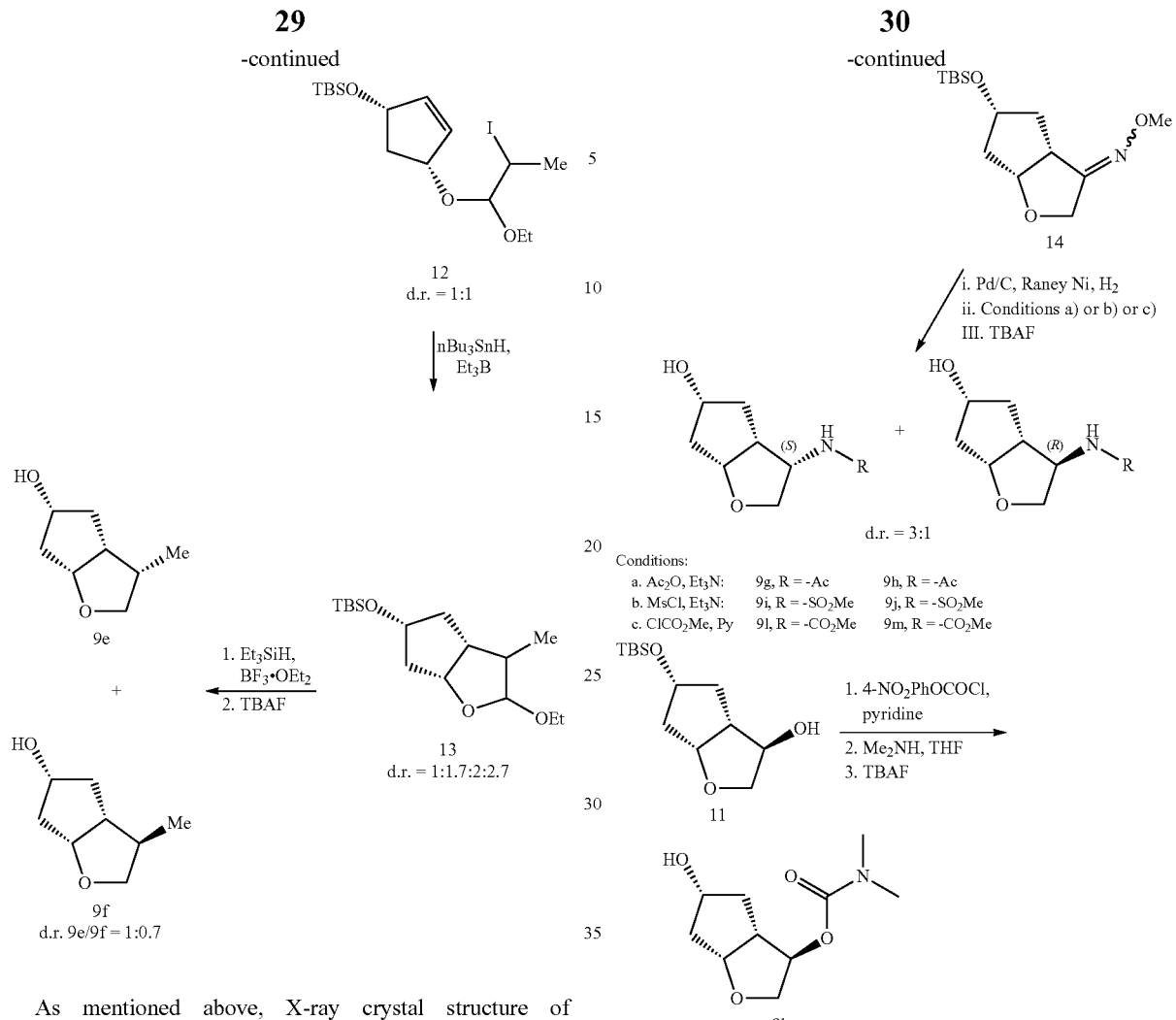

As mentioned above, X-ray crystal structure of GRL02310-bound HIV-1 protease revealed a close proximity of the Cp-THF C3 methylene to the backbone carbonyl of Gly-48 in the flap region of the protease. Several inhibitors containing a hydrogen bond donor, such as the NH of an amide, sulfonamide, or carbamate in that position of the P2 ligand were prepared, to determine the effect of a hydrogen bond with the Gly-48 carbonyl. Without being bound by theory, it is believed that the carbonyl or sulfonamide oxygens could also engage in hydrogen bonding with the proximal Gly-48 NH backbone bond. To complete the synthesis of ligands containing a nitrogen-based substituent, ketone 7 was modified into O-methyl oxime 14 in 96% yield (Scheme 4a). The oxime was then reduced to the corresponding amine under hydrogenative conditions using a mixture of Pd/C and Raney Ni to give the corresponding amine as a 3:1 mixture of diastereoisomers.

Scheme 4a. Syntheses of ligands 9g-k.

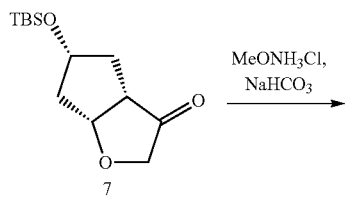

Following reduction of oxime, the crude amine was directly treated with Ac$_2$O in presence of Et$_3$N and a catalytic amount of DMAP giving the corresponding isomeric TBS-protected amide intermediates. Treatment of the respective amides with TBAF in THF furnished isomeric ligands 9g and 9h. Likewise, the amines mixture was reacted with MsCl and Et$_3$N and subsequent treatment with TBAF furnished the diastereoisomeric sulfonamides 9i and 9j, respectively. For comparison purposes, ligand 9k, which contains a 3-(R)-dimethylaminoformamoyloxy group at the C3 position, was also synthesized. This ligand possesses a carbamate carbonyl group as potential hydrogen bonding acceptor but is devoid of the NH bond as hydrogen bonding donor.

A general method for the synthesis of inhibitors is shown in Scheme 5a. Alcohols 9a-k were respectively reacted with para-nitrophenyl chloroformate in the presence of pyridine in CH$_2$Cl$_2$ to furnish the corresponding activated carbonates 15a-k. The syntheses of the HIV protease inhibitors were then carried out as shown in Scheme 5a. Hydroxyethylene isosteres 16, 17, and 18, were respectively treated with 30% TFA in CH$_2$Cl$_2$ to furnish the corresponding deprotected amine isosteres. The amines were reacted with the appropriate mixed activated carbonate, 15a-m, in presence of Et$_3$N in THF/CH$_3$CN at 23° C. for 2-4 days to furnish the corresponding inhibitors, or intermediates, 19a-k, 20, and 21.

Scheme 5a. Syntheses of inhibitors and intermediates 19a-k, 20, and 21.

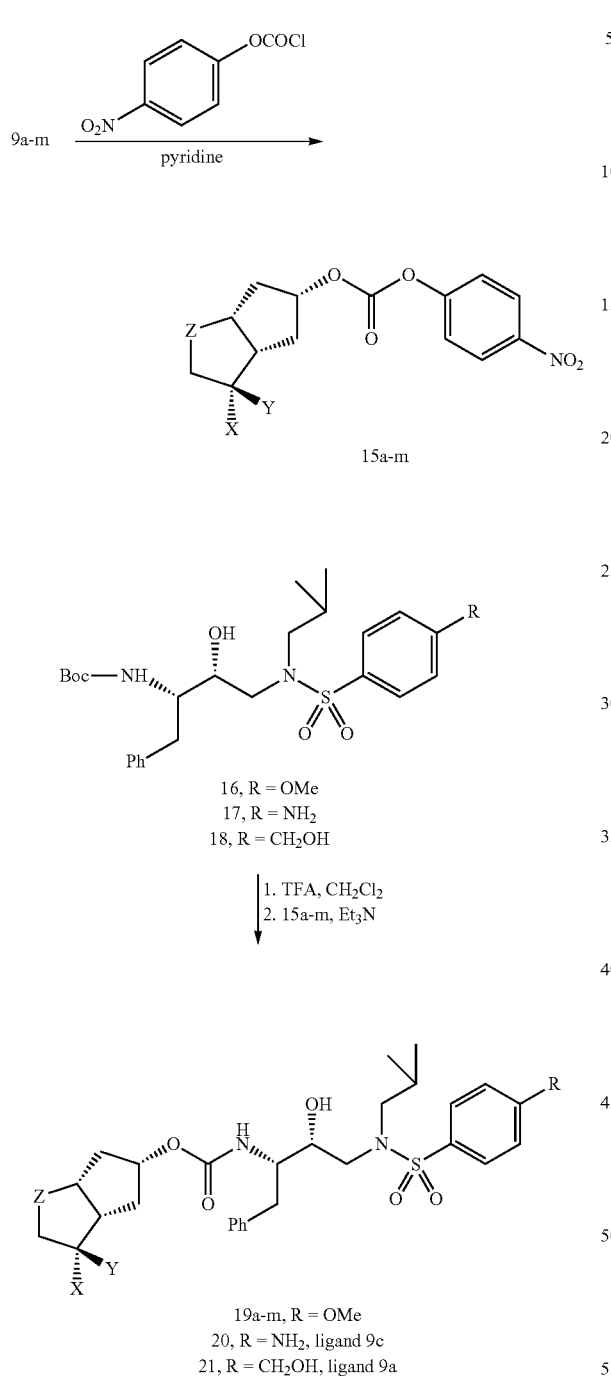

Scheme 6. Syntheses of inhibitors 22, 23, and 24a-c.

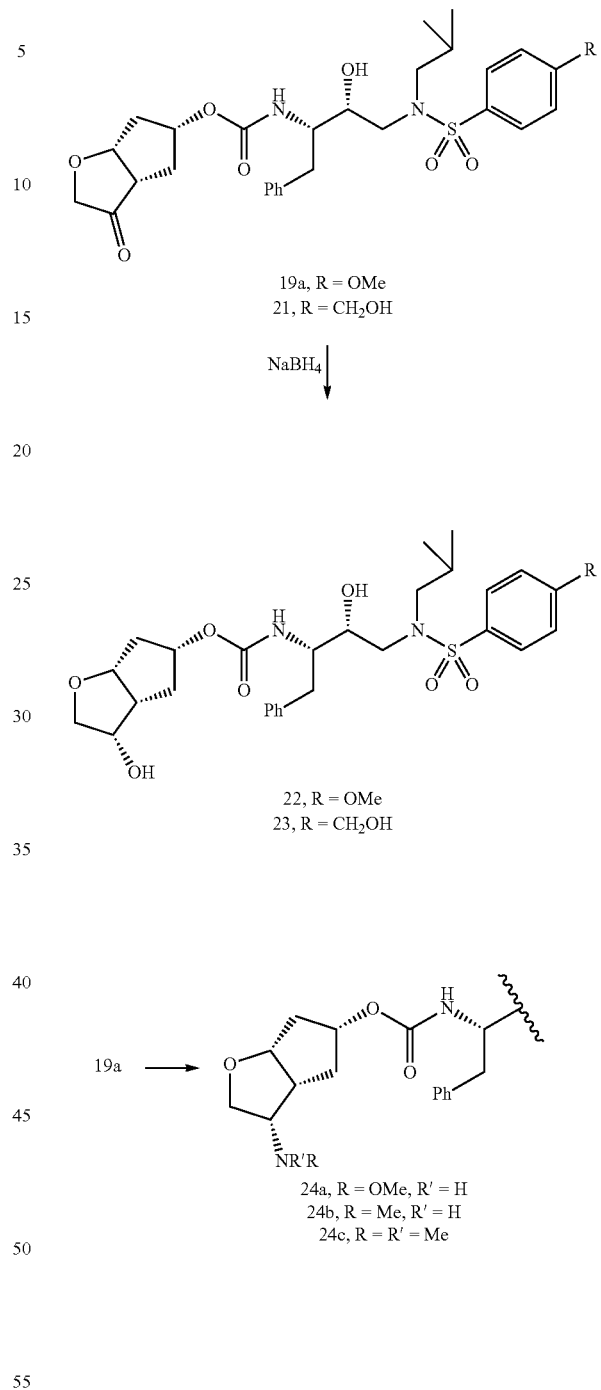

Ketone-based inhibitor intermediates 19a, 21 were obtained from the coupling of 15a with isosteres 16, and 18, respectively. Both were reacted with $NaBH_4$ in EtOH to respectively furnish inhibitors 22, and 23, that contain the 3-(S)-hydroxy Cp-THF ligand (Scheme 6).

Synthesis of inhibitors with a free amine functionality was undertaken. Thus, compound 19a was reacted with O-methyl hydroxylamine hydrochloride to form the corresponding oxime, which was reduced with $NaBH_3CN$ in acetic acid to give O-methyl hydroxylamine inhibitor 24a. Reductive amination of ketone 19a with $MeNH_2$ and $Me_2NH$ provided the respective inhibitors 24b and 24c.

The acetate of each intermediate 19c and 20 was removed by methanolysis. The reactions furnished respective free 3-(R)-hydroxyl-containing inhibitors 25 and 26 (Scheme 7).

Scheme 7. syntheses of inhibitors 25 and 26.

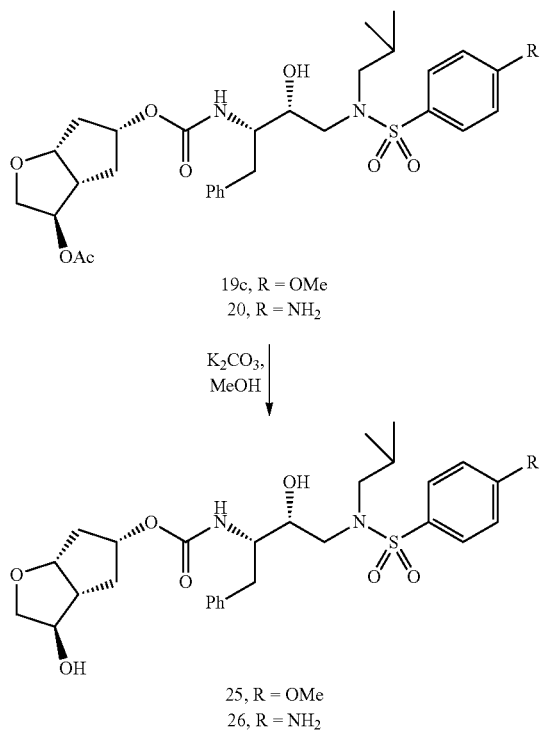

19c, R = OMe
20, R = NH$_2$

K$_2$CO$_3$, MeOH

25, R = OMe
26, R = NH$_2$

METHODS AND EXAMPLES

General. All anhydrous solvents were obtained according to the following procedures: diethyl ether and tetrahydrofuran (THF) were distilled from sodium/benzophenone under argon; toluene, methanol, acetonitrile and dichloromethane from calcium hydride, and benzene from sodium. Other solvents were used without purification. All moisture-sensitive reactions were carried out in flame-dried flasks under argon atmosphere. Reactions were monitored by thin layer chromatography (TLC) using Silicycle 60A-F$_{254}$ silica gel pre-coated plates. Flash column chromatography was performed using Silicycle 230-400 mesh silica gel. Yields refer to chromatographically and spectroscopically pure compounds. Optical rotations were recorded on a Perkin Elmer 341 polarimeter. $^1$H NMR and $^{13}$C NMR spectra were recorded on a Varian Inova-300 (300 and 75 MHz, respectively), Bruker Avance ARX-400 (400 and 100 MHz), and Bruker Avance ARX-500 (500 and 125 MHz). High and low resolution mass spectra were carried out by the Mass Spectroscopy Center at Purdue University.

(3aS,5R,6aR)-5-hydroxytetrahydro-2H-cyclopenta[b]furan-3(3aH)-one (9a). A solution of ketone 7 (23 mg) in CH$_3$CN (0.5 mL) was cooled to 0° C. under argon. Pyridine (50 μL) was added followed by dropwise addition of HF.Pyridine solution (0.18 mL). The solution was stirred at 0° C. for 4 h. The reaction was quenched by addition of a NaHCO$_3$ saturated solution followed by solid NaHCO$_3$. The aqueous phase was successively extracted with EtOAc and the combined organic layer dried over Na$_2$SO$_4$. Following careful evaporation of the mixture, the residue was purified by column chromatography on silica gel using hexanes:EtOAc (1:1 then 1:2) as eluent yielding the desired alcohol 10a (12 mg, 94%) as a colorless oil. TLC: R$_f$=0.32 (hexanes:EtOAc=1:2); [α]$_D^{20}$+96.1° (c 0.86, CHCl$_3$); $^1$H NMR (CDCl$_3$, 400 MHz) δ 5.04 (t, J=6.6 Hz, 1H), 4.38 (m, 1H), 4.20 (d, J=17 Hz, 1H), 3.97 (d, J=17.0 Hz), 2.85 (t, J=8.4 Hz, 1H), 2.21 (d, J=13.9 Hz, 1H), 2.15 (d, J=15.2 Hz, 1H), 2.07-1.90 (m, 3H); $^{13}$C NMR (CDCl$_3$, 75 MHz) δ 217.7, 83.9, 72.9, 70.8, 48.8, 43.4, 40.7.

(3S,3aR,5R,6aR)-5-((tert-butyldimethylsilyl)oxy) hexahydro-2H-cyclopenta[b]furan-3-ol (8). Ketone 7 (35.6 mg, 0.14 mmol) was dissolved in EtOH (1 mL) under argon and cooled to −25° C. To the solution was added NaBH$_4$ (10 mg, 0.26 mmol) at once, and the resulting mixture was stirred at this temperature for 20 min. Saturated aqueous NH$_4$Cl solution was added and the volume of solvent was reduced in vacuo. Additional water was added and the phase was extracted several times with EtOAc. The combined organic layer was washed with brine, dried (Na$_2$SO$_4$), and evaporated under vacuum. Purification of the crude alcohol by column chromatography on silica gel using hexanes/EtOAc (5:1) as the eluent provided alcohol 8 (32.2 mg, 90%) as a colorless oil. TLC: R$_f$=0.33 (hexanes/EtOAc=5:1); [α]$_D^{20}$+21.5 (c 1.05, CHCl$_3$); $^1$H NMR (CDCl$_3$, 300 MHz) δ 4.55 (br. s, 1H), 4.42 (t, J=7 Hz, 1H), 4.34 (t, J=4.5 Hz, 1H), 4.11 (m, 1H), 3.87 (d, J=9.9 Hz, 1H), 3.48 (dd, J=3.6, 9.9 Hz, 1H), 2.89 (dt, J=7.8, 10.2 Hz, 1H), 2.13 (dd, J=2.4, 14.7 Hz, 1H), 1.99 (dd, J=2.4, 14.7 Hz, 1H) 1.78-1.65 (m, 2H), 0.89 (s, 9H), 0.11 (s, 3H), 0.10 (s, 3H); $^{13}$C NMR (CDCl$_3$, 75 MHz) δ 85.3, 77.3, 74.9, 72.9, 48.1, 41.8, 34.8, 25.7, 18.0, −4.7, −5.2; HRMS-CI (m/z): [M+H]$^+$ calcd for C$_{13}$H$_{27}$O$_3$Si 259.1729. found 259.1731.

(3S,3aS,5R,6aR)-3-methoxyhexahydro-2H-cyclopenta[b]furan-5-ol (9b). To a solution of alcohol 8 (27 mg, 0.1 mmol) in CH$_3$CN (0.6 mL) was added MeI (0.3 mL, excess) followed by Ag$_2$O (50 mg, 0.2 mmol). The mixture was gently refluxed for 12 h under argon then additional MeI (0.3 mL) and Ag$_2$O (50 mg) were added. Reflux was continued for an additional 12 h until which all SM disappeared. The resulting mixture was diluted in ether and filtered on celite. After evaporation of the solvent, the residue was purified by column chromatography on silica gel using hexanes/EtOAc (8:1) as the eluent to yield the corresponding methoxy intermediate as a clear oil (23 mg, 85%). TLC: R$_f$=0.38 (hexanes:EtOAc=5:1); [α]$_D^{20}$+42.6 (c 1.02, CHCl$_3$); $^1$H NMR (CDCl$_3$, 300 MHz) δ 4.41 (m, 1H), 4.12 (m, 1H), 3.93 (m, 1H), 3.87-3.70 (m, 2H), 3.32 (s, 3H), 2.61 (m, 1H), 2.18 (m, 1H), 1.90-1.75 (m, 2H), 1.63 (m, 1H), 0.88 (s, 9H), 0.05 (s, 6H); $^{13}$C NMR (CDCl$_3$, 75 MHz) δ 82.5, 81.1, 73.5, 69.0, 57.8, 42.6, 33.5, 25.8, 18.1, −4.8. To a solution of the above intermediate (16 mg, 0.059 mmol) in THF (0.5 mL) was added TBAF (1M solution in THF, 0.09 mmol, 90 μL). The solution was stirred at room temperature for 2 h. The solvent was evaporated and the residue purified by flash column chromatography on silica gel using hexanes/EtOAc (1:1 then 1:2.5) to furnish 9b as a colorless oil (8 mg, 86%). TLC: R$_f$=0.32 (CHCl$_3$: 3% EtOH); $^1$H NMR (C$_6$D$_6$, 300 MHz) δ 4.23 (m, 1H), 4.14 (t, J=6.8 Hz, 1H), 3.80 (d, J=10 Hz, 1H), 3.67 (br. s, 1H), 3.17 (ddd, J=1.2, 4, 7.6 Hz, 1H), 3.01 (dd, J=3.6, 10.0 Hz, 1H), 2.79 (s, 3H), 2.27 (d, J=14.4 Hz, 1H), 2.22 (m, 1H), 2.12 (d, J=14.4 Hz, 1H), 1.50-1.40 (m, 2H); $^1$H NMR (CDCl$_3$, 500 MHz) δ 4.41 (t, J=4.4 Hz, 1H), 4.21 (dt, J=5.1, 10.1 Hz, 1H), 4.08 (d, J=10.3 Hz, 1H), 3.85 (dd, J=3.0, 7.3 Hz, 1H), 3.83 (d, J=10.3 Hz, 1H), 3.42 (s, 3H), 2.94-2.86 (m, 1H), 2.13 (d, J=14.5 Hz, 1H), 2.08 (dd, J=2.4, 15.1 Hz, 1H), 1.81 (ddd, J=5.3, 10.6, 14.5 Hz, 1H), 1.74 (ddd, J=5.3, 6.0, 15.0 Hz, 1H); $^{13}$C NMR (CDCl$_3$; 125 MHz) δ 86.0, 82.1, 73.6, 71.6, 57.4, 47.2, 42.0, 34.0.

Methyl 2-(((1R,4S)-4-((tert-butyldimethylsilyl)oxy)cyclopent-2-en-1-yl)oxy)acetate (10). To an ice-cold suspension of NaH (60% susp. oil, 170 mg, 4.2 mmol) in dry THF (2 mL) under argon was slowly added a solution of 2-bromoacetic acid (243 mg, 1.75 mmol) in dry THF (1.5 mL+1.5 mL rinse). The resulting mixture was stirred at room temperature for 30 min then cooled back down to 0° C. Desymmetrized meso-cyclopentenediol 6 (300 mg, 1.4 mmol) in dry DMF (5 mL) was slowly added over this solution and the reaction was stirred at room temperature for 36 h. Saturated aqueous $NH_4Cl$ solution, with an adjusted pH of 3 was added and the aqueous phase was successively extracted with EtOAc (4×). The combined organic phase was dried ($Na_2SO_4$), filtered, and evaporated in vacuo to give the corresponding crude carboxylic acid along with residual DMF. The acid was diluted with additional DMF (5 mL), the solution was cooled to 0° C. and $NaHCO_3$ (1.17 g) was added at once followed by MeI (14 mmol, 1.98 g, 871 µL). After stirring at room temperature for 24 h, saturated $NH_4Cl$ solution was added (5 mL), then water (10 mL), and the aqueous phase was successively extracted with $Et_2O$ (4×). The combined organic phase were dried ($Na_2SO_4$), filtered, and evaporated. The residue was purified by flash chromatography on silica gel using hexanes/EtOAc (20:1 then 15:1) to give methyl ester 10 as a colorless oil (214 mg, 53% over 2 steps). TLC: Rf=0.41 (hexanes/EtOAc=5:1); 1H NMR (CDCl3, 300 MHz) δ 5.92 (s, 2H), 4.63 (dd, J=4.8, 7.0 Hz, 1H), 4.53 (dd, J=5.1, 7.2 Hz, 1H), 4.10 (s, 2H), 3.74 (s, 3H), 2.64 (dt, J=7.2, 13.8 Hz, 1), 1.60 (dt, J=4.9, 13.7 Hz, 1H), 0.87 (s, 9H), 0.065 (s, 3H), 0.06 (s, 3H); 13C NMR (CDCl3, 75 MHz) δ 171.2, 138.4, 131.9, 82.4, 74.6, 64.7, 51.8, 40.5, 25.8, 18.0, −4.7.

(3R,3aR,5R,6aR)-5-((tert-butyldimethylsilyl)oxy) hexahydro-2H-cyclopenta[b]furan-3-ol (11). A solution of methyl ester 10 (87.2 mg, 0.304 mmol) in dry $CH_2Cl_2$ (8 mL) was cooled to −78° C. under argon. DIBAL-H (1M sol. in hexanes, 0.40 mL) was added slowly and the reaction mixture was stirred for 1 h at this temperature. The reaction was quenched by addition of MeOH (100 µL) and the mixture was warmed to rt. A pH 7 phosphate buffer (0.5M solution, 2 mL) was added. The aqueous phase was extracted with $CH_2Cl_2$ (3×) and the combined organic phase washed with brine, dried ($Na_2SO_4$), filtered, and evaporated in vacuo. The crude aldehyde solution was passed through a short plug of silica gel, initially deactivated with 1% $Et_3N$, using hexanes/EtOAc (5:1) as the eluent. After evaporation, the crude product was directly submitted to the next step. The residue was re-dissolved in dry benzene (degassed, 2 mL) under argon and the solution transferred into a sealable tube. ($nBu_3Sn)_2O$ (22.5 µL, 26.3 mg, 44 µmol), $Ph_2SiH_2$ (42 µL, 41.6 mg, 0.22 mmol), EtOH (45 µL), and AIBN (10 mg) were successively added. The sealed tube was placed with stirring in an oil bath at 80° C. for 6 h. After cooling to room temperature, the reaction mixture was diluted with $Et_2O$ (2 mL) and aqueous 0.5M HCl solution (2 mL) was added. After stirring at room temperature for 15 min, the aqueous phase was extracted with $Et_2O$ (3×). The combined organic phase was washed with saturated aqueous $NaHCO_3$ solution, brine, dried ($MgSO_4$), filtered, and evaporated. The residue was purified by flash chromatography on silica gel using hexanes/EtOAc (6:1 to 2:1) to afford the (R)-alcohol 11 (50 mg, 64% over 2 steps) as a white solid; 5 mg of the other 3-(S)-diastereoisomer was also isolated and only traces of 1,2 reduction product were observed. TLC: Rf=0.46 (hexanes/EtOAc=3:1); $[\alpha]_D^{20}$+22.3° (c 0.67, CHCl3); 1H NMR (CDCl3, 300 MHz) δ 4.69 (dt, J=3.8, 7.2 Hz, 1H), 4.19-4.02 (m, 3H), 3.72 (d, J=9.8 Hz, 1H), 2.48 (q, J=7.5 Hz, 1H), 2.13-1.96 (m, 2H), 1.70-1.55 (m, 2H), 1.47-1.25 (m, 1H), 0.86 (s, 9H), 0.03 (s, 6H); 13C NMR CDCl3, 75 MHz) δ 82.2, 78.3, 73.1, 72.7, 50.9, 42.4, 39.0, 25.8, 17.5, −4.8, −4.9.

(3S,3aR,5R,6aR)-3-Methylhexahydro-2H-cyclopenta[b]furan-5-ol (9e). To a solution of olefin 113 (29.7 mg, 0.12 mmol) in toluene (3 mL) was added Wilkinson's catalyst, $RhCl(PPh_3)_3$ (18 µmol, 17 mg). The resulting solution was then placed under a hydrogen atmosphere and stirred for 3 h. After dilution with additional toluene, the solution was filtered on a celite pad, and the pad was rinsed with toluene. Evaporation of the solvent and purification of the residue on silica gel using hexanes:EtOAc (100:1 then 50:1) as the eluent furnished the corresponding 3-(S)-methyl compound (29 mg, 97%). TLC: $R_f$=0.28 (hexanes/EtOAc=20:1); $[\alpha]_D^{20}$+22.7 (c 1.01, CHCl3); 1H NMR (CDCl3, 400 MHz) δ 4.43 (m, 1H), 4.03 (m, 1H), 3.81 (dd, J=7.4, 8.0 Hz, 1H), 3.42 (dd, J=8.0, 10.7 Hz, 1H), 2.43 (m, 1H), 2.32-2.18 (m, 2H), 1.72 (m, 1H), 1.51 (ddd, J=4.8, 8.6, 13.5 Hz, 1H), 1.44 (m, 1H), 0.95 (d, J=6.8 Hz, 3H), 0.88 (s, 9H), 0.05 (s, 6H); 13C NMR (CDCl3, 100 MHz) δ 82.6, 73.2, 71.6, 44.5, 43.2, 36.2, 34.7, 25.9, 18.2, 11.3, −4.7, −4.8; HRMS-CI (m/z): [M+H]+ calcd for $C_{14}H_{29}O_2Si$ 257.1937. found 257.1936. A solution of methyl-based ligand (28 mg, 0.1 mmol) in THF (2 mL) was treated with TBAF (1 M sol. in THF, 150 µL) and stirred at room temperature for 2.5 h. The reaction mixture was diluted with $Et_2O$ and filtered on a short silica pad. The solvent containing the alcohol was carefully reduced and essentially pure alcohol 9e was directly used to the next step without purification (>99%). TLC: $R_f$=0.26 (hexanes/EtOAc=1:1); 1H NMR (CDCl3, 400 MHz) δ 4.46 (dt, J=2.7, 5.5 Hz, 1H), 4.20 (m, 1H), 3.88 (t, J=7.8 Hz, 1H), 3.48 (t, J=9.2 Hz, 1H), 2.59-2.40 (m, 2H), 2.22 (d, J=6.9 Hz, 1H), 2.08 (dt, J=5.9, 14.1 Hz), 1.87 (ddd, J=6.0, 9.5, 13.7 Hz, 1H), 1.83 (m, 1H), 1.68-1.54 (m, 1H), 1.01 (d, J=6.8 Hz, 3H); 13C NMR (CDCl3, 100 MHz) δ 85.3, 73.8, 72.9, 46.3, 42.4, 36.5, 34.5, 12.7.

(3R,3aR,6aR)-3-Methyl-3,3a,6,6a-tetrahydro-2H-cyclopenta[b]furan-2-one (116). To a solution of lithium diisopropylamide, prepared by adding nBuLi (2.5 M sol. in hexanes, 1.36 mL, 3.39 mmol) to diisopropylamine (477 µL, 3.39 mmol) in THF (15 mL) at 0° C., was added a pre-cooled solution of known (3aS,6aR)-3,3a,6,6a-tetrahydro-2H-cyclopenta[b]furan-2-one (+)-115 (350 mg, 2.82 mmol) in THF (5 mL+3 mL rinse) at −78° C., dropwise. The reaction mixture was stirred at this temperature for 30 min, then methyl iodide (352 µL, 5.65 mmol) was added dropwise and the reaction mixture was stirred at −78° C. for 6 h. The reaction mixture was quenched with 2 M aqueous HCl. The aqueous phase was extracted with $Et_2O$ (×3). The combined organic layer was dried ($Na_2SO_4$), filtered, and concentrated under vacuum. The residue was purified by column chromatography on silica gel using hexanes/$Et_2O$ (5:1) to yield lactone 116 (369 mg, 95%) as a brown oil. TLC: $R_f$=0.54 (hexanes/EtOAc=2:1); $[\alpha]_D^{20}$+54.2 (c 1.0, CHCl3); 1H NMR (CDCl3, 400 MHz) δ 5.74 (m, 1H), 5.59 (m, 1H), 5.12 (t, J=5.6 Hz, 1H), 3.13 (dd, J=3.8, 1.8 Hz, 1H), 2.65 (m, 2H), 2.52 (q, J=7.6 Hz, 1H), 1.33 (d, J=7.6 Hz, 3H); 13C NMR (CDCl3, 100 MHz) δ 180.0, 130.9, 129.4, 81.3, 53.8, 39.9, 39.2, 17.4.

(3R,3aR,5R,6aR)-5-Hydroxy-3-methylhexahydro-2H-cyclopenta[b]furan-2-one (117). To a ice-cold yellow solution of $Hg(OAc)_2$ (1.45 g, 4.57 mmol) in THF:$H_2O$ (2.5:1 ratio, 23 mL) was added perchloric acid (~0.7 mL) until the solution became colorless. A solution of lactone 116 (350 mg, 2.54 mmol) in THF (7 mL) was then added at 0° C. and the reaction was stirred for 1 h. Additional $Hg(OAc)_2$ (646 mg, 2.03 mmol) similarly pretreated with perchloric acid in THF:$H_2O$ (2.5:1, 10 mL) was added and stirring was continued for 2 h at 0° C. The pH of the mixture was then adjusted to ~10 by addition of a 1M aqueous NaOH solution. Stirring was then continued for 1 h at room temperature. The solution was cooled to 0° C. and $NaBH_4$ (145 mg, 3.81 mmol) was added in small portions. After 1 h, the reaction mixture was acidified to pH=2 with concentrated HCl and stirring was continued for 1 h. The reaction solution was saturated with NaCl, and the aqueous phase extracted several times with EtOAc. The combined organic phase was dried (Na$_2$SO$_4$), filtered, and concentrated under vacuum. The residue was purified by column chromatography on silica gel using 2% MeOH in CH$_2$Cl$_2$ to yield alcohol 117 (252 mg, 64%) as a colorless oil. TLC: Rf=0.31 (CHCl3/MeOH=9/1); [α]$_D^{20}$+53.5 (c 1.0, CHCl3); 1H NMR (CDCl3, 400 MHz) δ 4.98 (dt, J=8.0, 14.9 Hz, 1H), 4.55 (m, 1H), 2.69 (qd, J=3.9, 7.6 Hz, 1H), 2.58 (m, 1H), 2.55 (m, 1H), 2.09 (d, J=15.0 Hz, 1H), 1.94 (m, 2H), 1.83 (m, 1H), 1.26 (d, J=7.6 Hz, 3H); 13C NMR (CDCl3, 100 MHz) δ 181.0, 83.8, 74.6, 51.2, 45.5, 43.9, 41.3, 18.4.

(3R,3aR,5R,6aR)-3-Methylhexahydro-2H-cyclopenta[b]furan-5-ol (9f). To a solution of lactone 117 (205 mg, 1.31 mmol) in CH$_2$Cl$_2$ (9 mL) was added DIBAL-H (1M sol. in CH$_2$Cl$_2$, 1.45 mL, 1.45 mmol) dropwise at −78° C. The reaction was stirred for 3 h then quenched with saturated Rochelle's salt solution. After stirring overnight at room temperature, the phases were separated and the aqueous phase was extracted with EtOAc (×3). The combined organic phase was dried (Na$_2$SO$_4$), filtered, and concentrated under reduced pressure. The residue was purified by column chromatography on silica gel using 2% MeOH in CH$_2$Cl$_2$ to yield the corresponding lactol (150 mg, 72%). To a solution of this lactol (143 mg, 0.9 mmol) in CH$_2$Cl$_2$ (9 mL) at −78° C. was added TiCl$_4$ (100 μL, 0.9 mmol) dropwise and the reaction was stirred for 20 min. Et$_3$SiH (289 μL, 1.81 mmol) was then added and the solution was stirred for an additional 1 h. The reaction was quenched with saturated NaHCO$_3$ solution once completion was reached as observed by TLC. The aqueous phase was extracted Et$_2$O, dried (Na$_2$SO$_4$), filtered, and concentrated under reduced pressure at 25° C. The residue was purified by column chromatography on silica gel using 2% MeOH in CH$_2$Cl$_2$ to yield alcohol 9f (122 mg, 95%) as a colorless oil. TLC: Rf=0.38 (CHCl3/MeOH=9/1); [α]$_D^{20}$+ 12.6 (c 1.0, CHCl3); 1H NMR (CDCl3, 400 MHz) δ 4.47 (t, J=5.7 Hz, 1H), 4.22 (m, 1H), 4.06 (dd, J=6.5, 8.7 Hz, 1H), 3.18 (t, J=8.4 Hz, 1H), 2.60 (d, J=7.2 Hz, 1H), 2.27-2.18 (m, 1H), 2.18-2.12 (m, 1H), 2.00 (dd, J=1.5, 16.2 Hz, 1H), 1.98-1.91 (m, 1H), 1.80 (dt, J=5.2, 14.6 Hz, 1H), 1.69 (ddd, J=2.3, 5.4, 13.9 Hz, 1H), 1.03 (d, J=6.7 Hz, 3H); 13C NMR (CDCl3, 100 MHz) δ 85.4, 75.1, 74.7, 50.3, 43.2, 41.6, 41.5, 17.6.

(3R,3aS,5R,6aR)-5-hydroxyhexahydro-2H-cyclopenta[b]furan-3-yl acetate (9c). Alcohol 11 (45 mg, 0.175 mmol) was diluted in CH$_2$Cl$_2$ (5 mL), and the solution cooled to 0° C. under argon. Et$_3$N (0.525 mmol, 53 mg, 75 μL) and DMAP (1 crystal) were added followed by acetic anhydride (25 μL, 0.23 mmol). The mixture was warmed to rt and stirred overnight. The solution was evaporated to dryness and purification of the residue by flash column chromatography on silica gel using hexanes/EtOAc (20:1) furnished the corresponding acetate derivative (38 mg, 73%). TLC: R$_f$=0.24 (hexanes/EtOAc=10:1); $^1$H NMR (CDCl$_3$, 300 MHz) δ 5.02 (d, J=3.8 Hz, 1H), 4.69 (dt, J=3.2, 7.2 Hz, 1H), 4.22 (dd, J=4.0, 10.4 Hz, 1H), 4.11 (m, 1H), 3.80 (d, J=10.4 Hz, 1H), 2.56 (m, 1H), 2.09-1.97 (m, 2H), 2.04 (s, 3H), 1.71 (m, 1H), 1.68-1.54 (m, 1H), 0.86 (s, 9H), 0.03 (s, 6H); $^{13}$C NMR (CDCl$_3$, 75 MHz) δ 170.8, 82.9, 81.2 72.8, 70.9, 48.5, 42.7, 39.2, 25.8, 21.2, 18.0, −4.9. The acetate (28 mg, 0.093 mmol) was diluted in THF (1.5 mL), TBAF (1M sol. THF, 200 μL, 0.2 mmol) was added at 0° C. and the mixture was stirred for 2.5 h while warming to 23° C. The solvent was evaporated and the residue purified by flash column chromatography on silica gel using hexanes/EtOAc (3:1 to 1:1) to give pure alcohol 9c as a colorless oil (17.5 mg, quant.). TLC: Rf=0.18 (EtOAc 100%); 1H NMR (CDCl3, 300 MHz) δ 5.51 (m, 1H), 4.70-4.62 (m, 1H), 4.32 (dd, J=5.0, 10.4 Hz, 1H), 4.28-4.20 (m, 1H), 3.71 (dd, J=3.2, 10.4 Hz, 1H), 2.65-2.56 (m, 1H), 2.30-2.13 (m, 2H), 2.06 (s, 9H), 1.99-1.88 (m, 1H), 1.77-1.68 (m, 1H); 13C NMR (CDCl3, 75 MHz) δ 170.8, 84.8, 81.1, 73.4, 71.9, 48.9, 41.9, 39.5, 21.1.

(3R,3aS,5R,6aR)-3-methoxyhexahydro-2H-cyclopenta[b]furan-5-ol (9d). A solution of alcohol 11 (30 mg, 0.116 mmol) in dry DMF (1 mL) was cooled to 0° C. under argon and NaH (60% suspension in oil, 15 mg, 0.348 mmol) was added at once. The mixture was warmed to r.t., stirred for 30 min then cooled again to 0° C. MeI (22 μL, 50 mg, 0.35 mmol) was added to the solution and the reaction was warmed to 23° C. and stirred for 3.5 h. Saturated aqueous NH4Cl solution was added and the aqueous phase was extracted with Et2O/hexanes (1:1). The combined organic phase was washed with brine, dried (MgSO$_4$), filtered, and evaporated in vacuo. The residue was purified by flash chromatography on silica gel using hexanes/EtOAc (10:1 then 81) to afford the corresponding TBS-protected methoxy compound (28.6 mg, 86%) as a clear oil. TLC: Rf=0.61 (hexanes/EtOAc=3:1); [α]t+20.6 (c 1.52, CHCl3); 1H NMR (CDCl3, 400 MHz) δ 4.63 (dt, J=3.6, 7.2 Hz, 1H), 4.11 (m, 1H), 4.05 (dd, J=4.1, 9.9 Hz, 1H), 3.81 (d, J=1.3, 9.9 Hz, 1H), 3.74 (m, 1H), 3.31 (s, 3H), 2.54 (td, J=7.7, 8.3 Hz, 1H), 2.10-1.96 (m, 2H), 1.70-1.60 (m, 1H), 1.47 (m, 1H), 0.87 (s, 9H), 0.04 (6H), 13C NMR (CDCl3, 75 MHz) δ 87.7, 82.5, 72.9, 70.3, 56.6, 47.4, 42.5, 39.5, 25.8, 18.0, −4.8, −4.9.

To an ice-cold solution of the above methoxy intermediate (27 mg, 0.1 mmol) in THF (2 mL) under argon was added TBAF (1M solution in THF, 0.2 mL, 0.2 mmol). The reaction was stirred for 1.5 h. The solvent was evaporated and the crude residue was purified by flash column chromatography on silica gel using hexanes/EtOAc (1:1) as the eluent to furnish alcohol 9d as a clear oil (13 mg, 82%). TLC: R$_f$=0.17 (hexanes/EtOAc=1:2); $^1$H NMR (CDCl3, 300 MHz) δ 4.63 (t, J=5.5 Hz, 1H), 4.26 (m, 1H), 4.20 (dd, J=5.3, 9.7 Hz, 1H), 3.89 (t, J=2.0, 4.8 Hz, 1H), 3.65 (dd, J=4.4, 9.7 Hz, 1H), 3.34 (s, 3H), 2.64-2.54 (m, 1H), 2.40 (br. s., 1H), 2.16 (ddd, J=5.5, 10.6, 14.3 Hz, 1H), 2.02 (dd, J=1.7, 14.7 Hz, 1H), 1.87 (dt, J=5.1, 14.7 Hz, 1H), 1.77-1.61 (m, 2H); 13C NMR (CDCl3, 75 MHz) δ 88.4, 85.1, 74.0, 71.9, 57.0, 48.4, 41.8, 40.2.

tert-Butyl(((1S,4R)-4-(1-ethoxy-2-iodopropoxy)cyclopent-2-en-1-yl)oxy)-dimethylsilane (12). To a solution of desymmetrized alcohol 6 (103 mg, 0.48 mmol) in CH$_2$Cl$_2$ (1 mL) under argon was added (Z)-1-ethoxyprop-1-ene (Evans, et al., J. Am. Chem. Soc. 2008, 130, 16295-16309) (65 mg, 0.75 mmol) followed by N-iodosuccinimide (115 mg, 0.5 mmol). The mixture was stirred at 0° C. for 12 h then quenched by addition of saturated aqueous Na$_2$SO$_3$ solution. The aqueous layer was extracted with CH$_2$Cl$_2$ (3×), the combined organic phase was dried (MgSO$_4$), filtered, then evaporated in vacuo. The residue was purified by column chromatography to furnish 12 as a ca. 1:1 mixture of diastereoisomeric iodoacetal (123 mg, 62%). Colorless oil. TLC: (SiO$_2$, hexanes/EtOAc=10:1, R$_f$=0.53); $^1$H NMR (CDCl$_3$, 300 MHz) δ 5.96-5.86 (m, 2H), 4.68-4.60 (m, 1H), 4.59-4.50 (m, 1H), 4.50 (dd, J=3.5, 5.6 Hz, 1H), 4.19-4.07 (m, 1H), 3.72-3.580 (m, 1H), 3.62-3.52 (m, 1H), 2.71 (dt, J=3.5, 7.2 Hz, 0.5H), 2.66 (dt, J=3.2, 7.2 Hz, 0.5H), 1.85 (d, J=7.0 Hz, 3H), 1.73-1.60 (m, 1H), 1.22 (t, J=7.0 Hz, 1.5H), 1.22 (t, J=7.0 Hz, 1.5 H), 0.88 (s, 9H), 0.08 (s, 3H), 0.07 (s, 3H); $^{13}$C NMR (CDCl$_3$, 75 MHz) δ 137.5, 133.1, 132.7, 104.6, 104.4, 80.2, 79.7, 74.7, 62.5, 42.2, 41.8, 27.4, 27.3, 25.8, 22.2, 18.1, 15.1, −4.6, −4.7.

Alternative Preparation of (3S,3aR,5R,6aR)-3-methyl-hexahydro-2H-cyclopenta[b]furan-5-ol (9e) and (3R,3aR,5R,6aR)-3-methylhexahydro-2H-cyclopenta[b]furan-5-ol (9f). Mixed acetal 12 (115 mg, 0.269 mmol) was diluted in degassed toluene (15 mL) under argon at room temperature. N-tributyltin hydride (142 µL, 154 mg, 0.53 mmol) was added followed by Et$_3$B (1 M solution in hexanes, 54 µL, 53.8 µmol). The solution was stirred at room temperature for 3 h. Saturated aqueous NH$_4$Cl solution was added, followed by water. After vigorous stirring, the phases were separated and the organic phase was extracted with CH$_2$Cl$_2$. The combined organic phase was dried (MgSO$_4$), filtered on a short pad of silica gel and evaporated. The resulting mixture, which revealed three spots on TLC, was quickly purified by column chromatography on silica gel using hexanes/EtOAc (30:1) and fractions collected for each isomers were combined. A mixture of 4 isomers (d.r.=1:1.7:2:2.7), as observed by $^1$H NMR, was isolated as a colorless oil (ca. 80 mg, >99%). TLC (3 spots): R$_f$=0.42, 0.41, 0.31 (hexanes/EtOAc=10:1); C—H acetal peaks observed by 1H NMR (500 MHz, CDCl$_3$) δ 4.90 (d, J=4.0 Hz, 0.14 H), 4.85 (d, J=5.0 Hz, 0.27 H), 4.77 (d, J=4.5 Hz, 0.35 H), 4.73 (d, J=1.5 Hz, 0.23 H). The mixture was diluted in CH$_2$Cl$_2$ (3 mL) and cooled to −40° C. under argon. Et$_3$SiH (185 µL, 134 mg, 1.15 mmol) was added followed by BF$_3$.OEt$_2$ (50 µL, 61 mg, 0.43 mmol), dropwise. The reaction was let stirring for 3 h while slowly warming to 0° C. The reaction was quenched by addition of saturated aqueous NaHCO$_3$ solution, the layers were separated and the resulting aqueous solution was extracted with CH$_2$Cl$_2$ (3×). The combined organic phase was dried (Na$_2$SO$_4$), filtered and evaporated under vacuum. The resulting mixture, which showed partial desilylation, was directly submitted to the next step. The residue (ca. 42 mg) was diluted in THF (1.5 mL) under argon at room temperature and TBAF (1 M sol. in THF, 574 µL, 0.574 mmol) was added. At completion, celite was introduced in the flask, and the solution diluted with pentane/CH$_2$Cl$_2$ (10:2; 12 mL). The resulting suspension was loaded and passed through a silica gel column, flushing with pentane: CH$_2$Cl$_2$:Et$_2$O (10:2:2) then CH$_2$Cl$_2$:Et$_2$O (1:1). The resulting mixture of isomers was collected and the solvent carefully evaporated under reduced pressure. The essentially pure mixture of isomeric alcohols was directly submitted to the next step with the synthesis of their respective mixed activated carbonates, 9e and 9f, ratio 3(S)-Me/3(R)-Me=0.7:1, stereochemistry confirmed by NOESY acquisition on the 3(S)-Me isomer. TLC: R$_f$=0.28, 0.26 (hexanes/EtOAc=1:1).

(3aR,5R,6aR)-5-((tert-Butyldimethylsilyl)oxy)tetrahydro-2H-cyclopenta[b]furan-3(3aH)-one O-methyl oxime (14). O-methyl hydroxylamine hydrochloride (1.6 mmol, 133 mg) was suspended in EtOH (3 mL) cooled to 0° C. then NaHCO$_3$ (137 mg) was added. After stirring for 10 min, a solution of ketone 7 (100 mg, 0.39 mmol) in EtOH (1 mL+1 mL rinse) was added to the mixture. After 2 h stirring at r.t., the solution was carefully concentrated, diluted with CH$_2$Cl$_2$, filtered on a silica pad, and the pad rinsed with CH$_2$Cl$_2$. The solution was concentrated and the residue was purified by column chromatography on silica gel using hexanes/EtOAc (8:1) as the eluent to give the corresponding oxime 14 (3:1 mixture of stereoisomers, 107 mg, 96%). TLC: R$_f$=0.40, 0.43 (hexanes/EtOAc=5:1); $^1$H NMR (CDCl$_3$, 400 MHz) δ 4.84-4.74 (m, 1+0.33 H), 4.60 (d, J=13.3 Hz, 0.33H), 4.58 (d, J=15.6 Hz, 1H); 4.43 (d, J=15.6 Hz, 1H), 4.30-4.25 (m, 1.33 H), 4.24-4.20 (m, 0.33H), 3.85 (s, 1H), 3.82 (s, 3H), 3.32 (m, 0.33H), 3.22 (m, 1H), 2.10-1.78 (m, 4+1.33 H), 0.86 (s, 12H), 0.04 (s, 3+1H), 0.03 (s, 3+1H); $^{13}$C NMR (CDCl$_3$, 75 MHz) δ 166.9, 165.2, 84.8, 84.4, 73.5, 73.3, 67.7, 66.7, 61.7, 44.1, 43.8, 43.3, 42.7, 42.5, 39.3, 25.8, 25.7; LRMS-EI (m/z): 285.40.

N-43S,3aR,5R,6aR)-5-hydroxyhexahydro-2H-cyclopenta[b]furan-3-yl)-acetamide (9g) and N-43R,3aR,5R,6aR)-5-hydroxyhexahydro-2H-cyclopenta[b]furan-3-yl)acetamide (9h). Oxime 19 (45 mg, 0.1 mmol) was diluted in 3 mL MeOH. Raney-Ni (0.16 g) and Pd/C (10% w/w, 9 mg) were added to the solution followed by saturated ammonia solution in MeOH (0.5 mL) and water (75 µL). The resulting suspension was vigorously stirred under hydrogen (80 psi) at room temperature for 12 h. The mixture was diluted with MeOH, filtered over a celite pad, and evaporated in vacuo to yield the crude amine, which was directly used in the subsequent step without purification. The resulting crude amine was re-dissolved in CH$_2$Cl$_2$ (4 mL). Et$_3$N (0.785 mmol, 80 mg, 110 µL), DMAP (2 mg) and Ac$_2$O (0.314 mmol, 32 mg, 30 µL) were successively added at 0° C. and the resulting solution was stirred at room temperature for 24 h at which point two isomeric products could be observed. Saturated NH$_4$Cl aq. solution was added, the two phases were separated, and the aqueous phase extracted with CH$_2$Cl$_2$ (3×). The combined organic phase was washed with brine, dried (Na$_2$SO$_4$), and evaporated in vacuo. Purification by column chromatography on silica gel using hexanes/EtOAc (2:1, 1:1 then 1:2) as the eluent provided the two isomeric amide intermediate (Major (3S)-isomer, 23 mg, oil; minor (3R)-isomer, 15 mg, white solid; 80% combined yield over 2 steps). Major (3S)-isomer: TLC: R$_f$=0.29 (hexanes:EtOAc=1:1); [α]$_D^{20}$+30.7° (c 1.16, CHCl$_3$); $^1$H NMR (CDCl$_3$, 400 MHz) δ 7.12 (br. d., J=8.4 Hz, 1H), 4.62 (m, 1H), 4.46 (t, J=7.2 Hz, 1H), 4.36 (m, 1H), 3.70 (dd, J=2.6, 9.3 Hz, 1H), 3.65 (dd, J=4.8, 9.3 Hz, 1H), 2.93 (m, 1H), 1.98 (s, 3H), 1.92 (m, 1H), 1.85 (dd, J=5.0, 6.7 Hz, 1H), 1.84-1.74 (m, 2H), 0.92 (s, 9H), 0.12 (s, 3H), 0.11 (s, 3H); $^{13}$C NMR (CDCl$_3$, 100 MHz) δ 169.4, 85.4, 75.0, 74.5, 51.2, 45.4, 42.3, 35.7, 26.1, 23.5, 18.5, −4.5, −4.6. Minor (3R)-isomer: TLC: R$_f$=0.16 (hexanes/EtOAc=1:1, Rf=0.16); [α]$_D^{20}$+17.1° (c 0.77, CHCl$_3$); $^1$H NMR (CDCl$_3$, 400 MHz) δ 5.82 (br.s., 1H), 4.60 (dt, J=4.0, 7.2 Hz, 1H), 4.23 (m, 1H), 4.15 (dd, J=4.3, 9.6 Hz, 1H), 4.06 (m, 1H), 3.63 (d, J=9.6 Hz, 1H), 2.42 (m, 1H), 2.17-2.01 (m, 2H), 1.95 (s, 3H), 1.64 (m, 1H), 1.51 (m, 1H), 0.87 (s, 9H), 0.04 (s, 6H); $^{13}$C NMR (CDCl$_3$, 100 MHz) δ 169.4, 82.0, 72.5, 70.6, 56.7, 49.0, 42.3, 39.8, 25.8, 23.3, 18.0, −4.9.

The TBS-protected (3S)-amide (17 mg, 0.057 mmol) was diluted in THF (1.5 mL), cooled to 0° C. under argon. TBAF (1 M sol. in THF, 100 µL) was added and the solution was stirred for 12 h at room temperature. The mixture was concentrated and purified on silica gel column chromatography using CH$_2$Cl$_2$/2% MeOH to 6% MeOH to give 9g (10 mg, 90%). TLC: R$_f$=0.XX (hexanes:EtOAc=, R$_f$=); [α]$_D^{20}$−23.3° (c 0.65, CHCl$_3$); $^1$H NMR (CDCl$_3$, 400 MHz) δ 7.62 (d, J=7.4 Hz, 1H), 4.47-4.37 (m, 2H), 3.76 (d, J=9.6 Hz, 1H), 3.57 (dd, J=4.3, 9.6 Hz, 1H), 3.00 (dt, J=8.7, 8.9 Hz, 1H), 2.56 (br. s., 1H), 2.05 (m, 1H), 1.97 (s, 3H), 1.92-1.81 (2H), 1.73 (ddd, J=4.6, 10.3, 15.0 Hz, 1H); $^{13}$C NMR (CDCl$_3$, 100 MHz) δ 169.7, 85.7, 75.6, 73.8, 51.5, 45.7, 42.1, 34.7, 30.9, 23.4; HRMS-EI (m/z): calcd for C$_9$H$_{15}$NO$_3$ 185.1052. found 185.1055. The same procedure was applied to the isomeric (3R)-amide (10 mg, 0.033 mmol). Purification of the crude compound by column chromatography on silica gel using CH$_2$Cl$_2$/3% MeOH then 6% MeOH provided alcohol 9h (6 mg, >99%) as a colorless oil. [α]$_D^{20}$+9.1° (c 0.38, CHCl$_3$); $^1$H NMR (CDCl$_3$, 400 MHz) δ 5.71 (br.s., 1H), 4.62 (dt, J=2.6, 6.0 Hz, 1H), 4.36-4.30 (m, 1H), 4.26 (dd, J=5.3, 9.4 Hz, 1H), 4.24 (m, 1H), 3.55 (dd, J=3.8, 9.4 Hz, 1H), 2.52-2.43 (m, 1H), 2.19 (m, 1H), 2.08 (br.s., 1H), 2.01 (m, 1H), 1.98 (s, 3H), 1.95-1.87 (m, 1H), 1.72 (dm, 1H); $^{13}$C NMR (CDCl$_3$, 100 MHz) δ 169.9, 84.0, 73.3, 71.7, 57.5, 49.6, 41.7, 40.2, 23.3.

N-((3S,3aR,5R,6aR)-5-hydroxyhexahydro-2H-cyclopenta[b]furan-3-yl)-methanesulfonamide (9i) and N-((3R,3aR,5R,6aR)-5-hydroxyhexahydro-2H-cyclo-penta[b]furan-3-yl)methanesulfonamide (9j). The same procedure for the synthesis of compounds 9i and 9j were used as for compounds 9g and 9h. Thus crude amine (43 mg, ca. 0.24 mmol) was re-dissolved in CH$_2$Cl$_2$ (2 mL). Et$_3$N (0.5 mmol, 50.6 mg, 70 μL) and MsCl (0.32 mmol, 37 mg, 30 μL) were successively added at 0° C. and the resulting solution was stirred at room temperature for 4 h. Sat. NH$_4$Cl solution was added, the two phases were separated and the aqueous phase extracted with CH$_2$Cl$_2$ (4×). The combined organic phase was washed with brine, dried (Na$_2$SO$_4$) and evaporated in vacuo. The residue was passed through a short column of silica gel flushing with EtOAc to furnish a mixture of the corresponding diastereoisomeric O-silylated N-mesylate intermediates (40 mg). The mixture was diluted in THF (1 mL) and TBAF (1M sol. in THF, 600 μL, 0.6 mmol) was added at once. The solution was stirred at room temperature for 2.5 h. The solvent was evaporated in vacuo and the residue purified by column chromatography on silica gel. Major isomer 9k: [α]$_D^{20}$ −9.6° (c 0.92, CHCl$_3$); $^1$H NMR (CDCl$_3$, 400 MHz) δ 6.75 (d, J=10.0 Hz, 1H), 4.45 (t, J=7.0 Hz, 1H), 4.42 (t, J=4.3 Hz, 1H), 4.07 (dddd, J=1.3, 4.4, 7.3, 11.6 Hz, 1H), 3.91 (dd, J=0.9, 9.6 Hz, 1H), 3.61 (dd, J=4.4, 9.6 Hz, 1H), 3.03 (m, 1H), 2.97 (s, 3H), 2.58 (s, 1H), 2.13 (d, J=15.0 Hz, 1H), 2.03 (dd, J=15.5 Hz, 1H), 1.85 (ddd, J=4.6, 6.4, 15.4 Hz, 1H), 1.79 (ddd, J=4.5, 10.2, 14.9 Hz, 1H); $^{13}$C NMR (CDCl$_3$, 100 Hz) δ 85.5, 75.3, 73.6, 56.2, 46.3, 42.1, 41.9, 34.9; Minor isomer 9l: $^1$H NMR (CDCl$_3$, 400 MHz) δ 4.70 (d, J=8.2 Hz, 1H), 4.64 (t, J=5.4 Hz, 1H), 4.31-4.25 (m, 2H), 3.53 (dd, J=5.7, 9.4 Hz, 1H), 3.00 (s, 3H), 2.10 (ddd, J=5.0, 9.8, 14.3 Hz, 1H), 2.05-1.80 (m, 3H).

(3R,3aS,5R,6aR)-5-hydroxyhexahydro-2H-cyclopenta[b]furan-3-yl dimethylcarbamate (9k). To a ice-cold solution of alcohol 11 (30 mg, 0.12 mmol) in CH$_2$Cl$_2$ (1 mL) under argon was added pyridine (25 μL, 23 mg, 0.29 mmol) followed by para-nitrophenylchloroformate (46 mg, 0.232 mmol) at once. The white suspension was stirred at this temperature until completion is reached (ca. 2 h). The reaction mixture was evaporated to dryness and the residue purified by column chromatography using hexanes:EtOAc to give mixed activated carbonate compound as a white solid. TLC: R$_f$=0.21 (hexanes/EtOAc=5:1); $^1$H NMR (CDCl$_3$, 400 MHz) δ 8.27 (d, J=9.2 Hz, 2H), 7.38 (d, J=9.2 Hz, 2H), 5.11 (d, J=3.9 Hz, 1H), 4.81 (dt, J=2.7, 7.2 Hz, 1H), 4.34 (dd, J=4.0, 10.8 Hz, 1H), 4.21-4.15 (m, 1H), 3.98 (d, J=10.8 Hz, 1H), 2.82-2.75 (m, 1H), 2.11-2.00 (m, 2H), 1.78-1.66 (m, 2H), 0.87 s, 6H), 0.05 (s, 6H); $^{13}$C NMR (CDCl$_3$, 100 MHz) δ 155.4, 152.2, 145.4, 125.3, 121.7, 86.5, 83.3, 72.8, 70.6, 48.6, 42.8, 39.3, 25.8, 18.0, −4.9, −5.0.

A solution of the mixed activated carbonate (20 mg, 0.47 mmol) in THF (2 mL) was cooled to −20° C. Et$_3$N (100 μL, excess) was added and a stream of Me$_2$NH gas was bubbled through the solution for 5 min. The solution was stirred at 0° C. for 1 h then concentrated under vacuum. The residue was purified by column chromatography using hexanes:EtOAc (6:1 to 4:1) to yield pure O-silylated carbamate (16 mg, 96%). TLC: Rf=0.25 (hexanes/EtOAc=5:1); 1H NMR (CDCl$_3$, 400 MHz) δ 4.97 (d, J=3.9 Hz, 1H), 4.69 (dt, J=3.2, 7.2 Hz, 1H), 4.23 (dd, J=4.1, 10.3 Hz, 1H), 4.11 (pentet, J=5.5 Hz, 1H), 3.85 (d, J=10.3 Hz, 1H), 2.90 (s, 3H), 2.89 (s, 3H), 2.60 (dt, J=7.1, 8.7 Hz, 1H), 2.09-2.00 (m, 2H), 1.69 (dt, J=3.7, 14.5 Hz, 1H), 1.65-1.57 (m, 1H), 0.87 (s, 9H), 0.04 (s, 6H); $^{13}$C NMR (CDCl$_3$, 100MHz) δ 156.3, 82.9, 82.0, 72.8, 71.3, 48.8, 42.7, 39.2, 36.3, 35.9, 25.8, 18.1, −5.0. To a solution of the above carbamate (16 mg, 0.049 mmol) in THF (1 mL) was added tetrabutylammonium fluoride (1M in THF, 90 μL, 0.09 mmol) at 0° C. under argon. The reaction was stirred for 5 h then the solution was evaporated to dryness. The residue was purified by column chromatography on silica gel using hexanes/EtOAc (3:1, 1:1 then 1:2) to afford pure alcohol 9k (10.4 mg, >99%). TLC: R$_f$=0.20 (hexanes/EtOAc=1:2); [α]$_D^{20}$+30.5 (c 0.98, CHCl$_3$); $^1$H NMR (CDCl$_3$, 400 MHz) δ 5.06 (m, 1H), 4.67 (dt, J=1.5, 5.4 Hz, 1H), 4.33 (dd, J=5.0, 10.3 Hz, 1H), 4.28-4.22 (m, 1H), 3.75 (dd, J=3.1, 10.3 Hz, 1H), 2.90 (s, 3H), 2.89 (s, 3H), 2.67-2.59 (m, 1H), 2.33 (br. s., 1H), 2.22 (ddd, J=5.7, 10.6, 14.5 Hz, 1H), 2.01 (dd, J=1.8, 14.7 Hz, 1H), 1.92 (dt, J=5.2, 14.7 Hz, 1H), 1.76-1.73 (m, 1H), 1.73-1.69 (m, 1H); $^{13}$C NMR (CDCl$_3$, 100 MHz) δ 156.0, 84.8, 81.8, 73.5, 72.4, 49.3, 41.9, 39.5, 36.3, 35.9.

Synthesis of activated mixed carbonates:

(3aS,5R,6aR)-3-oxohexahydro-2H-cyclopenta[b]furan-5-yl 4-nitrophenyl carbonate (19a). To a solution of ketone 8 (20 mg, 0.14 mmol) in CH$_2$Cl$_2$ (1 mL) was added pyridine (30 μL). The solution was cooled to 0° C. under argon and 4-nitrophenyl chloroformate (42 mg, 0.21 mmol) was added at once. A white suspension appears. The solution was stirred at this temperature and slowly warmed to r.t., until all starting material disappeared. The reaction mixture was evaporated to dryness and the residue purified by column chromatography on silica gel using hexanes/EtOAc (3:1 then 2:1) as eluent to furnish pure mixed carbonate 19a (47 mg, 92%) as a white solid. TLC: R$_f$=0.25 (hexanes/EtOAc=2:1); $^1$H NMR (CDCl$_3$, 400 MHz) δ 8.27 (d, J=9.2 Hz, 2H), 7.34 (d, J=9.2 Hz, 2H), 5.23 (t, J=4.2 Hz, 1H), 5.13 (d, J=6.9 Hz, 1H), 4.20 (d, J=17.1 Hz, 1H), 4.06 (d, J=17.1 Hz, 1H), 2.99 (m, 1H), 2.48 (m, 2H), 2.22-2.08 (m, 2H); $^{13}$C NMR (CDCl$_3$, 100 MHz) δ 216.8, 155.3, 151.5, 145.4, 125.3, 121.9, 82.4, 81.0, 70.6, 48.5, 41.2, 37.1.

(3S,3aS,5R,6aR)-3-Methoxyhexahydro-2H-cyclopenta[b]furan-5-yl (4-Nitrophenyl) Carbonate (15b). The title compound was obtained from 9b in 82% yield as described for 9a after purification by column chromatography on silica gel using hexanes/EtOAc (3:1 to 2:1) as the eluent (white solid). TLC: R$_f$=0.25 (hexanes/EtOAc=2:1); $^1$H NMR (CDCl$_3$, 300 MHz) δ 8.27 (d, J=9.2 Hz, 2H), 7.38 (d, J=9.2 Hz, 2H), 5.15 (tt, J=4.5, 6.2 Hz, 1H), 4.56 (dt, J=2.8, 6.1 Hz, 1H), 4.04 (dt, J=6.3, 7.5 Hz, 1H), 3.87 (AB, dd, J=5.2, 9.1 Hz, 1H), 3.86 (AB, dd, J=6.6, 9.1 Hz, 1H), 3.34 (s, 3H), 2.83 (m, 1H), 2.38-2.02 (m, 4H); $^{13}$C NMR (CDCl$_3$, 75 MHz) δ 155.6, 152.1, 145.2, 125.2, 121.8, 83.7, 81.4, 77.2, 70.3, 57.9, 44.2, 39.6; 30.2.

(3R,3aS,5R,6aR)-5-((4-nitrophenoxy)carbonyloxy) hexahydro-2H-cyclopenta[b]furan-3-yl benzoate (215c). The title compound was obtained from 209c as described for 9a in 85% yield after purification by column chromatography on silica gel using hexanes/EtOAc (6:1 then 4:1). TLC: R$_f$=0.26 (hexanes/EtOAc=3:1); $^1$H NMR (CDCl$_3$, 400 MHz) δ 8.29 (d, J=9.2 Hz, 2H), 8.05 (d, J=7.2 Hz, 2H), 7.60 (t, J=7.2 Hz, 1H), 7.46 (t, J=7.6 Hz, 2H), 7.40 (d, J=9.2 Hz, 2H), 5.37 (2H, m), 5.21 (m, 1H), 4.86 (t, J=6.0 Hz, 1H), 4.40 (dd, J=4.8, 10.4 Hz, 1H), 3.99 (2.4, 10.4 Hz, 1H), 2.90 (m, 1H), 2.44 (ddd, J=6.0, 10.4, 14.8 Hz, 1H), 2.39 (d, J=15.6 Hz, 1H), 2.19 (dt, J=5.6, 15.6 Hz, 1H), 2.20-2.05 (m, 1H); $^{13}$C NMR (CDCl$_3$, 100 MHz) δ 166.2, 155.5, 151.9, 145.4, 133.3, 129.7, 129.6, 128.4, 125.3, 122.8, 83.3, 81.1, 77.1, 71.8, 49.1, 39.6, 36.0.

(3R,3aS,5R,6aR)-5-((4-Nitrophenoxy)carbonyloxy) hexahydro-2H-cyclopenta[b]furan-3-yl Acetate (15c). The title compound was obtained from 9c in 96% yield as described for 9a after purification by column chromatography on silica gel using hexanes/EtOAc (6:1 then 4:1) as the eluent (white solid). TLC: R$_f$=0.26 (hexanes/EtOAc=3:1); $^1$H NMR (CDCl$_3$, 300 MHz) δ 8.27 (d, J=9.1 Hz, 2H), 7.37 (d, J=9.1 Hz, 2H), 5.20-5.12 (m, 1H), 5.12-5.08 (m, 1H), 4.76 (m, J=2.0, 6.0 Hz, 1H), 4.27 (d, J=4.6, 10.4 Hz, 1H), 3.80 (dd, J=2.5, 10.4 Hz, 1H), 2.79-2.70 (m, 1H), 2.37 (ddd, J=6.0, 10.2, 15.0 Hz, 1H), 2.29-2.19 (m, 1H), 2.15 (dt, J=5.6, 15.6 Hz, 1H), 2.07 (s, 3H), 2.02-1.92 (m, 1H); $^{13}$C NMR (CDCl$_3$, 75 MHz) δ 170.7, 155.4, 151.9, 145.3, 125.3, 121.8, 83.2, 81.0, 80.5, 71.7, 48.8, 39.6, 35.9, 21.1.

(3R,3aS,5R,6aR)-3-methoxyhexahydro-2H-cyclopenta [b]furan-5-yl (4-nitro-phenyl) carbonate (15d). The title was obtained from 9d as described for 9a in 93% yield after purification by column chromatography on silica gel using hexanes/EtOAc (6:1 to 4:1) as the eluent. TLC: R$_f$=0.54 (hexanes/EtOAc=3:1); $^1$H NMR (CDCl$_3$, 400 MHz) δ 8.27 (d, J=9.2 Hz, 2H), 7.37 (d, J=9.2 Hz, 2H), 5.19-5.12 (m, 1H), 4.74-4.67 (m, 1H), 4.13 (dd, J=5.4, 5.5 Hz, 1H), 3.84-3.78 (m, 2H), 3.35 (s, 3H), 2.75-2.68 (m, 1H), 2.36 (ddd, J=6.1, 10.0, 14.8 Hz, 1H), 2.25-2.11 (m, 2H), 1.82 (dddd, J=1.2, 3.8, 5.5, 14.7 Hz, 1H); $^{13}$C NMR (CDCl$_3$, 100 MHz) δ 155.5, 151.9, 145.3, 125.3, 121.8, 87.5, 83.0, 81.3, 71.3, 56.9, 48.2, 39.4, 36.2.

(3S,3aR,5R,6aR)-3-methylhexahydro-2H-cyclopenta[b] furan-5-yl 4-nitro-phenyl carbonate (15e). The title compound was obtained as described for 9a from a crude mixture of 9e and 9f and separated from its diastereoisomer 15f by column chromatography on silica gel using hexanes/EtOAc (10:1 then 7:1). TLC: R$_f$=0.27 (hexanes:EtOAc=3:1); $^1$H NMR (CDCl$_3$, 300 MHz) δ 8.27 (d, J=9.0 Hz, 2H), 7.37 (d, J=9.0 Hz, 2H), 5.09 (m, 1H), 4.57 (dt, J=2.8, 6.2 Hz, 1H), 3.93 (t, J=8.1 Hz, 1H), 5.51 (dd, J=8.1, 10.4, 1H), 2.65 (m, 1H), 2.46 (m, 1H), 2.38 (m, 1H), 2.11 (m, 1H), 2.02 (ddd, J=2.7, 5.5, 14.8 Hz, 1H), 1.81 (m, 1H), 1.02 (d, J=6.9 Hz, 1H); $^{13}$C NMR (CDCl$_3$, 75 MHz) δ 155.5, 152.0, 145.3, 126.2, 125.3, 121.8, 115.5, 83.4, 80.8, 72.3, 45.8, 39.7, 36.5, 31.0, 11.8.

Alternative Preparation of (3S,3aR,5R,6aR)-3-Methylhexahydro-2H-cyclopenta[b]furan-5-yl (4-Nitrophenyl) Carbonate (15e). The title compound was obtained from 9e in 83% yield as described for 9a after purification by column chromatography on silica gel using hexanes/EtOAc (10:1 then 7:1) as the eluent (white solid). TLC: R$_f$=0.25 (hexanes:EtOAc=3:1); $^1$H NMR (CDCl$_3$, 300 MHz) δ 8.27 (d, J=9.0 Hz, 2H), 7.37 (d, J=9.0 Hz, 2H), 5.09 (m, 1H), 4.57 (dt, J=2.8, 6.2 Hz, 1H), 3.93 (t, J=8.1 Hz, 1H), 3.51 (dd, J=8.1, 10.4, 1H), 2.65 (m, 1H), 2.46 (m, 1H), 2.38 (m, 1H), 2.11 (m, 1H), 2.02 (ddd, J=2.7, 5.5, 14.8 Hz, 1H), 1.81 (m, 1H), 1.02 (d, J=6.9 Hz, 3H); $^{13}$C NMR (CDCl$_3$, 75 MHz) δ 155.5, 152.0, 145.3, 125.3, 121.8, 83.4, 80.8, 72.3, 45.8, 39.7, 36.5, 31.0, 11.8.

(3R,3aR,5R,6aR)-3-methylhexahydro-2H-cyclopenta[b] furan-5-yl (4-nitro-phenyl) carbonate (15f). The title was obtained as described for 9a from the crude mixture 9e and 9f following separation of the two resulting diastereoisomers by column chromatography on silica gel using hexanes/EtOAc (10:1 then 7:1) as the eluent. TLC: R$_f$=0.29 (hexanes/EtOAc=3:1); $^1$H NMR (CDCl$_3$, 300 MHz) δ 8.27 (d, J=9.2 Hz, 2H), 7.37 (d, J=9.2 Hz, 2H), 5.22-5.14 (m, 1H), 4.64 (dt, J=1.7, 6.6 Hz, 1H), 4.13 (dd, J=6.3, 8.5 Hz, 1H), 3.37 (dd, J=7.2, 8.6 Hz, 1H), 2.41-2.31 (m, 1H), 2.29-2.06 (m, 4H), 1.97-1.87 (m, 1H), 1.08 (d, J=6.8 Hz, 3H); $^{13}$C NMR (CDCl$_3$, 75 MHz) δ 155.5, 152.0, 145.3, 125.3, 121.8, 83.7, 82.2, 74.9, 50.5, 41.9, 39.5, 37.3, 29.7, 17.5.

Alternative Preparation of (3R,3aR,5R,6aR)-3-Methylhexahydro-2H-cyclopenta[b]furan-5-yl (4-Nitrophenyl) Carbonate (15f). The title compound was obtained from 9f in 50% yield as described for 9a following column chromatography on silica gel using hexanes/EtOAc (10:1 then 7:1). TLC: R$_f$=0.29 (hexanes/EtOAc=3:1); [α]$_D^{20}$+40.6 (c 1.0, CHCl3); 1H NMR (CDCl3, 400 MHz) δ 8.26 (d, J=9.3 Hz, 2H), 7.37 (d, J=9.3 Hz, 2H), 5.19-5.12 (m, 1H), 4.57 (dt, J=2.0, 6.8 Hz, 1H), 4.07 (dd, J=6.3, 8.6 Hz, 1H), 3.31 (dd, J=7.1, 8.6 Hz, 1H), 2.35-2.25 (m, 1H), 2.23-2.17 (m, 2H), 2.17-2.07 (m, 2H), 1.88 (ddd, J=3.8, 5.3, 14.5 Hz, 1H), 1.05 (d, J=6.8 Hz, 3H); 13C NMR (CDCl3, 100 MHz) δ 155.6, 151.9, 145.2, 125.2, 121.8, 83.3, 82.2, 74.9, 50.4, 41.8, 39.5, 37.3, 17.5.

(3S,3aR,5R,6aR)-3-acetamidohexahydro-2H-cyclopenta [b]furan-5-yl 4-nitrophenyl carbonate (15g). The title compound was obtained from 9g as described for 9a in 79% yield after purification by column chromatography on silica gel using hexanes/EtOAc (1:1 to 1:6) then 100% EtOAc as the eluent. $^1$H NMR (CDCl$_3$, 400 MHz) δ 8.29 (d, J=8.8 Hz, 2H), 7.39 (d, J=8.8 Hz, 2H), 6.30 (br. d., J=9.2 Hz, 1H), 5.27 (m, 1H), 4.71 (m, 1H), 4.50 (t, J=6.8 Hz, 1H), 3.81 (d, J=9.6 Hz, 1H), 3.71 (dd, J=4.8, 9.6 Hz, 1H), 3.10 (m, 1H), 2.36 (d, J=16.4 Hz, 1H), 2.12-1.98 (m, 3H), 2.04 (s, 3H); $^{13}$C NMR (CDCl$_3$, 100 MHz) δ 169.5, 155.2, 151.3, 145.5, 125.4, 121.7, 84.7, 82.7, 74.3, 52.0, 45.9, 39.0, 32.7, 23.4;

(3R,3aR,5R,6aR)-3-acetamidohexahydro-2H-cyclopenta [b]furan-5-yl 4-nitrophenyl carbonate (15h). The title compound was obtained from 9h as described for 9a in 71% yield after purification by column chromatography on silica gel using hexanes/EtOAc (1:2 to 1:6) then 100% EtOAc. TLC: R$_f$=0.20 (100% EtOAc); $^1$H NMR (CDCl$_3$, 400 MHz) δ 8.28 (d, J=9.2 Hz, 2H), 7.38 (d, J=9.2 Hz, 2H), 5.74 (br. s., J=6.8 Hz, 1H), 5.13 (m, 1H), 4.70 (m, 1H), 4.34 (m, 1H), 4.20 (dd, J=4.8, 9.6 Hz, 1H), 3.62 (dd, J=3.2, 9.6 Hz, 1H), 2.61 (m, 1H), 2.38 (ddd, J=6.0, 10.0, 14.8 Hz, 1H), 2.18 (m, 2H), 2.02-1.90 (m, 2H), 1.99 (s, 3H); $^{13}$C NMR (CDCl$_3$, 100 MHz) δ 169.7, 155.4, 151.9, 145.3, 125.3, 121.8, 82.8, 80.8, 71.6, 57.1, 49.7, 39.4, 36.6, 23.3;

(3S,3aR,5R,6aR)-3-(Methylsulfonamido)hexahydro-2H-cyclopenta[b]furan-5-yl (4-nitrophenyl) carbonate (15i). The title compound was obtained from 9i as described for 9a in 83% yield after purification by column chromatography on silica gel using hexanes/EtOAc (2:1 to 1:3). TLC: R$_f$=0.22 (hexanes:EtOAc=1:2); $^1$H NMR(C$_6$D$_6$, 500 MHz) δ 7.68 (d, J=7.1 Hz, 2H), 6.91 (d, J=7.1 Hz, 2H), 4.93-4.86 (m, 2H), 3.89 (t, J=6.5 Hz, 1H), 3.75-3.67 (m, 1H), 3.51 (dd, J=3.0, 9.5 Hz, 1H), 3.24 (dd, J=5.3, 9.5 Hz, 1H), 2.34-2.23 (m, 1H), 2.21 (s, 3H), 2.14 (dd, J=1.9, 15.6 Hz, 1H), 2.08 (dd, 15.6 Hz), 1.44-1.31 (m, 2H); $^{13}$C NMR(C$_6$D$_6$, 125 MHz) δ 155.3, 152.0, 145.8, 125.3, 122.1, 84.6, 82.3, 73.4, 56.6, 46.4, 40.9, 38.9, 32.7.

(3R,3aR,5R,6aR)-3-(Methylsulfonamido)hexahydro-2H-cyclopenta[b]furan-5-yl (4-nitrophenyl) carbonate (15j). The title compound was obtained from 9j as described for 9a in 86% yield after purification by column chromatography on silica gel using hexanes/EtOAc (2:1 to 1:3). TLC: R$_f$=0.37 (hexanes:EtOAc=1:4); $^1$H NMR (CDCl$_3$, 400 MHz) δ 8.28 (d, J=9.2 Hz, 2H), 7.38 (d, J=9.2 Hz, 2H), 5.18 (m, 1H), 4.72 (dt, J=1.7, 6.8 Hz, 1H), 4.55 (d, J=8.6 Hz, 1H), 4.23 (dd, J=5.5, 9.5 Hz, 1H), 3.96-3.90 (m, 1H), 3.60 (dd, J=5.1, 9.5 Hz, 1H), 3.00 (s, 3H), 2.74-2.66 (m, 1H), 2.32 (ddd, J=5.8, 9.6, 15.0 Hz, 1H), 2.28-2.20 (m, 1H), 2.17 (dt, J=5.8, 15.6 Hz, 1H), 2.08-2.00 (m, 1H); $^{13}$C NMR (CDCl$_3$, 100 MHz) δ 155.4, 151.8, 145.4, 125.3, 121.9, 83.0, 81.2, 72.2, 60.6, 50.3, 41.8, 39.4, 36.5.

(3R,3aS,5R,6aR)-5-4(4-nitrophenoxy)carbonyl)oxy) hexahydro-2H-cyclopenta[b]furan-3-yl dimethylcarbamate (15k). The title was obtained from 9k as described for 9a in 93% yield following column chromatography purification on silica gel using hexanes/EtOAc (2:1) as the eluent. TLC: R$_f$=0.25 (hexanes/EtOAc=1:1); $^1$H NMR (CDCl$_3$, 400 MHz)

δ 8.27 (d, J=9.2 Hz, 2H), 7.37 (d, J=9.2 Hz, 2H), 5.19-5.13 (m, 1H), 5.04 (m, 1H), 4.75 (dt, J=1.8, 6.0 Hz, 1H), 4.26 (dd, J=4.6, 10.3 Hz, 1H), 3.84 (dd, J=2.5, 10.3 Hz, 1H), 2.91 (s, 3H), 2.90 (s, 3H), 2.81-2.74 (m, 1H), 2.37 (ddd, J=6.1, 10.2, 15.0 Hz, 1H), 2.22 (d, J=15.4 Hz, 1H), 2.15 (dt, J=5.8, 15.4 Hz, 1H), 1.98 (dddd, J=1.6, 3.4, 5.4, 15.0 Hz, 1H); $^{13}$C NMR (CDCl$_3$, 100 MHz) δ 156.0, 155.5, 151.9, 143.3, 125.2, 121.8, 83.2, 81.3, 81.1, 72.0, 49.2, 39.6, 36.4, 35.9.

General Method for the Synthesis of HIV-Protease Inhibitors:

(3aS,5R,6aR)-3-oxohexahydro-2H-cyclopenta[b]furan-5-yl (2S,3R)-3-hydroxy-4-(N-isobutyl-4-methoxyphenylsulfonamido)-1-phenylbutan-2-ylcarbamate (19a). A solution of isostere 22 (82 mg, 0.16 mmol) was dissolved in a 2:1 mixture CH$_2$Cl$_2$/TFA and stirred at r.t. for 2 h. The solution was then evaporated and dried under vacuo. The residue was re-dissolved in CH$_3$CN (1 mL) and the solution cooled down to 0° C. under argon. Et$_3$N (100 µL) was added followed by a solution of activated carbonate 15a (40 mg, 0.13 mmol) in THF (1 mL). The solution was stirred for 36 h and the solution evaporated in vacuo. The residue was purified by flash chromatography on silica gel using hexanes/EtOAc (3:1 to 1.5:1) as the eluent to furnish inhibitor 19a (46 mg, 61%) as a white solid. TLC: R$_f$=0.23 (hexanes/EtOAc=1:1); $^1$H NMR (CDCl$_3$, 400 MHz) δ 7.71 (d, J=8.8 Hz, 2H), 7.34-7.26 (m, 2H), 7.25-7.19 (m, 3H), 6.98 (d, J=8.8 Hz, 2H), 5.03 (t, J=7.2 Hz, 1H), 4.99 (m, 1H), 4.70 (d, J=8.8 Hz, 1H), 3.97 (m, 2H), 3.87 (s, 3H), 3.84-3.70 (m, 3H), 3.09 (dd, J=8.0, 15.2 Hz, 1H), 3.04-2.82 (m, 3H), 2.79 (dd, J=6.8, 13.2 Hz, 1H), 2.24-2.12 (m, 2H), 2.06-1.94 (m, 2H), 1.81 (m, 1H) 0.90 (d, J=6.4 Hz, 1H), 0.86 (d, J=6.4 Hz, 1H); $^1$H NMR (CDCl$_3$, 500 MHz) δ 7.70 (d, J=8.8 Hz, 2H), 7.34-7.28 (m, 2H), 7.25-7.19 (m, 3H), 6.98 (d, J=8.8 Hz, 2H), 5.03 (t, J=6.9 Hz, 1H), 4.99 (m, 1H), 4.71 (d, J=8.7 Hz, 1H), 3.97 (s, 2H), 3.87 (s, 3H), 3.89-3.85 (m, 1H), 3.83-3.70 (m, 2H), 3.09 (dd, J=8.0, 15.2 Hz, 1H), 3.00 (dd, J=3.0, 15.1 Hz, 1H), 2.99-2.89 (m, 3H), 2.89-2.82 (m, 1H), 2.79 (dd, J=6.8, 13.4 Hz, 1H), 2.24-2.12 (m, 2H), 2.06-1.94 (m, 2H), 1.81 (m, 1H), 0.90 (d, J=6.4 Hz, 3H), 0.86 (d, J=6.4 Hz, 3H); $^{13}$C NMR (CDCl$_3$, 125 MHz) δ 216.2, 163.0, 155.4, 137.5, 129.8, 129.6, 129.5, 128.5, 126.6, 114.3, 82.9, 76.3, 72.2, 70.6, 58.8, 55.6, 55.1, 53.7, 48.7, 41.2, 37.3, 35.1, 27.3, 20.1, 19.9; HRMS-ESI (m/z): [M+Na]$^+$ calcd for C$_{29}$H$_{38}$N$_2$O$_8$SNa 597.2247. found 597.2251.

(3S,3aR,5R,6aR)-3-hydroxyhexahydro-2H-cyclopenta[b]furan-5-yl (2S,3R)-3-hydroxy-4-(4-(methoxy)-N-isobutylphenylsulfonamido)-1-phenylbutan-2-ylcarbamate (22). A solution of keto-inhibitor 19a (10 mg, 17 µmol) in EtOH was cooled to −25° C. and NaBH4 (6 mg) was added at once. The solution was stirred for 30 min then saturated NH$_4$Cl aq. solution was added. The aqueous phase was extracted with EtOAc (4×), the combined organic layer was dried, filtered and evaporated. The residue was purified by column chromatography on silica gel using hexanes:EtOAc (2:1, 1:1, then 1:2) as the eluent to afford the desired inhibitor 22 (8 mg, 80%). TLC: R$_f$=0.22 (hexanes/EtOAc=1:2); $^1$H NMR (CDCl$_3$, 400 MHz) δ 7.70 (d, J=8.8 Hz, 1H), 7.32-7.17 (m, 5H), 6.98 (d, J=8.8 Hz, 1H), 5.07 (m, 1H), 4.96 (d, J=7.2 Hz, 1H), 4.38 (, t, J=6.8 Hz, 1H), 4.22 (m, 1H), 3.87 (s, 3H), 3.88-3.74 (m, 3H), 3.54 (dd, J=3.2, 9.6 Hz, 1H), 3.10 (dd, J=7.8, 15.0 Hz, 1H), 3.05-2.82 (m, 4H), 2.78 (dd, J=6.8, 13.6 Hz, 1H), 2.42 (dd, J=10.8 Hz, 1H), 2.18-2.04 (m, 2H), 1.94-1.76 (m, 3H); TLC: R$_f$=0.39 (hexanes/EtOAc=1:5); $^1$H NMR (CDCl$_3$, 500 MHz) δ 7.70 (d, J=8.8 Hz, 2H), 7.32-7.19 (m, 5H), 6.97 (d, J=8.8 Hz, 2H), 5.07 (m, 1H), 4.89 (d, J=7.2 Hz, 1H), 4.38 (t, J=6.8 Hz, 1H), 4.21 (m, 1H), 3.87 (s, 3H), 3.88-3.74 (m, 4H), 3.54 (dd, J=3.2, 9.6 Hz, 1H), 3.10 (dd, J=7.8, 15.0 Hz, 1H), 3.05-2.82 (m, 5H), 2.78 (dd, J=6.8, 13.4 Hz, 1H), 2.42 (br.s, 1H), 2.18-2.04 (m, 2H), 1.94-1.76 (m, 3H), 0.90 (d, J=6.6 Hz, 3H), 0.86 (d, J=6.6 Hz, 3H); $^{13}$C NMR (CDCl$_3$, 125 MHz) δ 163.0, 155.3, 137.6, 129.9, 129.6, 129.5, 128.6, 126.5, 114.3, 84.9, 78.1, 76.3, 73.0, 72.2, 58.7, 55.6, 55.3, 53.7, 47.3, 39.1, 35.4, 31.3, 27.2, 20.1, 19.9; HRMS-ESI (m/z): [M+Na$^+$] calcd for C$_{30}$H$_{42}$N$_2$O$_2$SNa 597.2610. found 597.2608.

(3aS,5R,6aR)-3-oxohexahydro-2H-cyclopenta[b]furan-5-yl (2S,3R)-3-hydroxy-4-(4-(hydroxymethyl)-N-isobutylphenylsulfonamido)-1-phenylbutan-2-yl-carbamate (21). The title compound was obtained from 15a and isostere 18 as described for 19a. Column chromatography on silica gel using hexanes/EtOAc; $^1$H NMR (CDCl$_3$, 500 MHz) δ 7.77 (d, J=8.2 Hz, 2H), 7.47 (d, J=8.2 Hz, 2H), 7.34-7.28 (m, 2H), 7.25-7.20 (m, 3H), 5.18 (s, 2H), (3S,3aS,5R,6aR)-3-Methoxyhexahydro-2H-cyclopenta [b]furan-5-yl [(2S,3R)-3-Hydroxy-4-(N-iso-butyl-4-methoxyphenylsulfonamido)-1-phenylbutan-2-yl]carbamate (19b). The title compound was obtained in 73% yield from 15b and 16 as described for 19a following column chromatography on silica gel using hexanes/EtOAc (1:1) as the eluent. White solid. TLC: R$_f$=0.21 (hexanes/EtOAc=1:1); $^1$H NMR (CDCl$_3$, 500 MHz) δ 7.70 (d, J=8.9 Hz, 2H), 7.33-7.19 (m, 5H), 6.97 (d, J=8.9 Hz, 2H), 4.97-4.90 (m, 1H), 4.78 (d, J=7.5 Hz, 1H), 4.47-4.42 (m, 1H), 3.99 (q, J=6.9 Hz, 1H), 3.87 (s, 3H), 3.88-3.82 (m, 2H), 3.81-3.76 (m, 2H), 3.70 (dd, J=6.9, 9.0 Hz, 1H), 3.30 (s, 3H), 3.14-3.06 (dd, J=7.8, 14.9 Hz, 1H), 3.04-2.88 (m, 4H), 2.78 (dd, J=6.7, 13.4 Hz, 1H), 2.70 (m, 1H), 2.14 (m, 1H), 1.93 (dd, J=6.3, 8.6 Hz, 2H), 1.86-1.76 (m, 2H), 0.90 (d, J=6.6 Hz, 3H), 0.86 (d, J=6.6 Hz, 3H); $^{13}$C NMR (CDCl$_3$, 125 MHz) δ 163.0, 156.3, 137.5, 129.9, 129.6, 129.5, 128.5, 126.5, 114.3, 83.5, 81.3, 76.3, 72.3, 70.0, 58.7, 57.8, 55.6, 54.9, 53.7, 43.8, 39.5, 35.5, 30.4, 27.2, 20.1, 19.9; HRMS-ESI (m/z): [M+H]$^+$ calcd for C$_{30}$H$_{43}$N$_2$O$_8$S 591.2740. found 591.2742.

(3R,3aS,5R,6aR)-5-((((2S,3R)-3-hydroxy-4-(N-isobutyl-4-methoxyphenyl-sulfonamido)-1-phenylbutan-2-yl)carbamoyl)oxy)hexahydro-2H-cyclopenta[b]furan-3-yl acetate (19c). The title compound was obtained from 15c as described for 19a after purification by column chromatography on silica gel using hexanes/EtOAc (3:1 to 1:1) in 84% yield (white solid). TLC: R$_f$=0.23 (hexanes/EtOAc=1:2); $^1$H NMR (CDCl$_3$, 300 MHz) δ 7.71 (d, J=8.9 Hz, 2H), 7.34-7.19 (m, 5H), 6.97 (d, J=8.9 Hz, 2H), 4.91 (m, 1H), 4.88 (m, 1H), 4.75 (d, J=8.2 Hz, 1H), 4.67 (m, 1H), 3.98 (dd, J=4.1, 10.4 Hz, 1H), 3.87 (s, 3H), 3.85-3.77 (m, 3H), 3.73 (dd, J=1.5, 10.4 Hz, 1H), 3.19-2.92 (m, 4H), 2.90-2.72 (m, 2H), 2.67-2.55 (m, 1H), 2.23-2.09 (m, 1H), 2.06 (s, 3H), 2.04-1.76 (m, 3H), 1.54-1.43 (m, 1H), 0.91 (d, J=6.6 Hz, 3H), 0.87 (d, J=6.6 Hz, 3H); $^{13}$C NMR (CDCl$_3$, 75 MHz) δ 170.6, 163.0, 156.0, 137.6, 129.8, 129.5, 128.5, 126.6, 114.3, 83.5, 80.6, 76.1, 72.6, 71.6, 58.8, 55.6, 54.9, 53.7, 48.5, 39.6, 36.2, 35.7, 27.2, 21.1, 20.1, 19.9

((3R,3aS,5R,6aR)-3-Methoxyhexahydro-2H-cyclopenta [b]furan-5-yl [(2S,3R)-3-Hydroxy-4-(N-iso-butyl-4-methoxyphenylsulfonamido)-1-phenylbutan-2-yl]-carbamate (19d). The title compound was obtained in 57% yield from 15d and 16 as described for 19a following purification by column chromatography on silica gel using hexanes/EtOAc (2:1 to 1:1) as the eluent. White solid. TLC: R$_f$=0.34 (hexanes/EtOAc=1:2); $^1$H NMR (CDCl$_3$, 500 MHz) δ 7.71 (d, J=8.8 Hz, 2H), 7.33-7.25 (m, 2H), 7.26-7.20 (m, 3H), 6.98 (d, J=8.8 Hz, 2H), 4.89 (m, 1H), 4.78 (d, J=8.3 Hz, 1H), 4.61 (t, J=5.7 Hz, 1H), 3.93-3.85 (m, 1H), 3.88 (s, 3H), 3.85-3.79 (m, 2H), 3.73 (d, J=2.7, 9.8 Hz, 1H), 3.60 (m, 1H), 3.31 (s, 3H), 3.13 (dd, J=8.3, 15.2 Hz, 1H), 3.10-3.00 (m, 2H), 2.95 (dd, J=8.4, 13.4 Hz, 1H), 2.88-2.77 (m, 1H), 2.80 (dd, J=7.0, 13.3 Hz, 1H), 2.62-2.53 (m, 1H), 2.19-2.09 (m, 1H), 1.99 (dt, J=6.0, 15.1 Hz, 1H), 1.92 (m, 1H), 1.90-1.78 (m, 2H), 1.47-1.38 (m, 1H), 0.92 (d, J=6.6 Hz, 3H), 0.88 (d, J=6.6 Hz, 3H); $^{13}$C NMR (CDCl$_3$, 125 MHz) δ 163.0, 156.1, 137.7, 129.9, 129.5, 128.5, 126.5, 114.3, 87.6, 83.3, 76.5, 72.7, 71.1, 58.8, 56.7, 55.6, 54.9, 53.7, 48.0, 39.5, 36.6, 35.8, 27.2, 20.1, 19.9; HRMS-ESI (m/z): [M+Na]$^+$ calcd for C$_{30}$H$_{42}$N$_2$O$_8$SNa 613.2560. found 613.2555.

(3S,3aR,5R,6aR)-3-Methylhexahydro-2H-cyclopenta[b]furan-5-yl [(2S,3R)-3-Hydroxy-4-(N-iso-butyl-4-methoxyphenylsulfonamido)-1-phenylbutan-2-yl]carbamate (19e). The title compound was obtained from 15e and 16 in 78% yield as described for 19a following purification by column chromatography on silica gel using hexanes/EtOAc (3:1 to 2:1) as the eluent. White solid. TLC: R$_f$=0.32 (hexanes/EtOAc=1:1); $^1$H NMR (CDCl$_3$, 300 MHz) δ 7.71 (d, J=8.9 Hz, 2H), 7.34-7.19 (m, 5H), 6.98 (d, J=8.9 Hz, 2H), 4.84 (m, 1H), 4.75 (d, J=8.2 Hz, 1H), 4.49-4.40 (m, 1H), 3.87 (s, 3H), 3.86-3.76 (m, 4H), 3.32 (dd, J=8.3, 10.5 Hz, 1H), 3.11 (dd, J=7.8, 15.1 Hz, 1H), 3.06-2.84 (m, 4H), 2.79 (dd, J=6.7, 13.4 Hz, 1H), 2.54-2.45 (m, 1H), 2.40-2.31 (m, 1H), 2.18 (dt, J=6.5, 14.8 Hz, 1H), 1.90-1.77 (m, 2H), 1.74-1.66 (m, 1H), 1.50-1.40 (m, 1H), 0.91 (d, J=6.8 Hz, 3H), 0.90 (d, J=6.6 Hz, 3H), 0.86 (d, J=6.6 Hz, 3H); $^{13}$C NMR (CDCl$_3$, 75 MHz) δ 162.7, 156.3, 137.6, 129.8, 129.5, 128.5, 126.5, 114.3, 83.5, 76.0, 72.6, 72.2, 58.7, 55.6, 54.9, 53.7, 45.6, 39.8, 36.4, 35.6, 31.3, 27.2, 20.1, 19.8, 11.8. LRMS-ESI (m/z): [M+H]+575.

(3R,3aR,5R,6aR)-3-Methylhexahydro-2H-cyclopenta[b]furan-5-yl [(2S,3R)-3-Hydroxy-4-(N-isobutyl-4-methoxyphenylsulfonamido)-1-phenylbutan-2-yl]carbamate (19f). The title compound was obtained from 15f and 16 in 96% yield as described for 19a following purification by column chromatography on silica gel using hexanes/EtOAc (5:1) as the eluent. Yield 38 mg of a white solid (96%). TLC: Rf=0.50 (hexanes/EtOAc=1:1); [α]$_D^{20}$+24.5 (c 1.0, CHCl$_3$); 1H NMR (CDCl3, 400 MHz) δ 7.70 (d, J=8.8 Hz, 2H), 7.30-7.16 (m, 5H), 6.96 (d, J=8.8 Hz, 2H), 4.88 (m, 1H), 4.80 (d, J=7.1 Hz, 1H), 4.46 (m, 1H), 3.91 (dd, J=6.1, 8.5 Hz, 1H), 3.86 (s, 3H), 3.84 (m, 1H), 3.80 (m, 3H), 3.22 (dd, J=7.5, 14.8 Hz, 1H), 3.15-2.99 (m, 3H), 2.94 (dd, J=8.2, 13.4 Hz, 1H), 2.87-2.75 (m, 2H), 2.14 (m, 1H), 2.00-1.77 (m, 6H), 1.50 (d, J=12.3 Hz, 1H), 0.98 (d, J=6.6 Hz, 3H), 0.90 (d, J=6.6 Hz, 3H), 0.85 (d, J=6.6 Hz, 3H); 13C NMR (CDCl3, 100 MHz) δ 162.9, 156.2, 137.7, 129.8, 129.4, 128.4, 126.4, 114.3, 83.7, 77.2, 74.7, 72.5, 58.7, 55.6, 54.8, 53.7, 50.2, 41.8, 39.4, 37.7, 35.7, 27.2, 20.1, 19.8, 17.6. LRMS-ESI (m/z): [M+H]+575, [M+Na]+597.

(3S,3aR,5R,6aR)-3-(Dimethylamino)hexahydro-2H-cyclopenta[b]furan-5-yl [(2S,3R)-3-Hydroxy-4-(N-iso-butyl-4-methoxyphenylsulfonamido)-1-phenylbutan-2-yl]-carbamate (24c). To a solution of AcOH (~15 µL) in dichloromethane (1 mL), a slow stream of Me$_2$NH gas was bubbled briefly at 0° C. for 5 min. After flushing the flask with argon, a solution of ketone inhibitor 19a (13 mg, 0.02 mmol) in dichloroethane (0.5 mL) was added over at 0° C. and after 15 min, NaBH(OAc)$_3$ (10 mg, 0.05 mmol) was added. The resulting solution was warmed to room temperature. After 24 h, another 10 mg portion of NaBH(OAc)$_3$ was added and the solution stirred for 48 h. The reaction was quenched by addition of saturated aqueous NaHCO$_3$ solution adjusting the pH to 10 with 1M NaOH solution. The aqueous phase was extracted multiple times with EtOAc. The combined organic phase was dried (Na$_2$SO$_4$), filtered and evaporated under reduced pressure. The residue was purified by column chromatography on silica gel using Ethanol (0.5 to 2%) in CHCl$_3$ to furnish the corresponding dimethylamine inhibitor 24c (11.3 mg, 82%) as a white solid. TLC: Rf=0.35 (CHCl$_3$/8% EtOH); 1H NMR (CDCl3, 500 MHz) δ 7.70 (d, J=8.9 Hz, 2H), 7.32-7.26 (m, 2H), 7.25-7.19 (m, 3H), 6.97 (d, J=8.9 Hz, 2H), 4.92 (m, 1H), 4.86 (m, 1H), 4.55 (m, 1H), 3.90-3.85 (m, 1H), 3.87 (s, 3H), 3.83-3.75 (m, 2H) 3.70-3.63 (m, 1H), 3.30-3.20 (m, 1H), 3.10 (dd, J=3.14-3.06, 1H), 3.04-2.88 (m, 4H), 2.79 (dd, J=6.9, 13.4 Hz, 1H), 2.64-2.55 (m, 1H), 2.23-2.18 (m, 1H), 2.24 (br.s., 6H), 2.18-2.10 (m, 1H), 2.06-1.97 (m, 1H), 1.88-1.75 (m, 2H), 0.90 (d, J=6.6 Hz, 3H), 0.85 (d, J=6.6 Hz, 3H); 13C NMR (CDCl3, 125 MHz) δ 163.0, 156.4, 137.6, 130.0, 129.6, 129.5, 128.5, 126.5, 114.3, 83.8, 77.2, 76.0, 72.3, 69.4, 58.7, 55.6, 55.0, 53.7, 45.4, 45.3, 40.1, 35.5, 31.4, 27.2, 20.1, 19.9; LRMS-ESI (m/z): [M+H]$^+$ 604.

(3R,3aR,5R,6aR)-3-Hydroxyhexahydro-2H-cyclopenta[b]furan-5-yl [(2S,3R)-4-(4-Amino-N-iso-butylphenylsulfonamido)-3-hydroxy-1-phenylbutan-2-yl]-carbamate (26). The acetyl intermediate was first synthesized in 63% yield by coupling of 15c with 17 as described for 19a followed by purification by column chromatography on silica gel using CHCl$_3$/0.25% to 1.5% EtOH as the eluent. White solid. TLC: R$_f$=0.44 (hexanes/EtOAc=1:3); $^1$H NMR (CDCl$_3$, 500 MHz) δ 7.54 (d, J=8.7 Hz, 2H), 7.32-7.27 (m, 2H), 7.25-7.19 (m, 3H), 6.67 (d, J=8.7 Hz, 2H), 4.94 (m, 1H), 4.90-4.85 (m, 1H), 4.75 (d, J=8.7 Hz, 1H), 4.66 (t, J=5.4 Hz, 1H), 4.16 (br.s, 2H), 3.99 (dd, J=4.1, 10.4 Hz, 1H), 3.88-3.77 (m, 3H), 3.74 (d, J=10.3 Hz, 1H), 3.11 (dd, J=8.5, 15.1 Hz, 1H), 3.05 (dd, J=4.0, 14.1 Hz, 1H), 2.98 (dd, J=1.5, 15.2 Hz, 1H), 2.93 (dd, J=8.4, 13.2 Hz, 1H), 2.84 (dd, J=8.8, 13.9 Hz, 1H), 2.77 (dd, J=6.7, 13.3 Hz, 1H), 2.64-2.56 (m, 1H), 2.20-2.12 (m, 1H), 2.07 (s, 3H), 2.00 (dt, J=6.1, 15.2 Hz, 1H), 1.95-1.88 (m, 1H), 1.81 (m, 1H), 1.51-1.44 (m, 1H), 0.91 (d, J=6.6 Hz, 3H), 0.87 (d, J=6.6 Hz, 3H); $^{13}$C NMR (CDCl$_3$, 125 MHz) δ 170.6, 155.9, 150.6, 137.7, 129.5, 128.5, 126.5, 126.2, 114.1, 83.5, 80.6, 76.0, 72.6, 71.5, 58.9, 54.9, 53.8, 48.5, 39.6, 36.2, 35.7, 27.3, 21.1, 20.2, 19.9. The title compound was obtained from the above acetate intermediate in 88% yield as described for 25 following purification by column chromatography on silica gel using a gradient, 1% to 5% EtOH in CHCl$_3$, as the eluent. White solid. TLC: R$_f$=0.4 (CHCl$_3$/10% EtOH); $^1$H NMR (CDCl$_3$, 500 MHz) δ 7.55 (d, J=8.7 Hz, 2H), 7.31-7.26 (m, 2H), 7.24-7.19 (m, 3H), 6.67 (d, J=8.7 Hz, 2H), 4.89-4.83 (m, 1H), 4.79 (d, J=8.9 Hz, 1H), 4.69 (t, J=5.4 Hz, 1H), 4.16 (br.s, 2H), 4.01 (m, 1H), 3.88 (dd, J=3.7, 9.9 Hz, 1H), 3.87-3.76 (m, 3H), 3.65 (dd, J=1.4, 9.8 Hz, 1H), 3.14-3.04 (m, 2H), 2.99 (dd, J=2.9, 15.1 Hz, 1H), 2.92 (dd, J=8.3, 13.3 Hz, 1H), 2.81 (dd, J=9.1, 14.0 Hz, 1H), 2.78 (dd, J=6.8, 13.3 Hz, 1H), 2.54-2.47 (m, 1H), 2.11 (ddd, J=6.2, 10.2, 14.6 Hz, 1H), 2.00 (dt, J=6.1, 15.1 Hz, 1H), 1.93-1.85 (m, 1H), 1.85-1.76 (m, 2H), 1.35 (m, 1H), 0.91 (d, J=6.6 Hz, 3H), 0.87 (d, J=6.6 Hz, 3H); $^{13}$C NMR (CDCl$_3$, 125 MHz) δ 156.0, 150.7, 137.8, 129.5, 128.4, 126.4, 126.2, 114.1, 83.1, 78.3, 76.2, 73.7, 72.7, 58.9, 54.8, 53.8, 51.3, 39.5, 36.0, 35.8, 27.3, 20.2, 19.9; HRMS-ESI (m/z): [M+H]$^+$ calcd for C$_{28}$H$_{39}$N$_3$O$_7$S 584.2406. found 584.2398.

((3R,3aR,5R,6aR)-3-Hydroxyhexahydro-2H-cyclopenta[b]furan-5-yl [(2S,3R)-3-Hydroxy-4-(N-iso-butyl-4-methoxyphenylsulfonamido)-1-phenylbutan-2-yl]-carbamate (25). The acetyl intermediate was first synthesized in 84% yield by coupling of 15c with 16 as described for 19a followed by purification by column chromatography on silica gel using hexanes/EtOAc (3:1 to 1:1) as the eluent. White solid. TLC: R$_f$=0.23 (hexanes/EtOAc=1:2); $^1$H NMR (CDCl$_3$, 300 MHz) δ 7.71 (d, J=8.9 Hz, 2H), 7.34-7.19 (m, 5H), 6.97 (d, J=8.9 Hz, 2H), 4.91 (m, 1H), 4.88 (m, 1H), 4.75 (d, J=8.2 Hz, 1H), 4.67 (m, 1H), 3.98 (dd, J=4.1, 10.4 Hz, 1H), 3.87 (s, 3H), 3.85-3.77 (m, 3H), 3.73 (dd, J=1.5, 10.4 Hz, 1H), 3.19-2.92 (m, 4H), 2.90-2.72 (m, 2H), 2.67-2.55 (m, 1H), 2.23-2.09 (m, 1H), 2.06 (s, 3H), 2.04-1.76 (m, 3H), 1.50-1.43 (m, 1H), 0.91 (d, J=6.6 Hz, 3H), 0.87 (d, J=6.6 Hz, 3H); $^{13}$C NMR (CDCl$_3$, 75 MHz) δ 170.6, 163.0, 156.0, 137.6, 129.8, 129.5, 128.5, 126.6, 114.3, 83.5, 80.6, 76.1, 72.6, 71.6, 58.8, 55.6, 54.9, 53.7, 48.5, 39.6, 36.2, 35.7, 27.2, 21.1, 20.1, 19.9.

The acetate intermediate (18 mg, 0.029 mmol) was diluted in MeOH (1.5 mL) at 0° C. K$_2$CO$_3$ (5 mg, 0.04 mmol) was added and the solution was stirred for 6 h. Saturated aqueous NH$_4$Cl solution (1 mL) and the solvent was reduced under vacuum. The aqueous phase was diluted and extracted with EtOAc (×4). The combined organic phase was dried (MgSO$_4$), filtered, and evaporated. The residue was purified by column chromatography on silica gel using chloroform/0.5% to 3% EtOH as the eluent to provide inhibitor 25 (15.9 mg, 94%) as a white solid. TLC: R$_f$=0.26 (hexanes/EtOAc=1:5); $^1$H NMR (CDCl$_3$, 500 MHz) δ 7.71 (d, J=8.9 Hz, 2H), 7.33-7.25 (m, 2H), 7.24-7.19 (m, 3H), 6.98 (d, J=8.9 Hz, 2H), 4.86 (m, 1H), 4.81 (d, J=8.3 Hz, 1H), 4.69 (t, J=5.4 Hz, 1H), 4.01 (m, 1H), 3.91-3.76 (m, 4H), 3.87 (s, 3H), 3.64 (dd, J=2.0, 9.7 Hz, 1H), 3.12 (dd, J=8.2, 15.1 Hz, 1H), 3.11-3.05 (m, 1H), 3.03 (dd, J=2.7, 15.2 Hz, 1H), 2.95 (dd, J=8.3, 13.4 Hz, 1H), 2.85-2.75 (m, 2H), 2.52 (m, 1H), 2.12 (ddd, J=6.1, 10.0, 14.7 Hz, 1H), 1.99 (dt, J=6.1, 15.0 Hz, 1H), 1.93-1.79 (m, 3H), 1.35 (m, 1H), 0.91 (d, J=6.6 Hz, 3H), 0.87 (d, J=6.6 Hz, 3H); $^{13}$C NMR (CDCl$_3$, 125 MHz) δ 163.0, 156.0, 137.8, 129.8, 129.5, 128.4, 126.4, 114.3, 83.1, 78.3, 76.3, 73.8, 72.7, 58.8, 55.6, 54.8, 53.7, 51.3, 39.5, 36.1, 35.8, 27.2, 20.1, 19.9; HRMS-ESI (m/z): [M+H]$^+$ calcd for C$_{29}$H$_{41}$N$_2$O$_8$S 577.2584. found 577.2572.

(3S,3aR,5R,6aR)-3-Hydroxyhexahydro-2H-cyclopenta[b]furan-5-yl [(2S,3R)-4-(4-Amino-N-isobutylphenylsulfonamido)-3-hydroxy-1-phenylbutan-2-yl]carbamate (123). The ketone intermediate was first synthesized from the coupling of 15a with isostere 17 as described for 19a after stirring 48 h at r.t. in a CH$_2$Cl$_2$/THF (1:1) mixture. Purification of the crude compound by column chromatography on silica gel using Chloroform with 1% to 3% EtOH as the eluent afforded the corresponding ketone inhibitor (60%, white solid). TLC: R$_f$=0.18 (Chloroform/3% EtOH); $^1$H NMR (CDCl$_3$, 500 MHz) δ 7.54 (d, J=8.6 Hz, 2H), 7.34-7.28 (m, 2H), 7.25-7.18 (m, 3H), 6.68 (d, J=8.6 Hz, 2H), 5.02 (t, J=6.9 Hz, 1H), 4.99 (m, 1H), 4.68 (d, J=8.8 Hz, 1H), 4.14 (br. s, 2H), 3.98 (s, 2H), 3.91 (m, 1H), 3.84-3.72 (m, 2H), 3.08 (dd, J=8.4, 15.1 Hz, 1H), 3.00-2.83 (m, 5H), 2.76 (dd, J=8.7, 13.4 Hz, 1H), 2.22-2.15 (m, 2H), 2.05-1.97 (m, 2H), 1.80 (m, 1H), 0.90 (d, J=6.6 Hz, 3H), 0.86 (d, J=6.6 Hz, 3H); $^{13}$C NMR (CDCl$_3$, 125 MHz) δ 216.9, 155.4, 150.6, 137.5, 129.6, 129.5, 128.5, 126.5, 126.3, 114.1, 82.9, 76.3, 72.2, 70.6, 58.9, 55.0, 53.8, 48.7, 41.2, 37.3, 35.2, 27.3, 20.2, 19.9; HRMS-ESI (m/z): [M+Na]$^+$ calcd for C$_{28}$H$_{37}$N$_3$O$_7$SNa 582.2250. found 582.2246. The title compound was obtained in 82% yield by reduction of the above ketone intermediate as described for 22, followed by column chromatography on silica gel using hexanes/EtOAc (1:2 to 1:5) as the eluent. Off-white solid. TLC: R$_f$=0.12 (hexanes/EtOAc=1:2); $^1$H NMR (CDCl$_3$, 500 MHz) δ 7.54 (d, J=8.8 Hz, 2H), 7.34-7.18 (m, 5H), 6.68 (d, J=8.8 Hz, 2H), 5.07 (m, 1H), 4.87 (d, J=7.2 Hz, 1H), 4.38 (t, J=6.8 Hz, 1H), 4.24-4.19 (m, 1H), 4.14 (s, 2H), 3.86 (br.s, 1H), 3.85-3.75 (m, 3H), 3.55 (dd, J=3.6, 9.6 Hz, 1H), 3.10 (dd, J=8.2, 15.0 Hz, 1H), 3.04-2.79 (m, 5H), 2.76 (dd, J=6.8, 13.2 Hz, 1H), 2.37 (d, J=11.6 Hz, 1H), 2.10 (t, J=14.4 Hz, 2H), 1.94-1.75 (m, 3H), 0.90 (d, J=6.8 Hz, 3H), 0.86 (d, J=6.4 Hz, 3H); $^{13}$C NMR (CDCl$_3$, 125 MHz) δ 155.3, 150.6, 137.6, 129.6, 129.5, 128.5, 126.5, 126.4, 114.1, 84.9, 78.0, 70.3, 73.0, 72.2, 58.8, 55.2, 53.7, 47.3, 39.1, 35.5, 31.3, 27.3, 20.2, 19.9; HRMS-ESI (m/z): [M+Na]$^+$ calcd for C$_{28}$H$_{39}$N$_3$O$_7$SNa 584.2406. found 584.2410.

(3S,3aR,5R,6aR)-3-Hydroxyhexahydro-2H-cyclopenta[b]furan-5-yl {(2S,3R)-3-Hydroxy-4-[4-(hydroxymethyl)-N-iso-butylphenylsulfonamido]-1-phenylbutan-2-yl}carbamate (23). The ketone intermediate was first synthesized from the coupling of 15a with isostere 18 as described for 19a. Purification of the crude compound by column chromatography on silica gel using hexanes/EtOAc (2:1 to 1:2) as the eluent afforded the corresponding ketone inhibitor in 49% yield as a white solid. TLC: R$_f$=0.38 (hexanes/EtOAc=1:3); $^1$H NMR (CDCl$_3$, 500 MHz) δ 7.76 (d, J=8.2 Hz, 2H), 7.51 (d, J=8.2 Hz, 2H), 7.34-7.28 (m, 2H), 7.25-7.20 (m, 3H), 5.02 (t, J=6.9 Hz, 1H), 4.96 (m, 1H), 4.79 (s, 2H), 4.67 (d, J=8.4 Hz, 1H), 3.98-3.93 (m, 2H), 3.84-3.75 (m, 2H), 3.75-3.67 (m, 1H), 3.10 (dd, J=8.2, 15.1 Hz, 1H), 3.07-2.80 (m, 5H), 2.83 (dd, J=6.9, 13.5 Hz, 1H), 2.23-2.15 (m, 2H), 2.04-1.96 (m, 2H), 1.88-1.76 (m, 1H), 0.90 (dd, J=6.6 Hz, 3H), 0.87 (d, J=6.6 Hz, 3H). The title compound was obtained in 83% yield by reduction of the above ketone intermediate as described for 22, followed by column chromatography on silica gel using hexanes/EtOAc (1:1 to 1:3 then 100% EtOAc) as the eluent. White solid. TLC: R$_f$=0.23 (hexanes/EtOAc=1:3); $^1$H NMR (CDCl$_3$, 400 MHz) δ 7.76 (d, J=8.2 Hz, 2H), 7.51 (d, J=8.2 Hz, 2H), 7.34-7.27 (m, 2H), 7.24-7.20 (m, 3H), 5.06 (m, 1H), 4.82 (d, J=7.8 Hz, 1H), 4.76 (s, 2H), 4.38 (t, J=7.0 Hz, 1H), 4.21 (m, 1H), 3.85-3.68 (m, 4H), 3.55 (dd, J=3.5, 9.8 Hz, 1H), 3.11 (dd, J=8.3, 15.1 Hz, 1H), 3.05-2.79 (m, 6H), 2.38 (d, J=8.3 Hz, 1H), 2.15-1.99 (m, 2H), 1.94-1.80 (m, 3H), 0.91 (d, J=6.6 Hz, 3H), 0.87 (d, J=6.6 Hz, 3H); HRMS-ESI (m/z): [M+Na]$^+$ calcd for C$_{29}$H$_{40}$N$_2$O$_8$SNa 599.2403. found 599.2401.

(3S,3aR,5R,6aR)-3-acetamidohexahydro-2H-cyclopenta[b]furan-5-yl (2S,3R)-3-hydroxy-4-(N-isobutyl-4-methoxyphenylsulfonamido)-1-phenylbutan-2-yl-carbamate (19g). The compound was obtained from 15g as described for 19a after purification by column chromatography on silica gel using CHCl$_3$/5% MeOH as the eluent. White solid TLC: R$_f$=0.36 (CHCl$_3$/5% MeOH).

(3'R,3'aR,5'R,6'aR)-3-acetamidohexahydro-2H-cyclopenta[b]furan-5-yl (2S,3R)-3-hydroxy-4-(N-isobutyl-4-methoxyphenylsulfonamido)-1-phenylbutan-2-yl-carbamate (19h). Purified by column chromatography on silica gel using CHCl₃/5% MeOH as the eluent, off-white solid. TLC: R_f=0.24 (CHCl₃/5% MeOH); ¹H NMR (CDCl₃, 500 MHz) δ 7.71 (d, J=8.7 Hz, 1H), 7.34-7.18 (m, 5H), 6.98 (d, J=8.7 Hz, 1H), 4.86 (m, 1H), 4.77 (d, J=8.4 Hz, 1H), 4.58 (t, J=6.0 Hz, 1H), 3.96-3.91 (m, 2H), 3.87 (s, 3H), 3.82 (m, 3H), 3.67 (s, 3H), 3.55 (m, 1H), 3.12 (dd, J=8.2, 15.0 Hz, 1H), 3.09-2.92 (m, 3H), 2.90-2.81 (m, 1H), 2.79 (dd, J=6.8, 13.6 Hz, 1H), 2.47 (m, 1H), 2.18-2.12 (m, 1H), 2.04-1.96 (m, 1H), 1.92-1.85 (m, 1H), 1.82 (m, 1H), 1.48 (m, 1H), 0.92 (d, J=6.0 Hz, 1H), 0.87 (d, J=6.0 Hz, 1H); ¹³C NMR (CDCl₃, 125 MHz) δ 163.0, 156.3, 156.0, 137.6, 129.8, 129.5, 129.4, 128.5, 126.5, 114.3, 83.0, 76.1, 72.6, 58.8, 58.5, 55.6, 55.0, 53.8, 52.1, 49.5, 39.4, 36.9, 35.6, 29.7, 27.3, 20.1, 19.9.

(3S,3aR,5R,6aR)-3-(methylsulfonamido)hexahydro-2H-cyclopenta[b]furan-5-yl ((2S,3R)-3-hydroxy-4-(N-isobutyl-4-methoxyphenylsulfonamido)-1-phenylbutan-2-yl)-carbamate (19i). The title compound was obtained from 15i as described for 21a after column chromatography on silica gel using CH₂Cl₂/0.25% to 1.5% MeOH afforded pure inhibitor 15i as a white solid. ¹H NMR (CDCl₃, 400 MHz) δ 7.71 (d, J=8.9 Hz, 2H), 7.33-7.20 (m, 5H), 6.98 (d, J=8.9 Hz, 2H), 5.15-5.05 (m, 2H), 5.05-4.97 (m, 1H), 4.47-4.41 (m, 1H), 4.07-3.97 (m, 1H), 3.88-3.80 (m, 2H), 3.87 (s, 3H), 3.78-3.73 (m, 1H), 3.73-3.68 (m, 2H), 3.13-3.00 (m, 3H), 3.00-2.87 (m, 3H), 2.94 (s, 3H), 2.80 (dd, J=7.0, 13.4 Hz, 1H), 2.05-1.90 (m, 4H), 1.90-1.77 (m, 1H), 0.89 (d, J=6.6 Hz, 3H), 0.86 (d, J=6.6 Hz, 3H).

(3R,3aR,5R,6aR)-3-(methylsulfonamido)hexahydro-2H-cyclopenta[b]furan-5-yl ((2S,3R)-3-hydroxy-4-(N-isobutyl-4-methoxyphenylsulfonamido)-1-phenylbutan-2-yl) carbamate (19j). The title compound was obtained from 15j as described for 19a after column chromatography on silica gel using CH₂Cl₂/MeOH (0.5% to 1.5%) afforded pure inhibitor 19j as a white solid. (CH₂Cl₂/MeOH=); ¹H NMR (CDCl₃, 400 MHz) δ 7.71 (d, J=8.9 Hz, 2H), 7.33-7.19 (m, 5H), 6.98 (d, J=8.9 Hz, 2H), 4.93-4.86 (m, 1H), 4.81 (d, J=7.8 Hz, 1H), 4.61 (dt, J=1.6, 6.4 Hz, 1H), 4.45 (d, J=8.5 Hz, 1H), 3.97 (dd, J=4.9, 9.5 Hz, 1H), 3.87 (s, 3H), 3.88-3.79 (m, 3H), 3.78-3.73 (m, 1H), 3.61-3.55 (m, 1H), 3.12 (dd, J=7.8, 15.1 Hz, 1H), 3.07-3.01 (m, 2H), 2.99 (s, 3H), 2.96-2.91 (m, 1H), 2.91-2.82 (m, 1H), 2.79 (dd, J=6.8, 13.4 Hz, 1H), 2.57-2.52 (m, 1H), 2.22-2.12 (m, 1H), 2.05-1.90 (m, 4H), 1.86-1.76 (m, 1H), 0.91 (d, J=6.6 Hz, 3H), 0.87 (d, J=6.6 Hz, 3H).

(3S,3aR,5R,6aR)-3-(methoxyamino)hexahydro-2H-cyclopenta[b]furan-5-yl (2S,3R)-3-hydroxy-4-(N-isobutyl-4-methoxyphenylsulfonamido)-1-phenylbutan-2-yl carbamate (24a). To a suspension of NaHCO₃ (10 mg, 0.11 mmol) in EtOH (0.5 mL) at 0° C. was added MeONH₂.HCl (7 mg, 0.082 mmol). After stirring for 5 min, a solution of ketone inhibitor 19a in EtOH (0.5 mL+0.5 mL) was added and the mixture was stirred for 2 h. The solution was diluted with EtOAc, filtered on a plug of silica gel rinsing with EtOAc. The resulting organic solution was evaporated to dryness to give an essentially pure mixture of diastereoisomeric oximes (2:1 mixture), off-white solid (16 mg, 96%). To a solution of the oxime derivative in a 1:1 mixture of EtOH:dioxane (0.6 mL) was sequentially added NaBH₃CN (0.12 mmol, 7 mg) followed by AcOH (100 μL). The mixture was stirred at room temperature for 48 h. After addition of saturated NaHCO₃ solution, the aqueous solution was extracted with EtOAc, washed with brine, dried (Na₂SO₄), filtered and evaporated. The residue was purified by column chromatography on silica gel using hexanes:EtOAc (1:1 then 1:3) as the eluent to give inhibitor 24a (4 mg, 66%) as an off-white solid. TLC: R_f=0.22 (hexanes/EtOAc=1:3); ¹H NMR (CDCl₃, 500 MHz) δ 7.71 (d, J=8.8 Hz, 2H), 7.34-7.18 (m, 5H), 6.98 (d, J=8.8 Hz, 1H), 4.96 (m, 1H), 4.82 (d, J=8.0 Hz, 1H), 4.42 (m, 1H), 3.87 (s, 3H), 3.85 (m, 1H), 3.84-3.72 (m, 3H), 3.66 (m, 1H), 3.49 (s, 3H), 3.11 (dd, J=7.9, 15.0 Hz, 1H), 3.04-2.88 (m, 4H), 2.78 (dd, J=6.7, 13.3 Hz, 1H), 2.72 (m, 1H), 2.06 (m, 1H), 2.00 (m, 1H), 1.92-1.76 (3H), 1.62 (br.s, 1H), 0.90 (d, J=6.5 Hz, 3H), 0.86 (d, J=6.5 Hz, 3H); ¹³C NMR (CDCl₃, 125 MHz) δ 163.0, 156.0, 137.6, 129.8, 129.5, 129.4, 128.5, 126.5, 114.3, 84.4, 72.4, 70.1, 61.9, 61.5, 58.8, 55.6, 55.0, 53.7, 44.1, 39.2, 35.5, 30.9, 29.7, 27.2, 20.1, 19.9; HRMS-ESI (m/z): [M+H]⁺ calcd for C₃₀H₄₃N₃O₈SNa 606.2849. found 606.2858.

Abbreviations bis-THF, bis-tetrahydrofuran; Cp-THF, hexahydrocyclopentafuran; PI, protease inhibitor; APV, amprenavir; DRV, darunavir; SQV, saquinavir; IDV, indinavir.

What is claimed is:
1. A compound having the formula

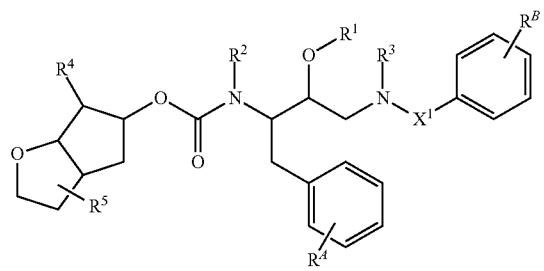

or a pharmaceutically acceptable salt, isomer, mixture of isomers, crystalline form, non crystalline form, hydrate, or solvate thereof; wherein X¹ is C(O), S(O), S(O)₂, HNS(O)₂, HNC(O), or C(O)NH;

R¹ and R² are in each instance independently selected from the group consisting of hydrogen, and a prodrug forming group;

R^A represents from 0 to 4 substituents independently selected in each instance from the group consisting of hydroxy, alkyl, heteroalkyl, alkyloxy, heteroalkyloxy, cycloalkyl, cycloheteroalkyl, aryl, arylalkyl, heteroaryl, or heteroarylalkyl, each of which is optionally substituted; or R^A represents from 2 to 4 substituents where two of the substituents are vicinal substituents and taken with the attached carbons form a carbocycle or heterocycle; and the remaining substituents, if present, are independently selected in each instance from the group consisting of alkyl, heteroalkyl, alkyloxy, heteroalkyloxy, cycloalkyl, cycloheteroalkyl, aryl, arylalkyl, heteroaryl, or heteroarylalkyl, each of which is optionally substituted;

R^B represents from 0 to 4 substituents independently selected in each instance from the group consisting of amino, alkyl, heteroalkyl, alkyloxy, heteroalkyloxy, cycloalkyl, cycloheteroalkyl, aryl, arylalkyl, heteroaryl, or heteroarylalkyl, each of which is optionally substituted; or R^B represents from 2 to 4 substituents where two of the substituents are vicinal substituents and taken with the attached carbons form a carbocycle or heterocycle; and the remaining substituents, if present, are independently selected in each instance from the group consisting of alkyl, heteroalkyl, alkyloxy, heteroalkyloxy, cycloalkyl, cycloheteroalkyl, aryl, arylalkyl, heteroaryl, or heteroarylalkyl, each of which is optionally substituted;

$R^3$ is alkyl, cycloalkyl, arylalkyl, or heteroarylalkyl, each of which is optionally substituted;

$R^4$ and $R^5$ are independently selected in each instance from hydrogen, halogen, oxo, hydroxy, or the group consisting of alkyl, heteroalkyl, alkyloxy, hydroxyalkyl, acyloxy, —OC(C))-amino, acyl, amino, sulfonylamino, acylamino, alkyloxy-C(O)-amino, and alkoxyamino, each of which is optionally substituted, where at least one of $R^4$ or $R^5$ is not hydrogen.

2. The compound of claim 1 wherein the compound has the formula

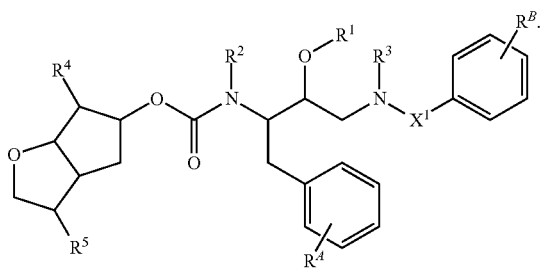

3. The compound of claim 1 wherein the compound has the formula

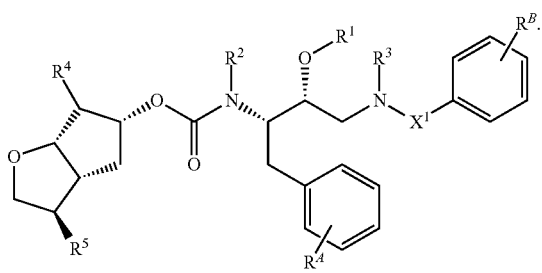

4. The compound of claim 1 wherein $R^4$ is alkyl or an oxygen containing substituent.

5. The compound of claims 1 wherein $R^5$ is alkyl or an oxygen containing substituent.

6. The compound of claim 1 wherein $R^B$ is a substituent at the 4-position selected from the group consisting of amino, alkyloxy, and hydroxyalkyl.

7. The compound of claim 1 wherein $R^B$ is $NH_2$, $CH_3O$, or $CH_2OH$; $X^1$ is $S(O)_2$; $R^3$ is branched alkyl; and $R^A$ represents 0 substituents.

8. The compound of claim 4 wherein $R^4$ is hydroxy or methoxy.

9. The compound of claim 5 wherein $R^5$ is hydroxy or methoxy.

10. The compound of claim 7 wherein $R^3$ is iso-butyl.

11. The compound of claim 1 wherein $R^5$ is amino or methylamino.

12. The compound of claim 1 wherein $R^4$ is hydrogen.

13. The compound of claim 1 wherein $R^5$ is selected from the group consisting of hydroxy, alkyloxy, —OC(O)-amino, acylamino, and sulfonylamino.

14. The compound of claim 1 wherein $R^5$ is hydroxy, methoxy, or acetamido.

15. The compound of claim 1 wherein the compound binds to HIV-1 protease, where the binding includes a direct or indirect interaction between the compound and an Asp29, Asp30, or Gly48 amino acid residues in the protease.

16. A pharmaceutical composition comprising one or more compounds of claim 1, or a pharmaceutically acceptable salt thereof, and one or more carriers, diluents, or excipients, or a combination thereof.

17. A method for treating HIV in a patient, the method comprising the step of administering to the patient a therapeutically effective amount of one or more compounds of claim 1.

* * * * *